(12) United States Patent
He et al.

(10) Patent No.: US 11,447,496 B2
(45) Date of Patent: Sep. 20, 2022

(54) NITROGEN-CONTAINING FUSED HETEROCYCLIC RING COMPOUND AND APPLICATION THEREOF

(71) Applicant: GUANGZHOU CHINARAY OPTOELECTRONIC MATERIALS LTD., Guangdong (CN)

(72) Inventors: Ruifeng He, Guangdong (CN); Junyou Pan, Guangdong (CN)

(73) Assignee: GUANGZHOU CHINARAY OPTOELECTRONIC MATERIALS LTD., Guangdong (CN)

( * ) Notice: Subject to any disclaimer, the term of this patent is extended or adjusted under 35 U.S.C. 154(b) by 684 days.

(21) Appl. No.: 16/463,270

(22) PCT Filed: Nov. 23, 2017

(86) PCT No.: PCT/CN2017/112710
§ 371 (c)(1),
(2) Date: May 22, 2019

(87) PCT Pub. No.: WO2018/095389
PCT Pub. Date: May 31, 2018

(65) Prior Publication Data
US 2020/0223857 A1 Jul. 16, 2020

(30) Foreign Application Priority Data
Nov. 23, 2016 (CN) .......................... 201611046889.2

(51) Int. Cl.
C07D 487/14 (2006.01)
C07D 487/04 (2006.01)
C07D 498/04 (2006.01)
C09K 11/06 (2006.01)
H01L 51/50 (2006.01)

(52) U.S. Cl.
CPC ......... *C07D 487/14* (2013.01); *C07D 487/04* (2013.01); *C07D 498/04* (2013.01); *C09K 11/06* (2013.01); *H01L 51/50* (2013.01)

(58) Field of Classification Search
CPC ............................... C07D 498/04; H01L 51/50
See application file for complete search history.

(56) References Cited

U.S. PATENT DOCUMENTS

| | | | |
|---|---|---|---|
| 4,769,292 A | 9/1988 | Tang et al. | |
| 5,121,029 A | 6/1992 | Hosokawa et al. | |
| 5,130,603 A | 7/1992 | Tokailin et al. | |
| 6,020,078 A | 2/2000 | Chen et al. | |
| 6,251,531 B1 | 6/2001 | Enokida et al. | |
| 6,824,895 B1 | 11/2004 | Sowinski et al. | |
| 6,830,828 B2 | 12/2004 | Thompson et al. | |
| 6,835,469 B2 | 12/2004 | Kwong et al. | |
| 7,029,766 B2 | 4/2006 | Huo et al. | |
| 7,250,532 B2 | 7/2007 | Iwakuma et al. | |
| 9,455,412 B2 | 9/2016 | Zeng et al. | |
| 2001/0053462 A1 | 12/2001 | Mishima | |
| 2005/0258742 A1 | 11/2005 | Tsai et al. | |
| 2006/0210830 A1 | 9/2006 | Funahashi et al. | |
| 2006/0222886 A1 | 10/2006 | Kwong et al. | |
| 2007/0087219 A1 | 4/2007 | Ren et al. | |
| 2007/0092753 A1 | 4/2007 | Begley et al. | |
| 2007/0252517 A1 | 11/2007 | Owczarczyk et al. | |
| 2008/0027220 A1 | 1/2008 | Stossel et al. | |
| 2008/0113101 A1 | 5/2008 | Inoue et al. | |
| 2009/0061681 A1 | 3/2009 | McMunigal et al. | |
| 2009/0134784 A1 | 5/2009 | Lin et al. | |
| 2012/0004407 A1 | 1/2012 | Stoessel et al. | |
| 2012/0217869 A1 | 8/2012 | Adachi et al. | |
| 2015/0243894 A1 | 8/2015 | Zeng et al. | |

(Continued)

FOREIGN PATENT DOCUMENTS

CN 1583691 A 2/2005
CN 102282150 A 12/2011
(Continued)

OTHER PUBLICATIONS

International Search Report received in PCT/CN2017/112710, dated Jan. 31, 2018.
(Continued)

*Primary Examiner* — Peter F Godenschwager
(74) *Attorney, Agent, or Firm* — PV IP PC; Wei Te Chung; Ude Lu

(57) ABSTRACT

The present invention relates to a nitrogen-containing fused heterocyclic ring compound and application thereof. The compound has the structural formula (I):

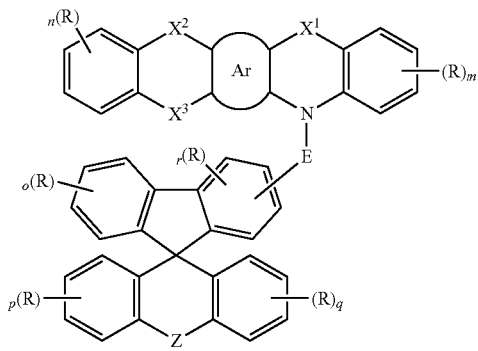

using the described compound, it is possible to fabricate a device having higher stability and a longer service life.

17 Claims, No Drawings

(56) References Cited

U.S. PATENT DOCUMENTS

| | | | |
|---|---|---|---|
| 2015/0337197 A1 | 11/2015 | Jatsch et al. | |
| 2019/0214571 A1* | 7/2019 | Huh | C09K 11/06 |

FOREIGN PATENT DOCUMENTS

| | | |
|---|---|---|
| CN | 102703058 A | 10/2012 |
| CN | 103483332 A | 1/2014 |
| CN | 104797571 A | 7/2015 |
| CN | 104860868 A | 8/2015 |
| CN | 104903328 A | 9/2015 |
| CN | 105358654 A | 2/2016 |
| CN | 106068261 A | 11/2016 |
| DE | 102005058557 A1 | 6/2007 |
| EP | 1191613 B1 | 3/2006 |
| EP | 1957606 A1 | 8/2008 |
| EP | 1191614 B1 | 5/2009 |
| EP | 1191612 B1 | 9/2009 |
| JP | 2913116 B2 | 6/1999 |
| JP | 2008053397 A | 3/2008 |
| TW | 201309696 A | 3/2013 |
| TW | 201309778 A | 3/2013 |
| TW | 201343874 A | 11/2013 |
| TW | 201350558 A | 12/2013 |
| WO | 200070655 A2 | 11/2000 |
| WO | 2001021729 A1 | 3/2001 |
| WO | 200141512 A1 | 6/2001 |
| WO | 200202714 A2 | 1/2002 |
| WO | 200215645 A1 | 2/2002 |
| WO | 2005019373 A2 | 3/2005 |
| WO | 2005033244 A1 | 4/2005 |
| WO | 2006000388 A1 | 1/2006 |
| WO | 2006000389 A1 | 1/2006 |
| WO | 2006058737 A1 | 6/2006 |
| WO | 2006122630 A1 | 11/2006 |
| WO | 2007065549 A1 | 6/2007 |
| WO | 2007095118 A2 | 8/2007 |
| WO | 2007115610 A1 | 10/2007 |
| WO | 2007140847 A1 | 12/2007 |
| WO | 2008006449 A1 | 1/2008 |
| WO | 2009118087 A1 | 10/2009 |
| WO | 2009146770 A2 | 12/2009 |
| WO | 2010015307 A1 | 2/2010 |
| WO | 2010031485 A1 | 3/2010 |
| WO | 2010054728 A1 | 5/2010 |
| WO | 2010054731 A1 | 5/2010 |
| WO | 2010086089 A1 | 8/2010 |
| WO | 2010099852 A1 | 9/2010 |
| WO | 2010102709 A1 | 9/2010 |
| WO | 2010135519 A1 | 11/2010 |
| WO | 2011110277 A1 | 9/2011 |
| WO | 2011141110 A2 | 11/2011 |
| WO | 2011157339 A1 | 12/2011 |
| WO | 2012007086 A1 | 1/2012 |
| WO | 2012007087 A1 | 1/2012 |
| WO | 2012007088 A1 | 1/2012 |
| WO | 2013133359 A1 | 9/2013 |
| WO | 2013154064 A1 | 10/2013 |
| WO | 2013175789 A | 11/2013 |
| WO | 2014088290 A1 | 6/2014 |
| WO | 2015012618 A1 | 1/2015 |
| WO | 2015084021 A1 | 6/2015 |

OTHER PUBLICATIONS

Endo et al, "Thermally Activated Delayed Fluorescence from $Sn^{4+}$-Porphyrin Complexes and Their Application to Organic Light-Emitting Diodes—A Novel Mechanism for Electroluminescence", Adv Mater, vol. 21, 2009, pp. 4802-4806.

Li et al, Highly Efficient Organic Light-Emitting Diode Based on a Hidden Thermally Activated Delayed Fluorescence Channel in a Heptazine Derivative, Adv Mater, vol. 25, 2013, pp. 1-5.

Dias et al, "Triplet Harvesting with 100% Efficiency by Way of Thermally Activated Delayed Fluorescence in Charge Transfer OLEO Emitters", Adv Mater, vol. 25, 2013, pp. 3707-3714.

Mehes et al, "Enhanced Electroluminescence Efficiency in a Spiro-Acridine Derivative through Thermally Activated Delayed Fluorescence", Angew Chem Int Ed, vol. 51, 2012, pp. 11311-11315.

Endo et al, "Efficient up-conversion of triplet excitons into a singlet state and its application for organic light emitting diodes", Appl Phys Lett, vol. 98, 2011, pp. 083302-1-083302-3.

Lee et al, "High-efficiency organic light-emitting diodes utilizing thermally activated delayed fluorescence from triazinebased donor-acceptor hybrid molecules", Appl Phys Lett, vol. 101, 2012, pp. 093306-1-093306-4.

Nakagawa et al, "Electroluminescence based on thermally activated delayed fluorescence generated by a spirobifluorene donor-acceptor structure" Chem Commun, vol. 48, 2012, pp. 9580-9582.

Tanaka et al, "Efficient green thermally activated delayed fluorescence (TADF) from a phenoxazine-triphenyltriazine (PXZ-TRZ) derivative", Chem Commun, vol. 48, 2012, pp. 11392-11394.

Nasu et al, "A highly luminescent spiro-anthracenone-based organic light-emitting diode exhibiting thermally activated delayed fluorescence", Chem Commun, vol. 48, 2013, pp. 1-3.

Komino et al, "Suppression of Efficiency Roll-Off Characteristics in Thermally Activated Delayed Fluorescence Based Organic Light-Emitting Diodes Using Randomly Oriented Host Molecules", Chem Mater, vol. 25, 2013, pp. 3038-3047.

Tanaka et al, "Twisted Intramolecular Charge Transfer State for Long-Wavelength Thermally Activated Delayed Fluorescence", Chem Mater, vol. 25, 2013, pp. 3766-3771.

Zhang et al, "Design of Efficient Thermally Activated Delayed Fluorescence Materials for Pure Blue Organic Light Emitting Diodes", J Am Chem Soc, vol. 134, 2012, pp. 14706-14709.

Lee et al, "Oxadiazole- and triazole-based highly-efficient thermally activated delayed fluorescence emitters for organic light-emitting diodes", J Mater Chem C, vol. 1, 2013, pp. 1-6.

Ishimatsu, "Solvent Effect on Thermally Activated Delayed Fluorescence by 1,2,3,5-Tetrakis(carbazol-9-yl)-4,6-dicyanobenzene", J Phys Chem A, vol. 117, 2013, pp. 5607-5612.

Goushi et al, "Organic light-emitting diodes employing efficient reverse intersystem crossing for triplet-to-singlet state conversion", Nature Photonics, vol. 6, Apr. 2012, pp. 253-258.

Uoyama et al, "Highly efficient organic light-emitting diodes from delayed fluorescence", Nature, vol. 492, Dec. 2012, 234-238.

Adachi et al, "High-efficiency red electrophosphorescence devices", Appl Phys Lett vol. 78 (2001), pp. 1622-1624.

Baldo et al "High-efficiency fluorescent organic light-emitting devices using a phosphorescent sensitizer", Nature, vol. 403, (2000), pp. 750-753.

Kido et al, "Bright red lightemitting organic electroluminescent devices having a europium complex as an emitter", Appl Phys Lett, vol. 65, 1994, pp. 2124-2126.

Johnson et al, "Luminescent Iridium(I), Rhodium(I), and Platinum(II) Dithiolate Complexes", JAGS, vol. 105, 1983, pp. 1795-1802.

Kido et al, "Electroluminescence in a Terbium Complex", Chem Lett (1990), pp. 657-660.

Ma et al, "Electroluminescence from triplet metal-ligand charge-transfer excited state of transition metal complexes" Synth Metals, vol. 94, 1998, pp. 245-248.

Wrighton et al, "The Nature of the Lowest Excited State in Tricarbonylchloro-1,10-phenanthrolinerhenium(I) and Related Complexes", JAGS vol. 96, 1974, pp. 998-1003.

* cited by examiner

NITROGEN-CONTAINING FUSED HETEROCYCLIC RING COMPOUND AND APPLICATION THEREOF

CROSS-REFERENCE TO RELATED APPLICATIONS

The present application is a national stage for International Application No. PCT/CN2017/112710, filed on Nov. 23, 2017, which claims priority to Chinese Application No. 201611046889.2, filed on Nov. 23, 2016, both of which are incorporated herein by reference in their entireties.

TECHNICAL FIELD

The present disclosure relates to the field of electronics, particularly to a nitrogen-containing fused heterocyclic compound and use thereof.

BACKGROUND

An organic semiconducting material is a kind of material, the conductivity of which is between an organic insulator and an organic conductor. The organic semiconducting materials have the characteristics of structural diversity, relatively low manufacturing cost, excellent optoelectronic property, and the like, having great potential for application in optoelectronic devices, particularly in organic light-emitting diodes (OLEDs).

In order to improve the luminous performance of organic light-emitting diodes and promote the industrialization process of organic light-emitting diodes, various organic optoelectronic material systems have been widely developed. Currently, many organic semiconducting materials have poor stability and optoelectronic performance, which leads to poor stability and short lifetime of organic light-emitting diodes. In some researches, in order to improve the stability of organic light-emitting diodes and extend the lifetime of organic light-emitting diodes, materials including nitrogen-containing fused heterocycles are used as the core materials of OLEDs, but due to the planar structure of nitrogen-containing fused heterocycles, the core materials including the nitrogen-containing fused heterocycles have poor solubility and film-forming property, which is very important for solution-based OLEDs, and thus leads to poor stability and relatively short lifetime of the printed light-emitting diodes.

SUMMARY

Accordingly, it is necessary to provide a nitrogen-containing fused heterocyclic compound having a good solubility and film-formation property, and capable of solution-preparing a device having a high stability and a relatively long lifetime, and use thereof.

A nitrogen-containing fused heterocyclic compound has the following formula:

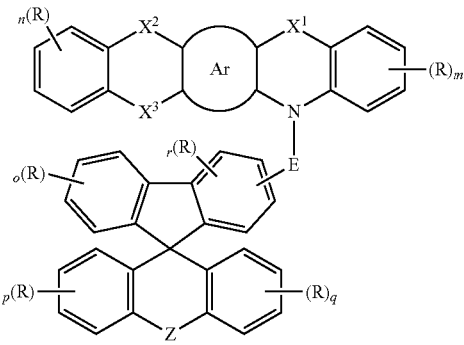

wherein

is an aromatic ring group containing 5 to 30 ring atoms or a heteroaromatic ring group containing 5 to 30 ring atoms;

—$X^1$—, and —$X^3$— are each independently selected from one of the group consisting of a single bond, —N($M^1$)-, —C($M^1$)$_2$-, —Si($M^1$)$_2$-, —O—, —C=N($M^1$)-, —C=C($M^1$)$_2$-, —P($M^1$)-, —P(=O)$M^1$-, —S—, —S=O—, and —$SO_2$—, and —$X^2$— and —$X^3$— are not single bonds simultaneously, wherein $M^1$ is selected from the group consisting of H, D, F, CN, alkenyl, alkynyl, cyano, amino, nitro, acyl, alkoxy, carbonyl, sulfonyl, an alkyl group containing 1 to 30 carbon atoms, a cycloalkyl group containing 3 to 30 carbon atoms, an aromatic ring group containing 5 to 60 ring atoms and a heteroaromatic ring group containing 5 to 60 ring atoms;

—$X^2$— is independently selected from the group consisting of a single bond, —N($M^1$)-, Si($M^1$)$^2$-, —O—, —C=N($M^1$)-, —C=C($M^1$)$^2$-, —P($M^1$)-, —P(=O)$M^1$-, —S—, —S=O—, and —$SO_2$—, and —$X^2$— and —$X^3$— are not single bonds simultaneously, wherein $M^1$ is selected from the group consisting of H, D, F, CN, alkenyl, alkynyl, cyano, amino, nitro, acyl, alkoxy, carbonyl, sulfonyl, an alkyl group containing 1 to 30 carbon atoms, a cycloalkyl group containing 3 to 30 carbon atoms, an aromatic ring group containing 5 to 60 ring atoms and a heteroaromatic ring group containing 5 to 60 ring atoms;

—Z— is one selected from the group consisting of a single bond, —N($M^2$)-, —B($M^2$)-, —C($M^2$)$_2$-, —Si($M^2$)$_2$-, —O—, —S—, —C=N($M^2$)-, —C=C($M^2$)$_2$-, —P($M^2$)-, —P(=O)$M^2$-, —S=O, and —$SO_2$—, wherein $M^2$ is selected from the group consisting of H, D, F, CN, alkenyl, alkynyl, cyano, amino, nitro, acyl, alkoxy, carbonyl, sulfonyl, an alkyl containing 1 to 30 carbon atoms, a cycloalkyl group containing 3 to 30 carbon atoms, an aromatic ring group containing 5 to 60 ring atoms and a heteroaromatic ring group containing 5 to 60 ring atoms;

R is one selected from the group consisting of H, D, F, CN, alkenyl, alkynyl, cyano, amino, nitro, acyl, alkoxy, carbonyl, sulfonyl, an alkyl containing 1 to 30 carbon atoms, a cycloalkyl group containing 3 to 30 carbon atoms, an aromatic ring group containing 5 to 60 ring atoms and a heteroaromatic ring group containing 5 to 60 ring atoms;

m, n, o, p and q are each independently selected from an integer from 0 to 4, and r is selected from an integer from 0 to 3; and E is a heteroatom-containing electron-accepting group.

A spiro group is introduced into the formula of the foregoing nitrogen-containing fused heterocyclic compound. The spiro group has a vertical spatial structure and has a good solubility, stability and optoelectronic property, thus it can enhance the solubility, stability and optoelectronic property of the nitrogen-containing fused heterocyclic compound. Meanwhile, the direct connection between the spiro group and the electron-accepting group can effectively avoid the close packing of the electron-accepting group and reduce the exciton quenching, thereby improving the stability of the nitrogen-containing fused heterocyclic compound, and further improving the stability and lifetime of materials and devices including the nitrogen-containing fused heterocyclic compounds. It has been verified by experiments that the device lifetime of the organic light-emitting diode including the foregoing nitrogen-containing fused heterocyclic compound is more than three times longer than that of the organic light-emitting diode not including the nitrogen-containing fused heterocyclic compound. The foregoing nitrogen-containing fused heterocyclic compound can be used to prepare an electronic device having a higher stability and a longer lifetime.

DETAILED DESCRIPTION OF EMBODIMENTS

In order to facilitate the understanding of the present disclosure, the present disclosure will be described more fully hereinafter. However, the present disclosure may be embodied in many different forms and is not limited to the embodiments described herein. Rather, these embodiments are provided for understanding of the present disclosure more fully.

All technical and scientific terms used herein have the same meaning as commonly understood by those skilled in the art to which the present disclosure belongs, unless otherwise defined. The terms used in the description of the present disclosure is for the purpose of describing specific embodiments and is not intended to limit the disclosure.

A nitrogen-containing fused heterocyclic compound according to one embodiment has the following formula:

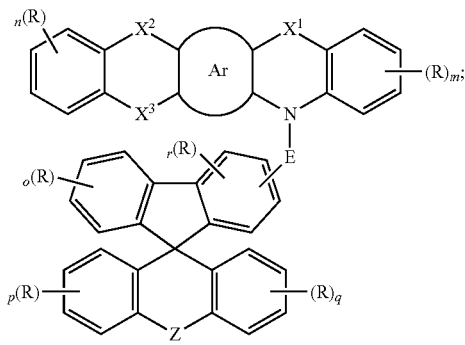

wherein

is an aromatic ring group containing 5 to 30 ring atoms or a heteroaromatic ring group containing 5 to 30 ring atoms;

—$X^1$— and —$X^3$— are each independently selected from the group consisting of a single bond, —$N(M^1)$-, —$C(M^1)_2$-, —$Si(M^1)_2$-, —O—, —$C=N(M^1)$-, —$C=C(M^1)_2$-, —$P(M^1)$-, —$P(=O)M^1$-, —S—, —S=O— and —$SO_2$—, and —$X^2$— and —$X^3$— are not single bonds simultaneously, wherein $M^1$ is selected from the group consisting of H, D, F, CN, alkenyl, alkynyl, cyano, amino, nitro, acyl, alkoxy, carbonyl, sulfonyl, an alkyl group containing 1 to 30 carbon atoms, a cycloalkyl group containing 3 to 30 carbon atoms, an aromatic ring group containing 5 to 60 ring atoms, and a heteroaromatic ring group containing 5 to 60 ring atoms;

—$X^2$— is independently selected from the group consisting of a single bond, —$N(M^1)$-, —$Si(M^1)^2$-, —O—, —$C=N(M^1)$-, —$C=C(M^1)^2$-, —$P(M^1)$-, —$P(=O)M^1$-, —S—, —S=O— and —$SO_2$—, and —$X^2$— and —$X^3$— are not single bonds simultaneously, wherein $M^1$ is selected from the group consisting of H, D, F, CN, alkenyl, alkynyl, cyano, amino, nitro, acyl, alkoxy, carbonyl, sulfonyl, an alkyl group containing 1 to 30 carbon atoms, a cycloalkyl group containing 3 to 30 carbon atoms, an aromatic ring group containing 5 to 60 ring atoms, and a heteroaromatic ring group containing 5 to 60 ring atoms —Z— is one selected from the group consisting of a single bond, —$N(M^2)$-, —$B(M^2)$-, —$C(M^2)_2$-, —$Si(M^2)_2$-, —O—, —S—, —$C=N(M^2)$-, —$C=C(M^2)_2$-, —$P(M^2)$-, —$P(=O)M^2$-, —S=O, and —$SO_2$—, wherein $M^2$ is selected from the group consisting of H, D, F, CN, alkenyl, alkynyl, cyano, amino, nitro, acyl, alkoxy, carbonyl, sulfonyl, an alkyl group containing 1 to 30 carbon atoms, a cycloalkyl group containing 3 to 30 carbon atoms, an aromatic ring group containing 5 to 60 ring atoms, and a heteroaromatic ring group containing 5 to 60 ring atoms;

R is one selected from the group consisting of H, D, F, CN, alkenyl, alkynyl, cyano, amino, nitro, acyl, alkoxy, carbonyl, sulfonyl, an alkyl group containing 1 to 30 carbon atoms, a cycloalkyl group containing 3 to 30 carbon atoms, an aromatic ring group containing 5 to 60 ring atoms, and a heteroaromatic ring group containing 5 to 60 ring atoms;

m, n, o, p and q are each independently selected from an integer from 0 to 4, and r is selected from an integer from 0 to 3; and E is an electron-accepting group containing a heteroatom.

In one embodiment,

is an aromatic ring group containing 5 to 30 ring atoms or a heteroaromatic ring group containing 5 to 30 ring atoms;

An aromatic ring group refers to a hydrocarbyl group containing at least one aromatic ring, including an aromatic ring group having a monocyclic group or an aromatic ring group having a polycyclic group. An aromatic ring group having a polycyclic group refers to a group having a plurality of rings and at least one of which is an aromatic ring, and at least two of which share two adjacent carbon atoms (i.e., forming a fused ring). And, it should be noted that the aromatic ring group includes not only an aromatic ring group having a monocyclic group or an aromatic ring group having a polycyclic group, but also a group having at least two aromatic rings connected by a non-aromatic ring group, wherein the non-aromatic ring group has up to 10% of non-H atoms. In one embodiment, the non-aromatic ring group has up to 5% of non-H atoms. In one embodiment, the non-aromatic ring group is a C atom, N atom or O atom.

The heteroaromatic ring group refers to a hydrocarbyl group containing at least one heteroaromatic ring, including a heteroaromatic ring group having a monocyclic group or a heteroaromatic ring group having a polycyclic ring, wherein the heteroatom in the heteroaromatic ring is one selected from the group consisting of Si, N, P, O, S and Ge. In one embodiment, the heteroatom in the heteroaromatic ring is one selected from the group consisting of Si, N, P, O, and S. A heteroaromatic ring group having a polycyclic group refers to a group having a plurality of rings and at least one of which is a heteroaromatic ring, and at least two of which share two adjacent carbon atoms (i.e., forming a fused ring). And, it should be noted that the heteroaromatic ring group includes not only a heteroaromatic ring group having a monocyclic group or a heteroaromatic ring group having a polycyclic group, but also a group having at least two heteroaromatic rings connected by a non-aromatic ring group, wherein the non-aromatic ring group has up to 10% of non-H atoms. In one embodiment, the non-aromatic ring group has up to 5% of non-H atoms. In one embodiment, the non-aromatic ring group is a C atom, N atom or O atom.

In one embodiment,

is an aromatic ring group containing 5 to 25 ring atoms or a heteroaromatic ring group containing 5 to 25 ring atoms.

In one embodiment,

is an aromatic ring group containing 5 to 20 ring atoms or a heteroaromatic ring group containing 5 to 20 ring atoms.

In one embodiment,

is an aromatic ring group containing 5 to 15 ring atoms or a heteroaromatic ring group containing 5 to 15 ring atoms.

In one embodiment,

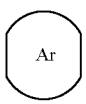

is phenyl, naphthyl, anthryl, phenanthryl, pyrenyl, pyridyl, pyrimidinyl, triazinyl, fluorenyl, dibenzothiophenyl, silafluorenyl, carbazolyl, thienyl, furyl, thiazolyl, triphenylamino, triphenylphosphoryl, tetraphenylsilyl, spirofluorenyl or spirosilafluorenyl.

In one embodiment,

is phenyl, pyridyl, pyrimidinyl, triazinyl or carbazolyl.

In one embodiment,

is one of the following structural formulas or one of the combination groups formed by linking the following structural formulas:

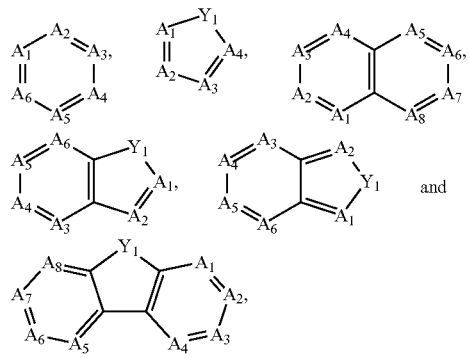

wherein $A^1$, $A^2$, $A^3$, $A^4$, $A^5$, $A^6$, $A^7$ and $A^8$ are each independently selected from $CR^3$ or N;

$Y^1$ is one selected from $CR^4R^5$, $SiR^4R^5$, $NR^3$, $C(=O)$, S and O;

$R^3$, $R^4$ and $R^5$ are each independently selected from the groups consisting of H, D, a linear alkyl group containing 1 to 20 carbon atoms, an linear alkoxy group containing 1 to 20 carbon atoms, a linear thioalkoxy group containing 1 to 20 carbon atoms, a branched alkyl group containing 3 to 20 carbon atoms, a cyclic alkyl group containing 3 to 20 carbon atoms, a branched alkoxy containing 3 to 20 carbon atoms, a cyclic alkoxy containing 3 to 20 carbon atoms, a branched thioalkoxy group containing 3 to 20 carbon atoms, a cyclic thioalkoxy group containing 3 to 20 carbon atoms, a branched silyl group containing 3 to 20 carbon atoms, a cyclic silyl group containing 3 to 20 carbon atoms, a substituted keto group containing 1 to 20 carbon atoms, an alkoxycarbonyl group containing 2 to 20 carbon atoms, an aryloxycarbonyl group containing 7 to 20 carbon atoms, a cyano group, $C(=O)NH_2$, a haloformyl group, $C(=O)-H$, an isocyano group, an isocyanate group, a thiocyanate group, an isothiocyanate group, a hydroxyl group, a nitryl group, a $CF_3$ group, Cl, Br, F, a crosslinkable group, a substituted aromatic ring group containing 5 to 40 ring atoms, a non-substituted aromatic ring group containing 5 to 40 ring atoms, a non-substituted heteroaromatic ring group containing 5 to 40 ring atoms, a substituted heteroaromatic ring group containing 5 to 40 ring atoms, an aryloxy group containing 5 to 40 ring atoms, a heteroaryloxy group containing 5 to 40 ring atoms, and one of the combination groups formed by the foregoing groups linked to each other.

In one embodiment, $R^3$, $R^4$ and $R^5$ each can form a monocyclic aliphatic ring group, a polycyclic aliphatic ring group, a monocyclic aromatic ring group or a polycyclic aromatic ring group by itself.

In one embodiment, a monocyclic aliphatic ring group, a polycyclic aliphatic ring group, a monocyclic aromatic ring group or a polycyclic aromatic ring group can be formed between $R^3$ and $R^4$.

In one embodiment, a monocyclic aliphatic ring group, a polycyclic aliphatic ring group, a monocyclic aromatic ring group or a polycyclic aromatic ring group can be formed between $R^4$ and $R^5$.

In one embodiment, when

is one of the combination groups formed by linking the foregoing formulas linked, a monocyclic aliphatic ring group, a polycyclic aliphatic ring group, a monocyclic aromatic ring group or a polycyclic aromatic ring group can be formed between $R^3$ and $R^4$, $R^4$ and $R^5$, and $R^3$ and $R^5$.

In one embodiment,

is one selected from the following structural formulas:

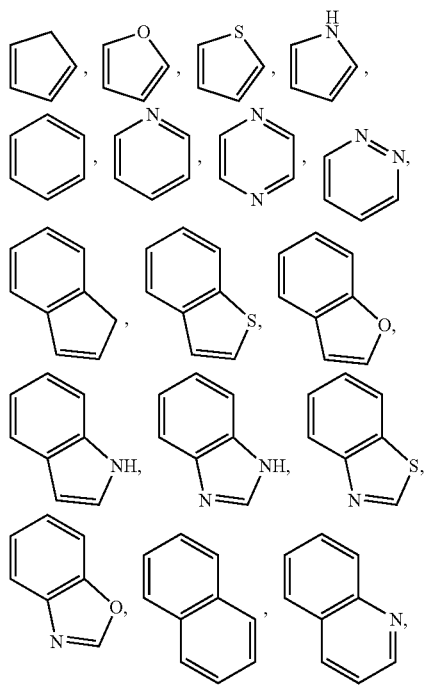

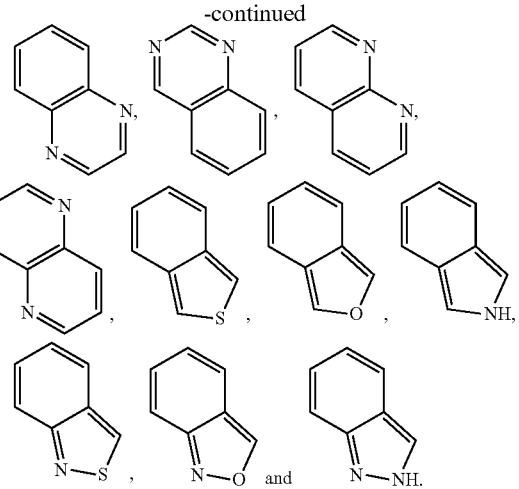

And, it should be noted that H atom in the foregoing formulas may be substituted by any group, for example, by deuterium, an alkyl group containing 1 to 20 carbon atoms, a cycloalkyl group containing 3 to 20 carbon atoms, an aromatic ring group containing 6 to 30 ring atoms or a heteroaromatic ring group containing 3 to 30 ring atoms; wherein the heteroatom in the heteroaromatic ring group is O, S or N.

In one embodiment, —$X^1$— and —$X^3$— are each independently selected from the group consisting of a single bond, —N($M^1$)-, —C($M^1$)$_2$-, —Si($M^1$)$_2$-, —O—, —C=N($M^1$)-, —C=C($M^1$)$_2$-, —P($M^1$)-, —P(=O)$M^1$-, —S—, —S=O—, and —SO$_2$—, and —$X^1$— and —$X^3$— are not single bonds simultaneously, wherein $M^1$ is selected from the group consisting of H, D, F, CN, alkenyl, alkynyl, cyano, amino, nitro, acyl, alkoxy, carbonyl, sulfonyl, an alkyl group containing 1 to 30 carbon atoms, a cycloalkyl group containing 3 to 30 carbon atoms, an aromatic ring group containing 5 to 60 ring atoms, and a heteroaromatic ring group containing 5 to 60 ring atoms;

In one embodiment, —$X^1$— and $X^3$— are each independently selected from the group consisting of a single bond, —N($M^1$)-, —C($M^1$)$_2$-, —O—, and —S—, and —$X^1$— and —$X^3$— are not single bonds simultaneously.

In one embodiment, $M^1$ is one selecting from the group consisting of methyl, phenyl, biphenyl, naphthyl, anthryl, phenanthryl, pyrenyl, pyridyl, pyrimidinyl, triazinyl, fluorenyl, dibenzothiophenyl, silafluorenyl, carbazolyl, thienyl, furyl, thiazolyl, triphenylamino, triphenylphosphoryl, tetraphenylsilyl, spirofluorenyl and spirosilafluorenyl.

In one embodiment, $M^1$ is one selected from the group consisting of phenyl, biphenyl, pyridyl, pyrimidinyl, triazinyl and carbazolyl.

In one embodiment, —Z— is selected from the group consisting of a single bond, —N($M^2$)-, —B($M^2$)-, —C($M^2$)$_2$-, —Si($M^2$)$_2$-, —O—, —S—, —C=N($M^2$)-, —C=C($M^2$)$_2$-, —P($M^2$)-, —P(=O)$M^2$-, —S=O, and —SO$_2$—, wherein $M^2$ is selected from the group consisting of H, D, F, CN, alkenyl, alkynyl, cyano, amino, nitro, acyl, alkoxy, carbonyl, sulfonyl, an alkyl containing 1 to 30 carbon atoms, a cycloalkyl group containing 3 to 30 carbon atoms, an aromatic ring group containing 5 to 60 ring atoms, and a heteroaromatic ring group containing 5 to 60 ring atoms.

In one embodiment, —Z— is one selected from the group consisting of a single bond, —N($M^2$)-, —C($M^2$)$_2$-, —O—, and —S—.

In one embodiment, M² is one selecting from the group consisting of methyl, phenyl, biphenyl, naphthyl, anthryl, phenanthryl, pyrenyl, pyridyl, pyrimidinyl, triazinyl, fluorenyl, dibenzothiophenyl, silafluorenyl, carbazolyl, thienyl, furyl, thiazolyl, triphenylamino, triphenylphosphoryl, tetraphenylsilyl, spirofluorenyl and spirosilafluorenyl.

In one embodiment, M² is one selected from the group consisting of phenyl, biphenyl, pyridyl, pyrimidinyl, triazinyl and carbazolyl.

In one embodiment, R is one selected from the group consisting of H, D, F, CN, alkenyl, alkynyl, cyano, amino, nitro, acyl, alkoxy, carbonyl, sulfonyl, an alkyl containing 1 to 30 carbon atoms, a cycloalkyl group containing 3 to 30 carbon atoms, an aromatic ring group containing 5 to 60 ring atoms or a heteroaromatic ring group containing 5 to 60 ring atoms.

In one embodiment, R is one selecting from the group consisting of methyl, phenyl, biphenyl, naphthyl, anthryl, phenanthryl, pyrenyl, pyridyl, pyrimidinyl, triazinyl, fluorenyl, dibenzothiophenyl, silafluorenyl, carbazolyl, thienyl, furyl, thiazolyl, triphenylamino, triphenylphosphoryl, tetraphenylsilyl, spirofluorenyl and spirosilafluorenyl.

In one embodiment, R is one selected from the group consisting of phenyl, biphenyl, pyridyl, pyrimidinyl, triazinyl and carbazolyl.

In one embodiment, R can be attached to any one of the carbon atoms of the corresponding benzene ring in the structural formulas of the foregoing nitrogen-containing fused heterocyclic compound.

In one embodiment, m, n, o, p and q are each independently selected from an integer from 0 to 4, and r is selected from an integer from 0 to 3.

In one embodiment, E is a heteroatom-containing electron-accepting group.

In one embodiment, E is a heteroatom-containing electron-accepting group containing 0 to 25 carbon atoms.

In one embodiment, E is a heteroatom-containing electron-accepting group containing 0 to 15 carbon atoms.

In one embodiment, E is an electron-accepting group containing a heteroatom which is N, O or P.

In one embodiment, E is one selected from the following structural formulas:

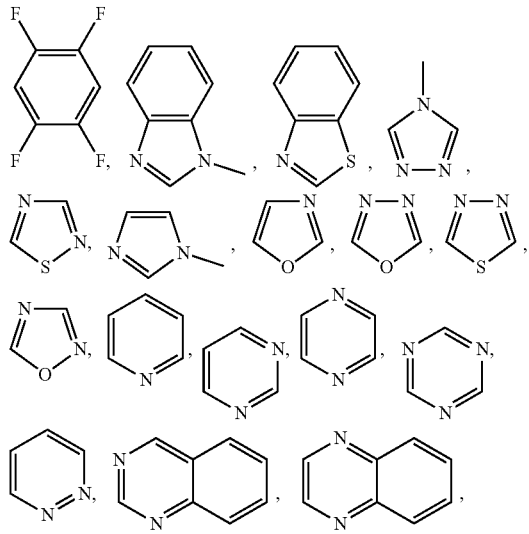

wherein —Z¹—, —Z²— and —Z³— are each independently selected from the group consisting of —N(M³)-, —C(M³)²-, —Si(M³)²-, —O—, —C=N(M³)-, —C=C(M³)²-, —P(M³)-, —P(=O)M³-, —S—, —S=O— and —SO₂—, or —Z¹—, —Z²—, —Z³— are not present, and M³ is selected from the group consisting of H, D, F, CN, alkenyl, alkynyl, cyano, amino, nitro, acyl, alkoxy, carbonyl, sulfonyl, an alkyl group containing 1 to 30 carbon atoms, a cycloalkyl group containing 3 to 30 carbon atoms, an aromatic ring group containing 5 to 60 ring atoms and a heteroaromatic ring group containing 5 to 60 ring atoms;

$g^1$, $g^2$, $g^3$, $g^4$, $g^5$, $g^6$, $g^7$ and $g^8$ are each independently selected from $CR^6$ or N, and at least one of $g^1$, $g^2$, $g^3$, $g^4$, $g^5$, $g^6$, $g^7$ and $g^8$ is N, and $R^6$ is one selected from the group consisting of H, D, a linear alkyl group containing 1 to 20 carbon atoms, a linear alkoxy group containing 1 to 20 carbon atoms, a linear thioalkoxy group containing 1 to 20 carbon atoms, a branched alkyl group containing 3 to 20 carbon atoms, a cyclic alkyl group containing 3 to 20 carbon atoms, a branched alkoxy containing 3 to 20 carbon atoms, a cyclic alkoxy containing 3 to 20 carbon atoms, a branched thioalkoxy group containing 3 to 20 carbon atoms, a cyclic thioalkoxy group containing 3 to 20 carbon atoms, a branched silyl group containing 3 to 20 carbon atoms, a cyclic silyl group containing 3 to 20 carbon atoms, a substituted keto group containing 1 to 20 carbon atoms, an alkoxycarbonyl group containing 2 to 20 carbon atoms, an aryloxycarbonyl group containing 7 to 20 carbon atoms, a cyano group, C(=O)NH$_2$, a haloformyl group, C(=O)—H, an isocyano group, an isocyanate group, a thiocyanate group, an isothiocyanate group, a hydroxyl group, a nitryl group, a CF$_3$ group, Cl, Br, F, a crosslinkable group, a substituted aromatic ring system containing 5 to 40 ring atoms, a non-substituted aromatic ring system containing 5 to 40 ring atoms, a non-substituted heteroaromatic ring system containing 5 to 40 ring atoms, a substituted heteroaromatic ring system containing 5 to 40 ring atoms, an aryloxy group containing 5 to 40 ring atoms, a heteroaryloxy group containing 5 to 40 ring atoms, and one of the combination groups formed by the foregoing groups linked to each other, wherein R$^6$ can form a monocyclic aliphatic ring group, a polycyclic aliphatic ring group, a monocyclic aromatic ring group or a polycyclic aromatic ring group by itself.

In one embodiment, -E- is one selected from the following structural formulas:

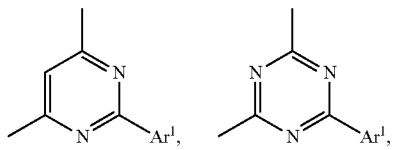

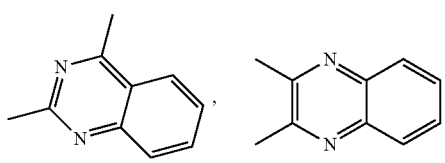

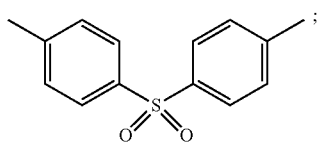

wherein Ar$^1$ is one selected from the group consisting of an alkyl group containing 1 to 30 carbon atoms, a cycloalkyl group containing 3 to 30 carbon atoms, an aromatic ring group containing 5 to 60 ring atoms, and a heteroaromatic ring group containing 5 to 60 ring atoms.

In one embodiment, E can be attached to any one of the carbon atoms forming the spiro structure in

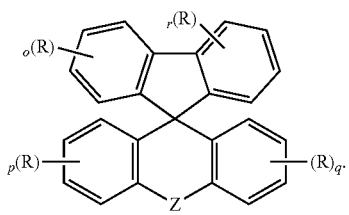

In one embodiment, the nitrogen-containing fused heterocyclic compound has a formula as:

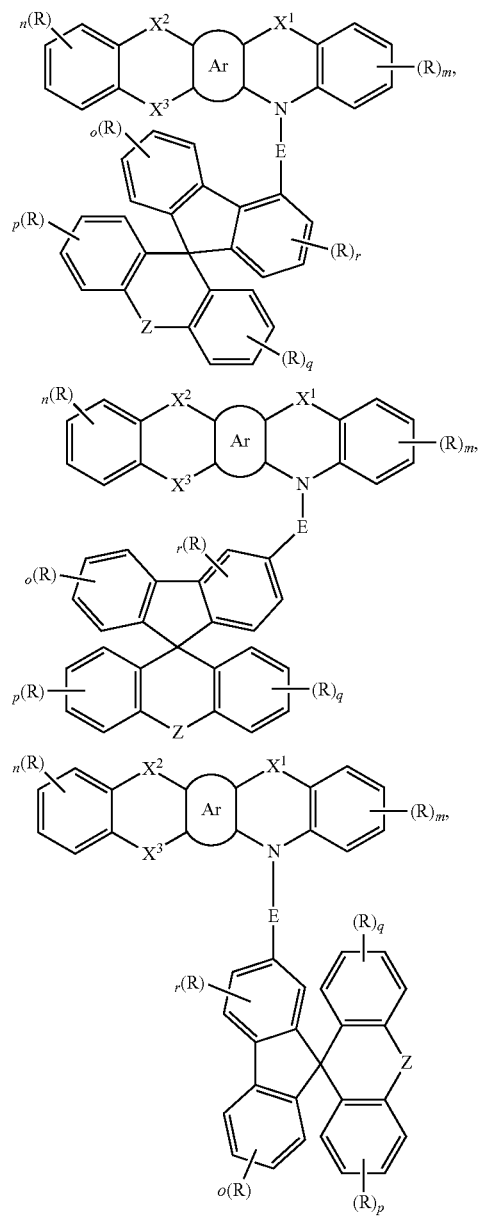

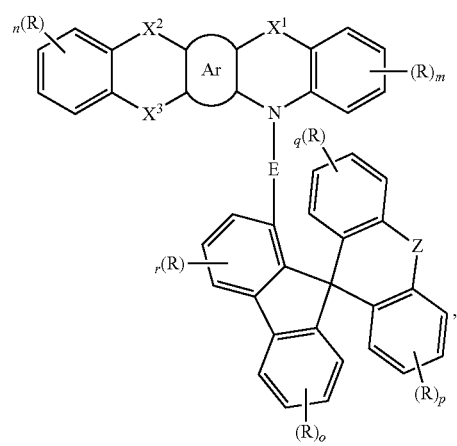

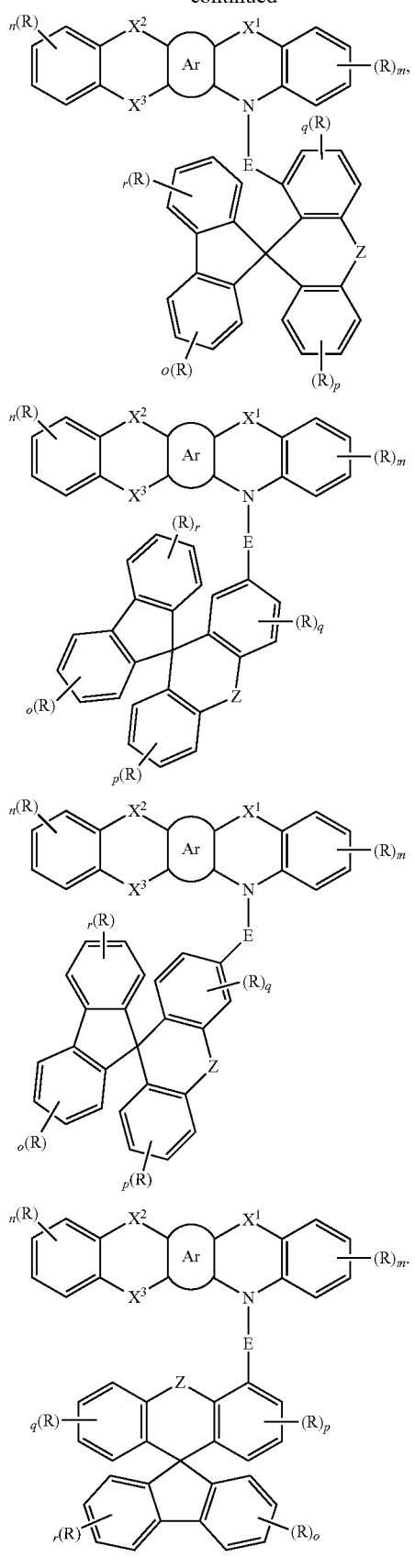
In one embodiment, the nitrogen-containing fused heterocyclic compound has a formula as:
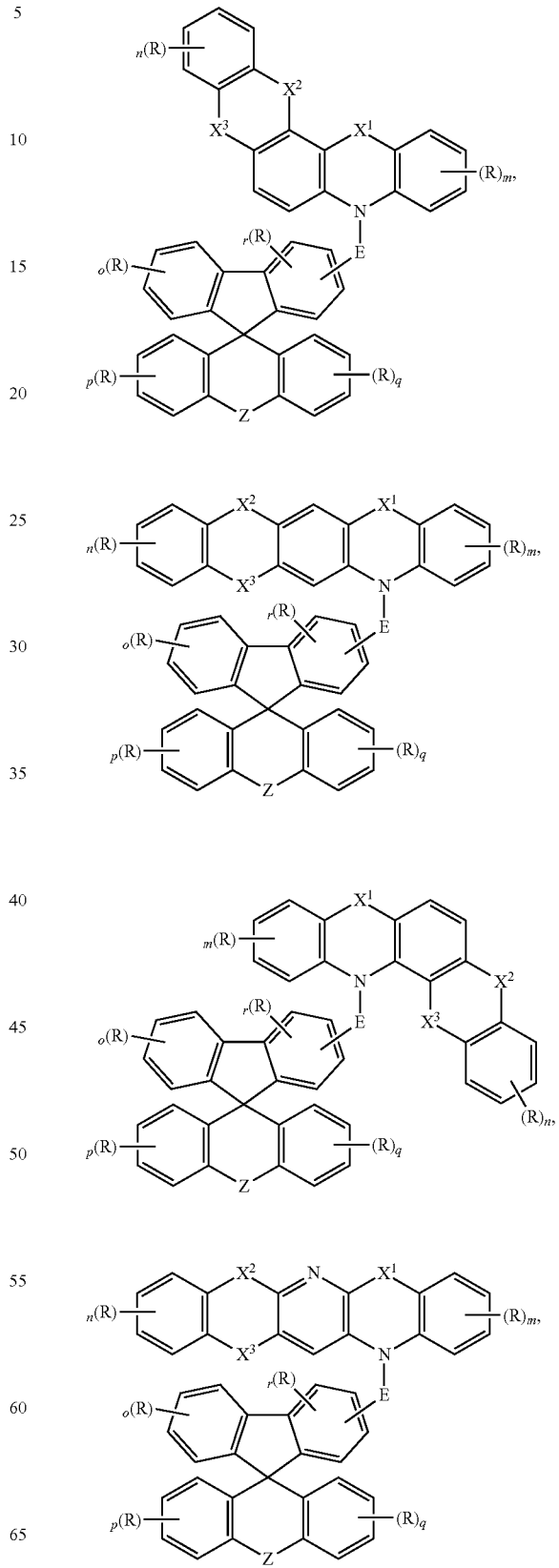

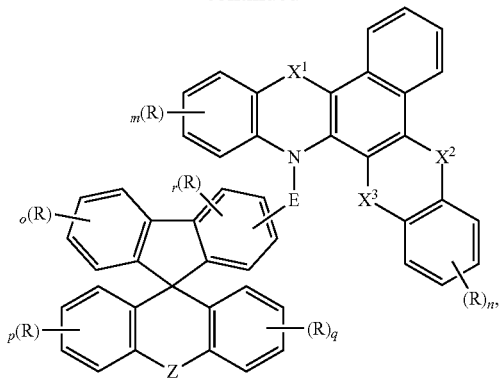

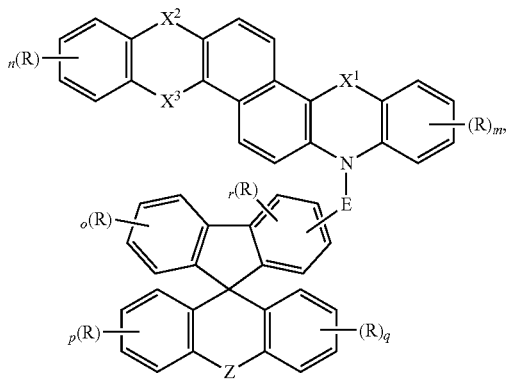

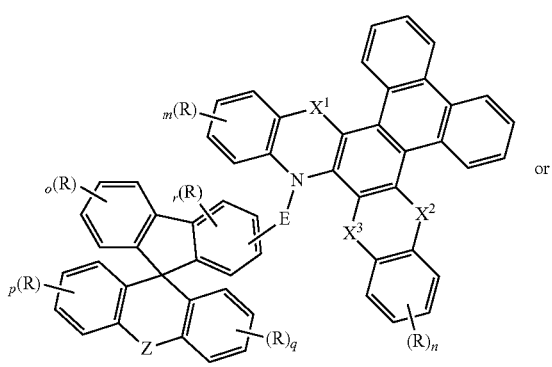

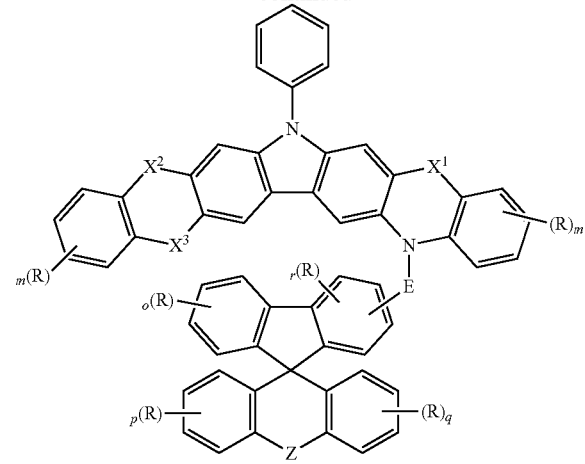

In one embodiment, the nitrogen-containing fused heterocyclic compound has a $T_1$ (triplet excited state energy level) greater than or equal to 2.0 eV. The higher the $T_1$, the closer the $T_1$ is to the $S_1$ (single excited state energy level), consequently the smaller the compound $\Delta E_{ST}$ (i.e., ($S_1$-$T_1$), the difference between the singlet energy level and the triplet energy level). When $\Delta E_{ST}$ is small enough, triplet excitons of the compound can be converted to singlet excitons by internal reversion and resulting in efficient luminescence, so that the compound has the characteristics of a TADF (thermally activated delayed fluorescence) material and can be used as a phosphorescent host material.

In one embodiment, the nitrogen-containing fused heterocyclic compound has a $T_1$ (triplet excited state energy level) greater than or equal to 2.2 eV.

In one embodiment, the nitrogen-containing fused heterocyclic compound has a $T_1$ greater than or equal to 2.4 eV.

In one embodiment, the nitrogen-containing fused heterocyclic compound has a $T_1$ greater than or equal to 2.5 eV.

In one embodiment, the nitrogen-containing fused heterocyclic compound has a $T_1$ greater than or equal to 2.7 eV.

In one embodiment, the nitrogen-containing fused heterocyclic compound has a $\Delta E_{ST}$ less than or equal to 0.30 eV. A sufficiently small $\Delta E_{ST}$ allows the compound to have the characteristics of a TADF (thermally activated delayed fluorescence) material, i.e., triplet excitons can be converted to singlet excitons by internal reversion, facilitating achieving efficient luminescence.

In one embodiment, the nitrogen-containing fused heterocyclic compound has a $\Delta E_{ST}$ less than or equal to 0.25 eV.

In one embodiment, the nitrogen-containing fused heterocyclic compound has a $\Delta E_{ST}$ less than or equal to 0.20 eV.

In one embodiment, the nitrogen-containing fused heterocyclic compound has a $\Delta E_{ST}$ less than or equal to 0.15 eV.

In one embodiment, the nitrogen-containing fused heterocyclic compound has a $\Delta E_{ST}$ less than or equal to 0.10 eV.

In one embodiment, the nitrogen-containing fused heterocyclic compound has a formula as:

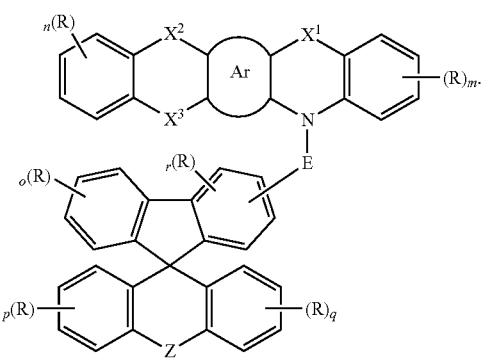

In one embodiment, at least one of —$X^2$— and —$X^3$— is —$N(M^1)$-, so that the nitrogen-containing fused heterocyclic compound has a distinct D-A structure, i.e., a compound formed by the linkage of an electron-donating group (Donor) and an electron-accepting group (Acceptor).

In one embodiment, the nitrogen-containing fused heterocyclic compound has a structural formula where 10% of H atoms are substituted with D atoms.

In one embodiment, the nitrogen-containing fused heterocyclic compound has a structural formula where 20% of H atoms are substituted with D atoms.

In one embodiment, the nitrogen-containing fused heterocyclic compound has a structural formula where 30% of H atoms are substituted with D atoms.

In one embodiment, the nitrogen-containing fused heterocyclic compound has a structural formula where 40% of H atoms are substituted with D atoms.

The foregoing structural formula contains a conjugated system:

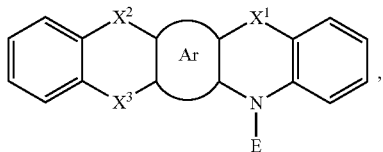

resulting in a higher $T_1$ of the nitrogen-containing fused heterocyclic compound.

In one embodiment, in the case where the hydrogen in the conjugated system is unsubstituted, the conjugated system has ring atoms less than or equal to 36.

In one embodiment, in the case where the hydrogen in the conjugated system is unsubstituted, the conjugated system has ring atoms less than or equal to 32.

In one embodiment, in the case where the hydrogen in the conjugated system is unsubstituted, the conjugated system has ring atoms less than or equal to 28.

In one embodiment, in the case where the hydrogen in the conjugated system is unsubstituted, the conjugated system has a $T_1$ greater than or equal to 2.2 eV.

In one embodiment, in the case where the hydrogen in the conjugated system is unsubstituted, the conjugated system has a $T_1$ greater than or equal to 2.4 eV.

In one embodiment, in the case where the hydrogen in the conjugated system is unsubstituted, the conjugated system has a $T_1$ greater than or equal to 2.5 eV.

In one embodiment, in the case where the hydrogen in the conjugated system is unsubstituted, the conjugated system has a $T_1$ greater than or equal to 2.6 eV.

In one embodiment, in the case where the hydrogen in the conjugated system is unsubstituted, the conjugated system has a $T_1$ greater than or equal to 2.7 eV.

In one embodiment, the nitrogen-containing fused heterocyclic compound has a formula as:

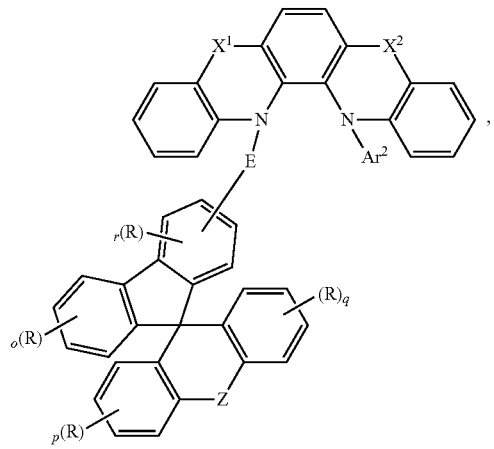

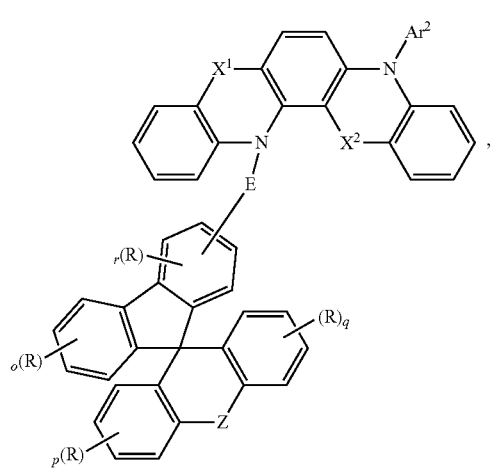

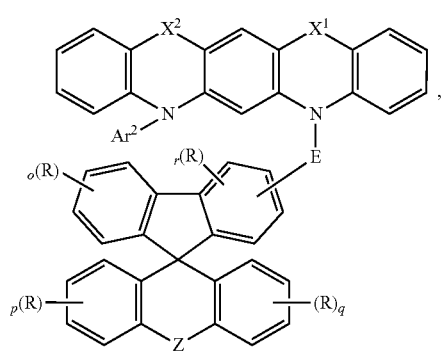

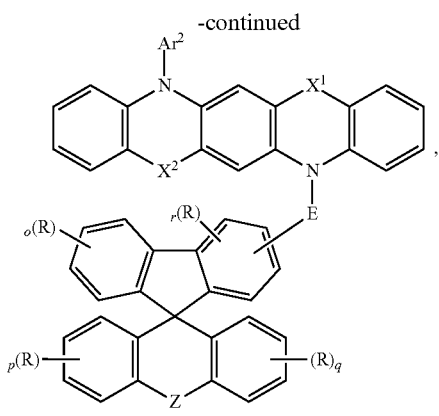

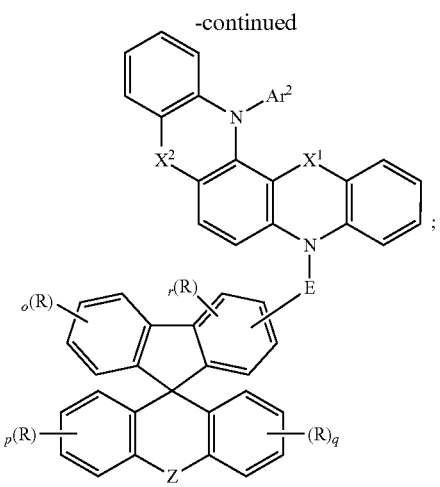

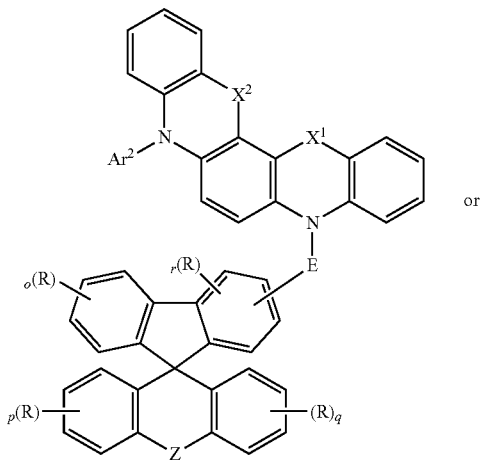

wherein Ar² is selected from the group consisting of an alkyl group containing 1 to 20 carbon atoms, a cycloalkyl group containing 3 to 20 carbon atoms, an aromatic ring group containing 6 to 30 ring atoms, and a heteroaromatic ring group containing 6 to 30 ring atoms.

In one embodiment, Ar² is one selecting from the group consisting of methyl, phenyl, biphenyl, naphthyl, anthryl, phenanthryl, pyrenyl, pyridyl, pyrimidinyl, triazinyl, fluorenyl, dibenzothiophenyl, silafluorenyl, carbazolyl, thienyl, furyl, thiazolyl, triphenylamino, triphenylphosphoryl, tetraphenylsilyl, spirofluorenyl or spirosilafluorenyl, and one of the combination groups formed by the foregoing groups linked to each other.

In one embodiment, the nitrogen-containing fused heterocyclic compound has a structural formula as:

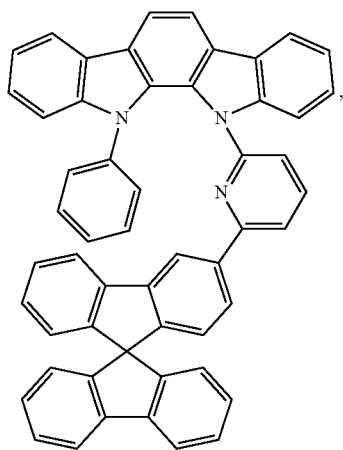

(5-1)

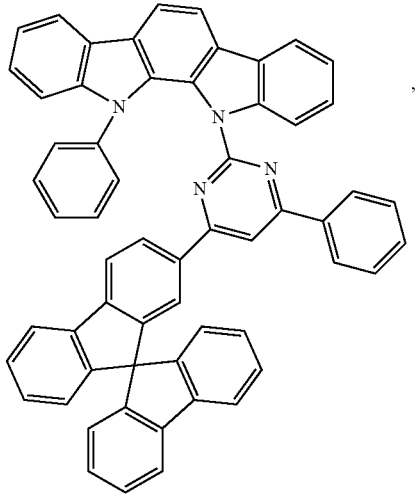

(5-2)

-continued
(5-3)
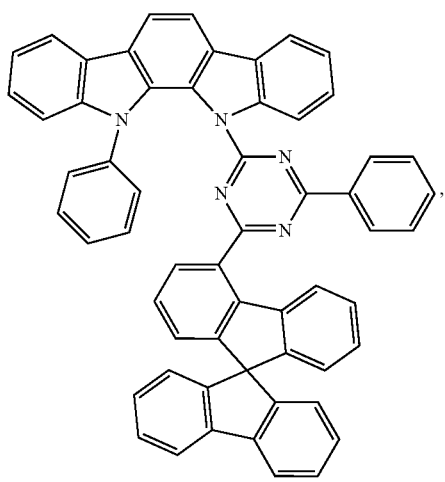
(5-4)
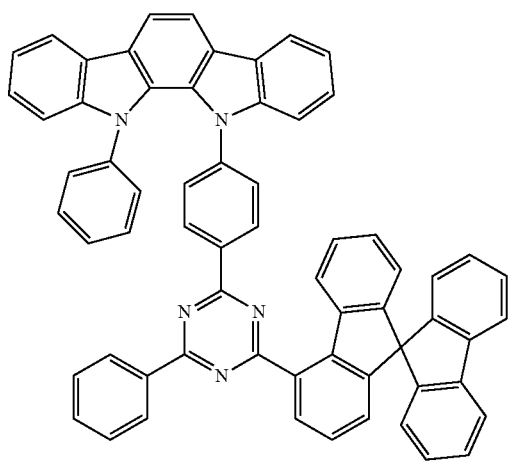
(5-5)
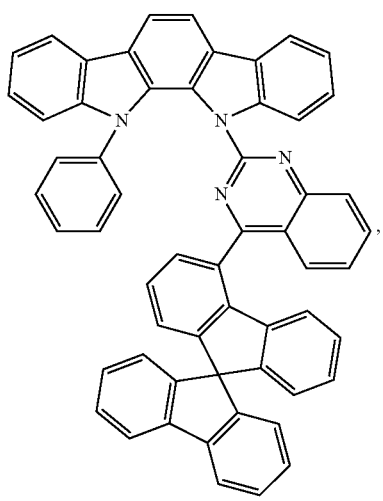
(5-6)
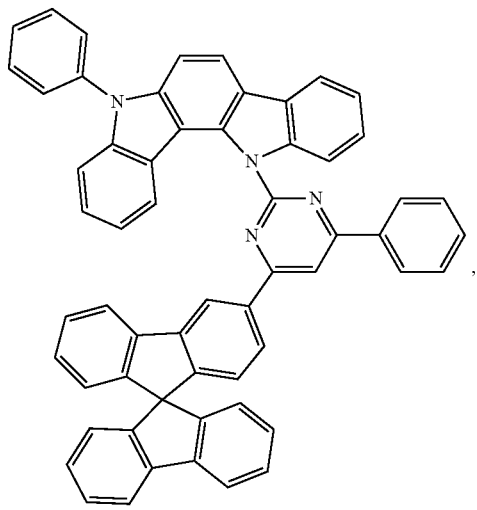
(5-7)
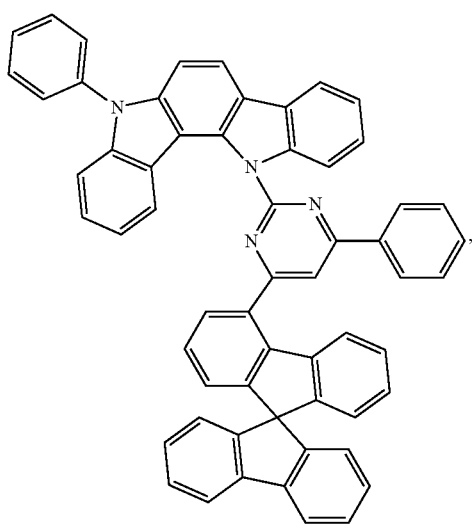
(5-8)
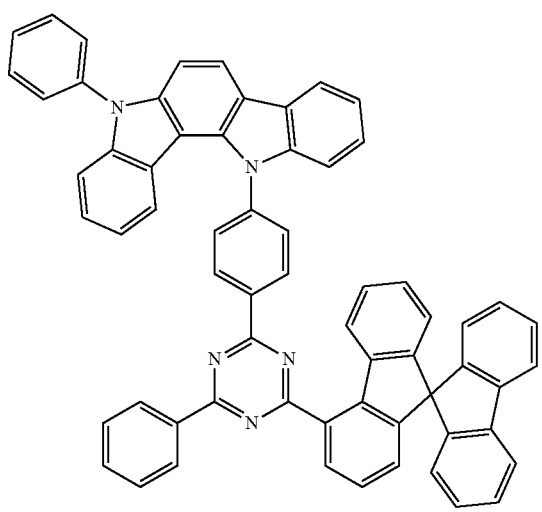

-continued
(5-9)
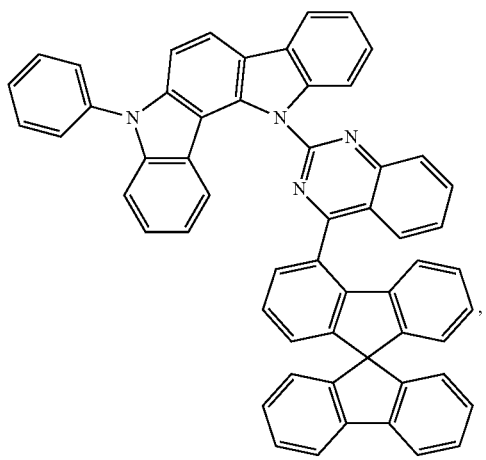
(5-10)
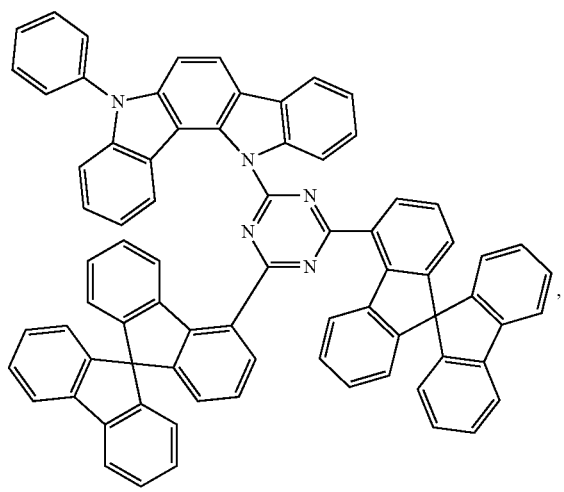
(5-11)
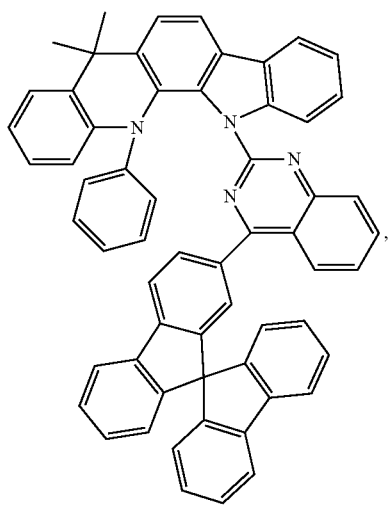
(5-12)
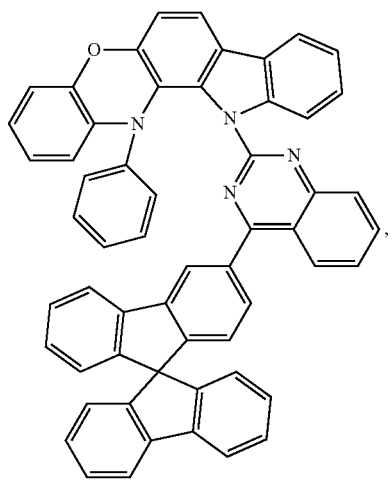
(5-13)
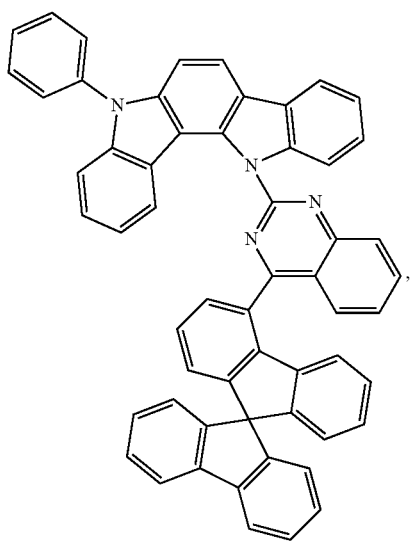
(5-14)
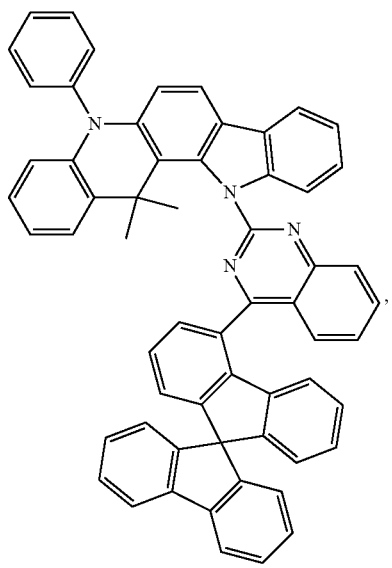

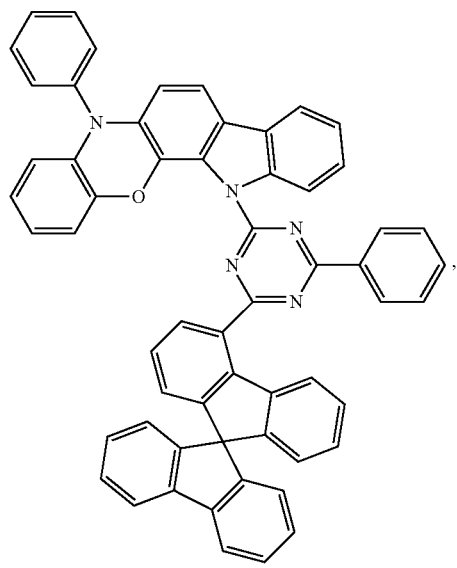
(5-15)
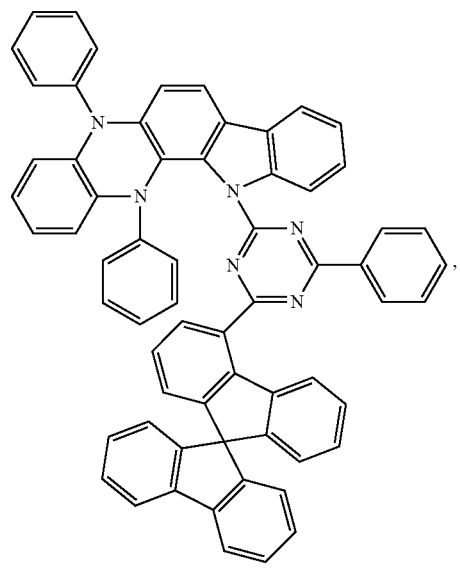
(5-16)
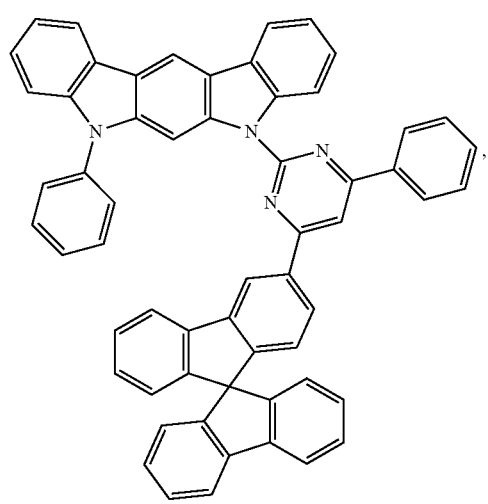
(6-1)
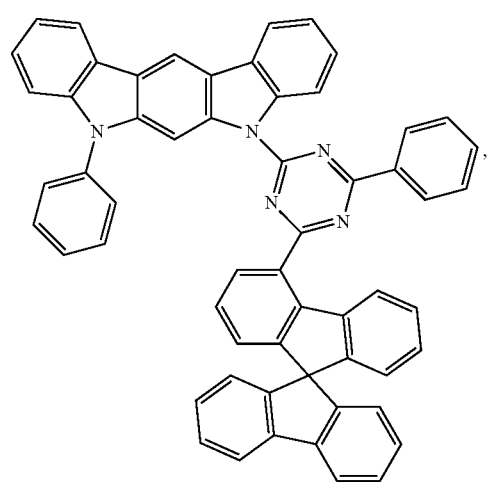
(6-2)
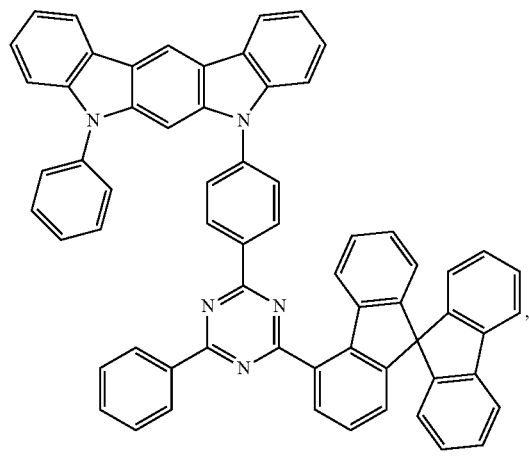
(6-3)
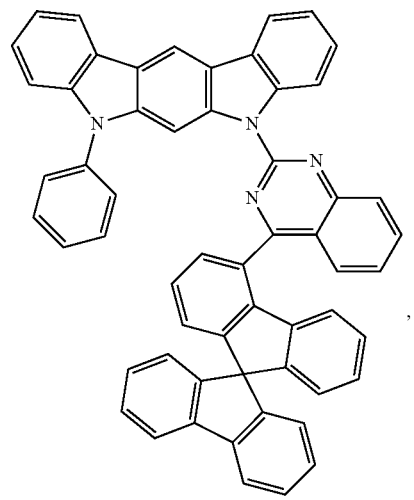
(6-4)

-continued
(6-5)
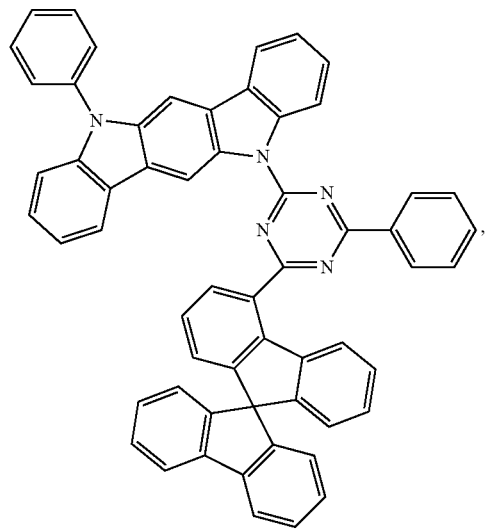
(6-6)
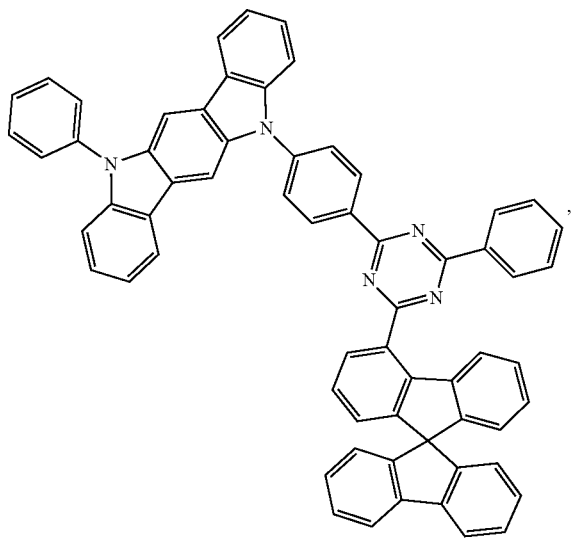
(6-7)
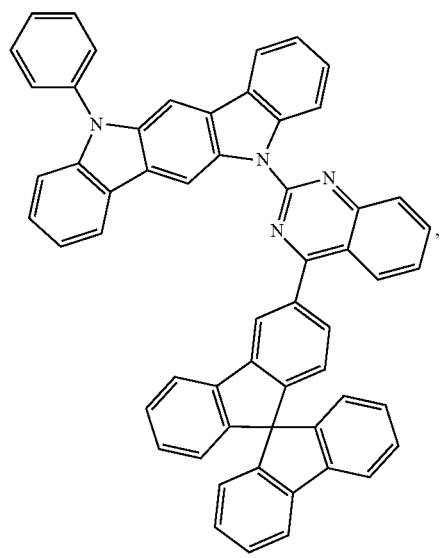
(6-8)
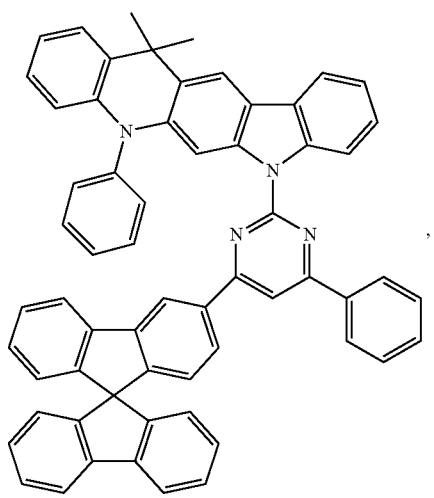
(6-9)
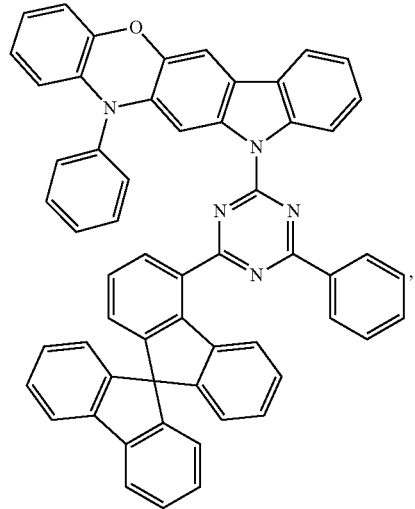
(6-10)
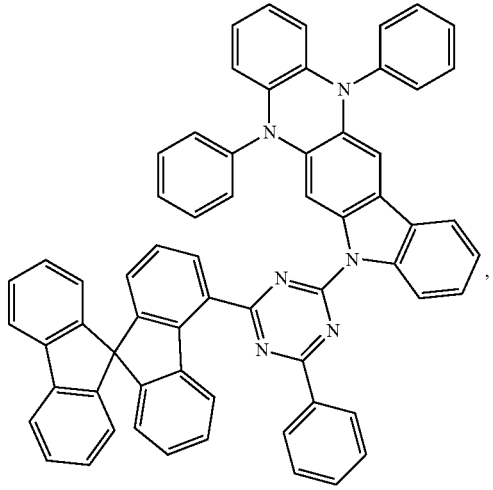

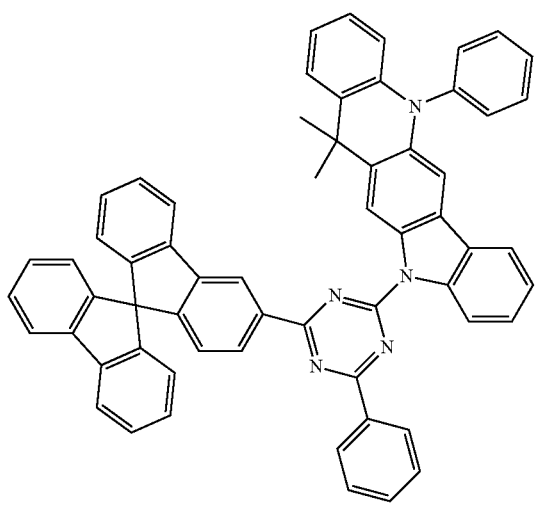
(6-11)
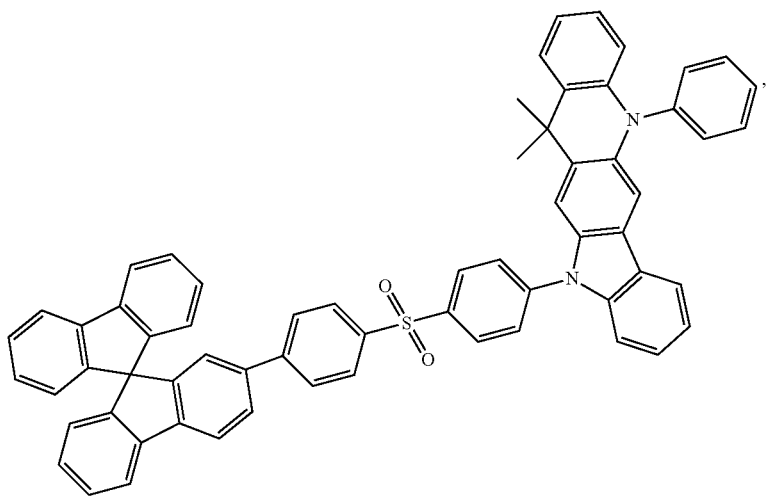
(6-12)
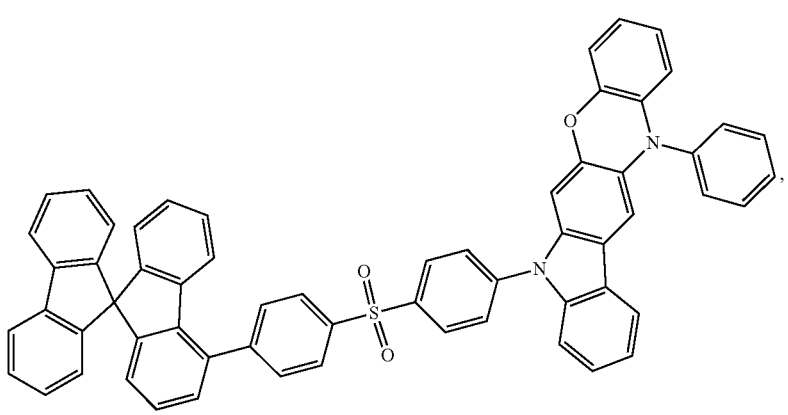
(6-13)

(6-14)
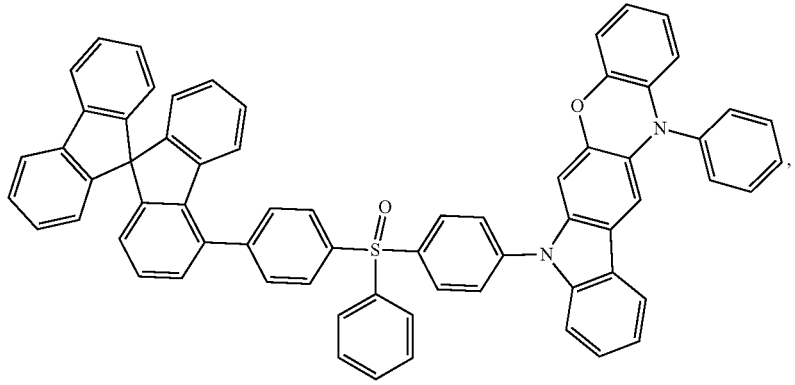
(6-15)
(7-1)
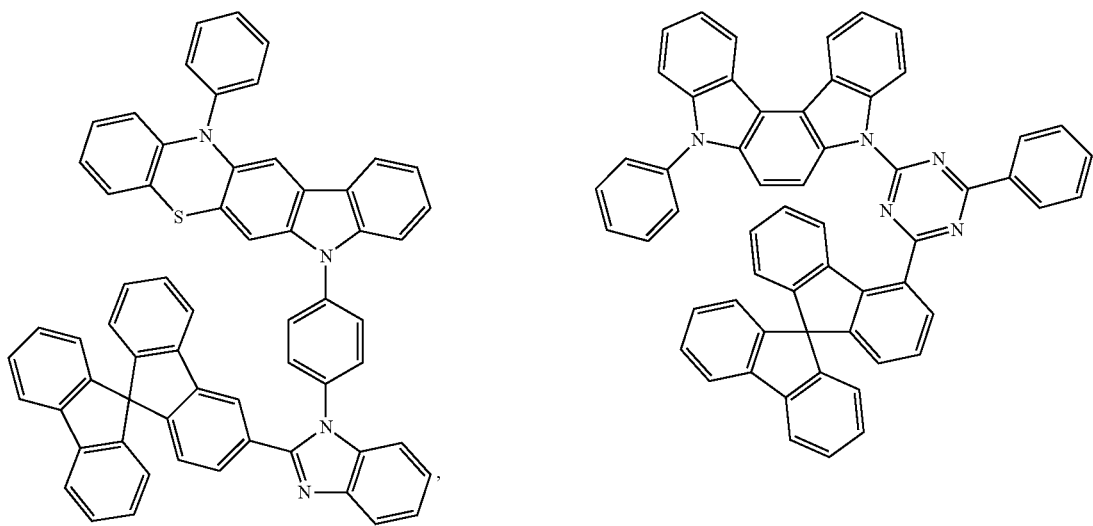
(7-12)
(7-3)
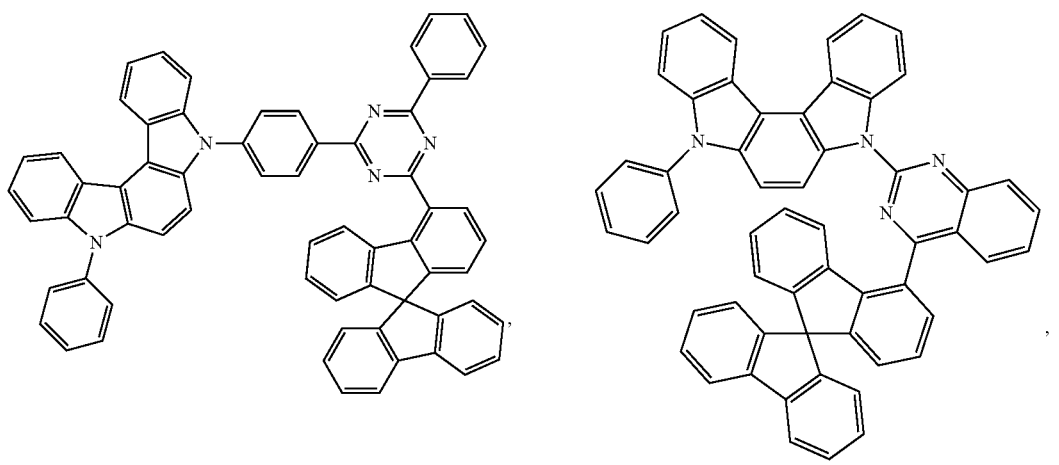

-continued
(7-4)
(7-5)
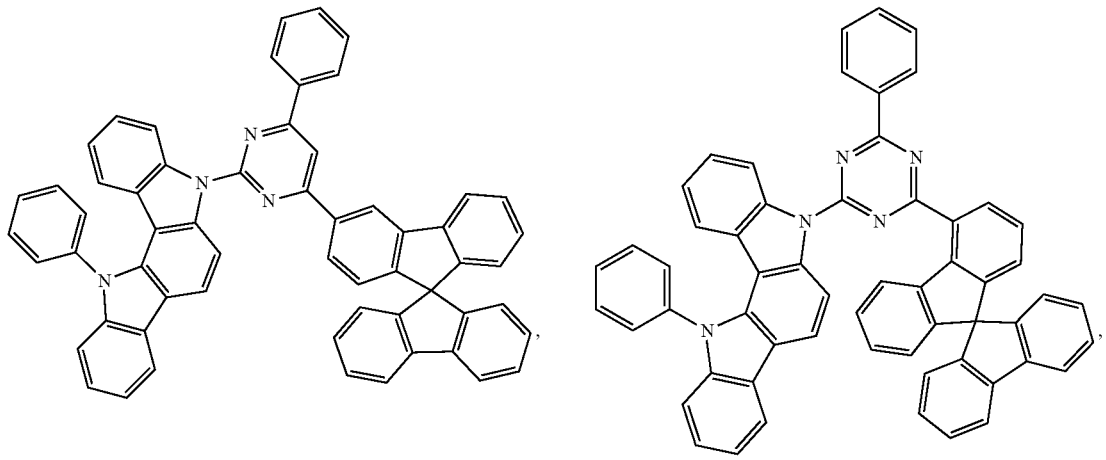
(7-6)
(7-7)
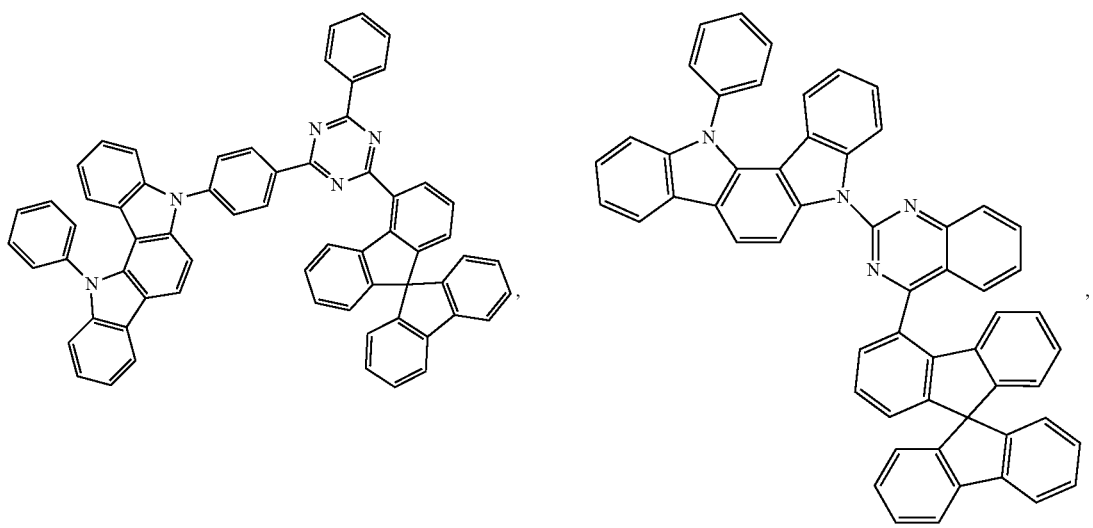
(7-8)
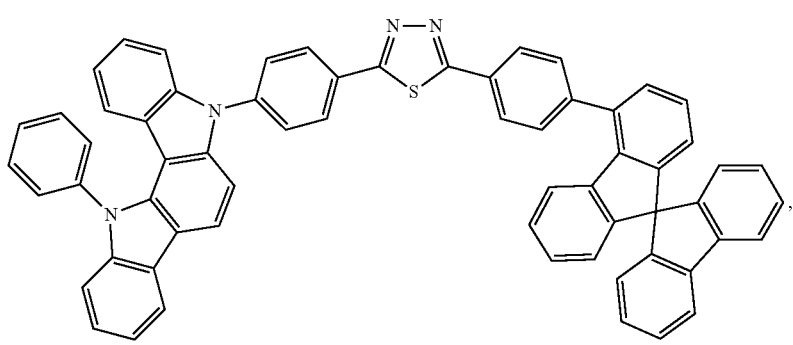

-continued
(7-9)
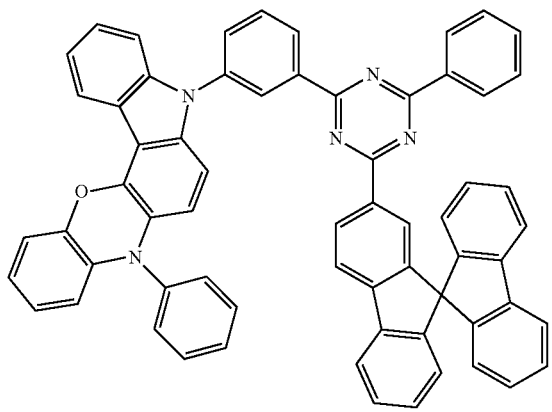
(7-10)
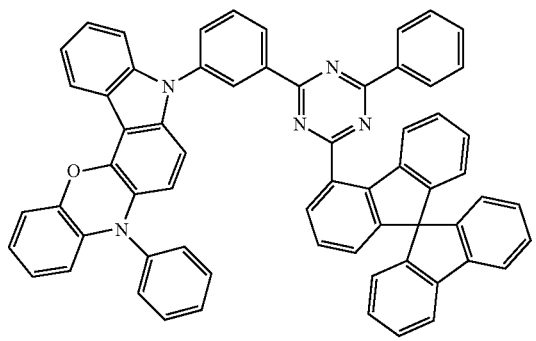
(7-11)
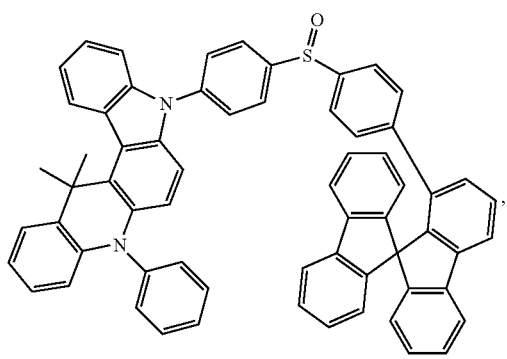
(7-12)
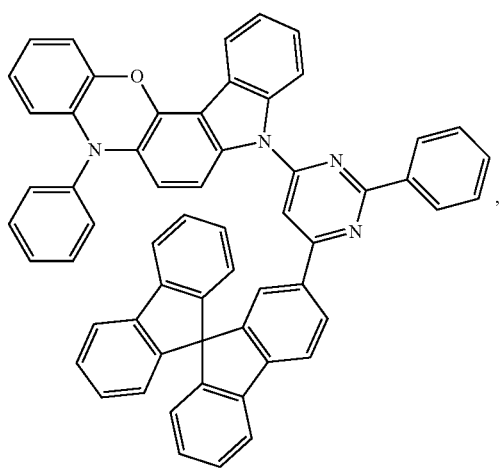
(7-13)
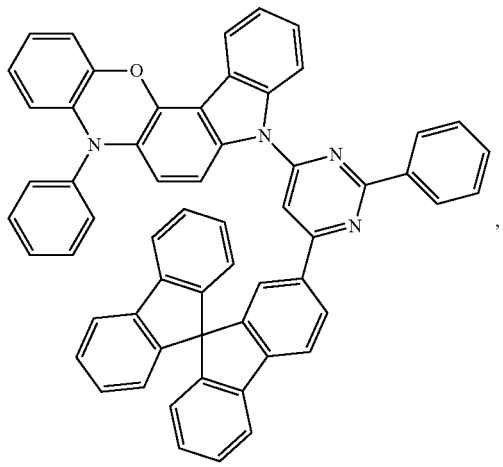
(7-14)
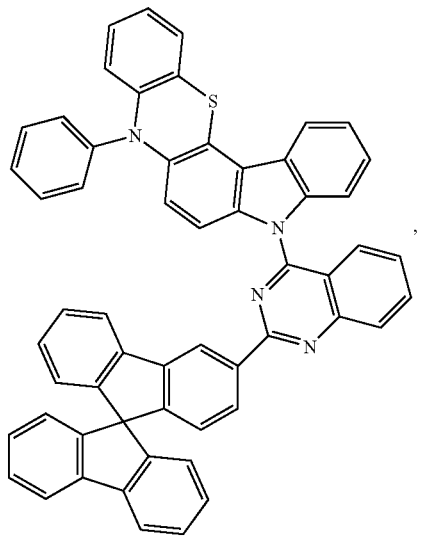

-continued
(7-15)
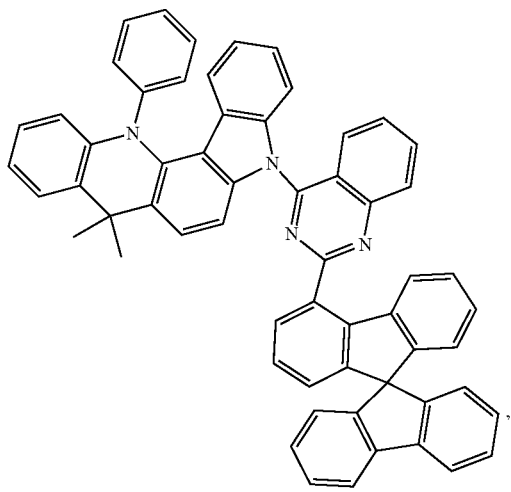
(7-16)
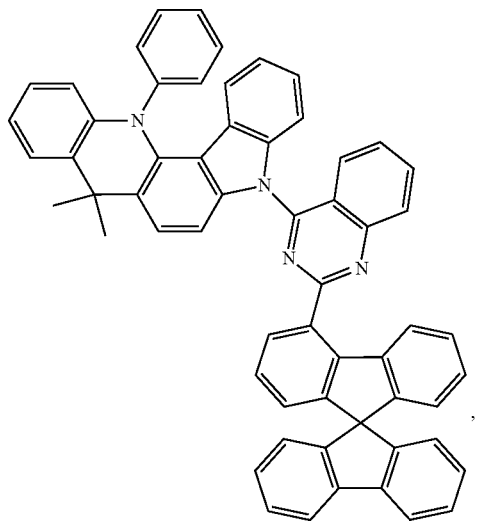
(7-17)
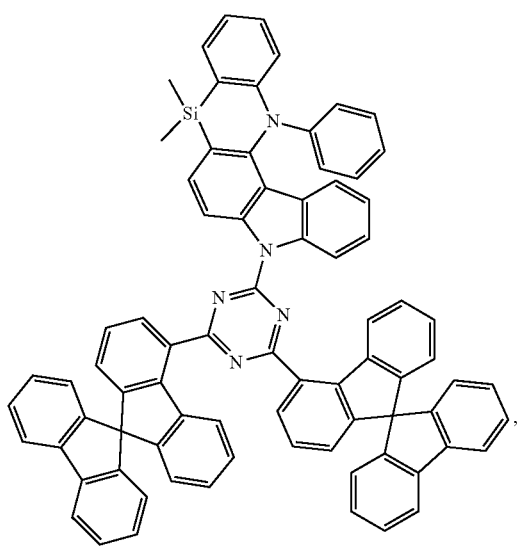
(7-18)
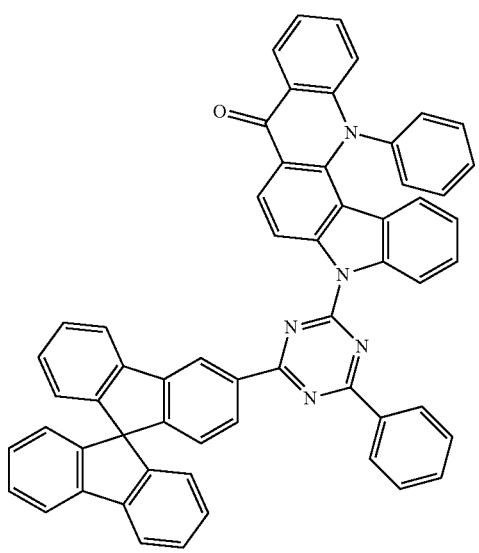
(8-1)
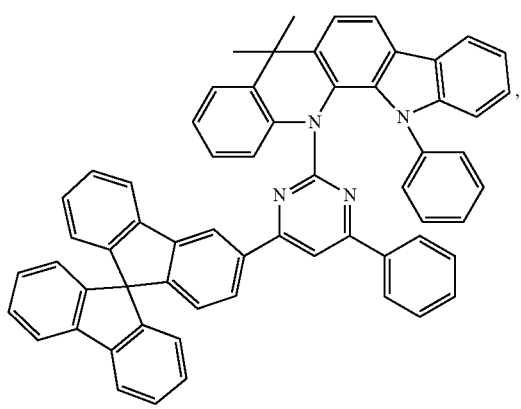
(8-2)
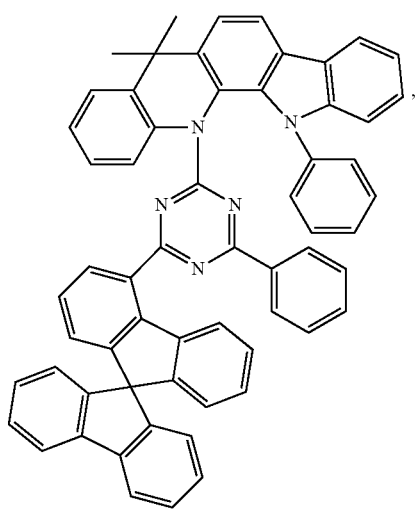

-continued
(8-3)
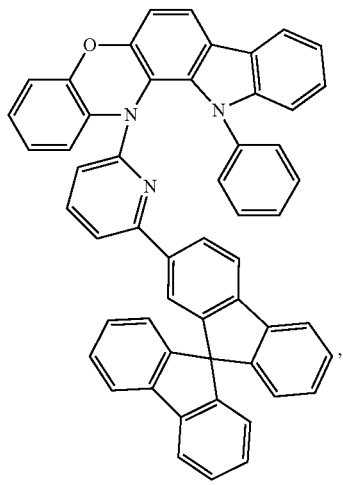
(8-4)
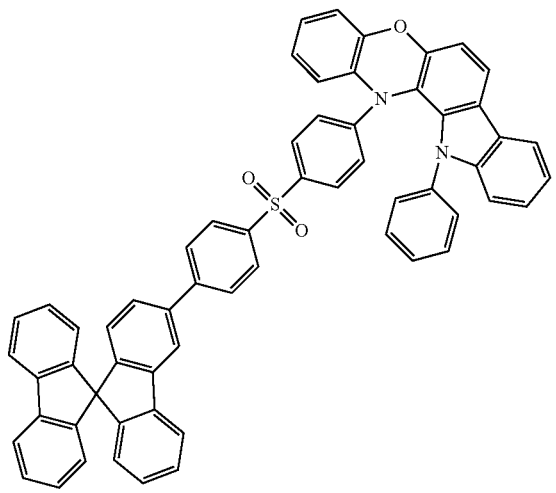
(8-5)
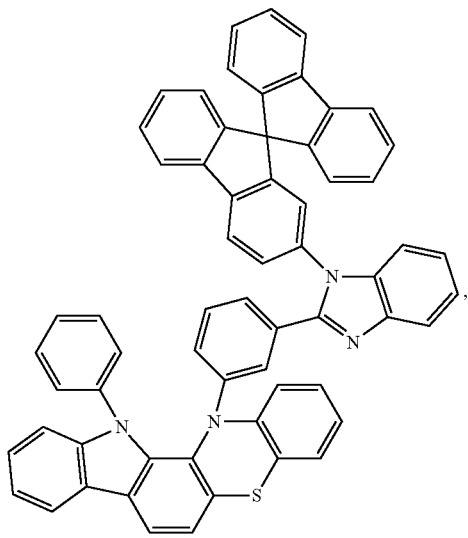
(8-6)
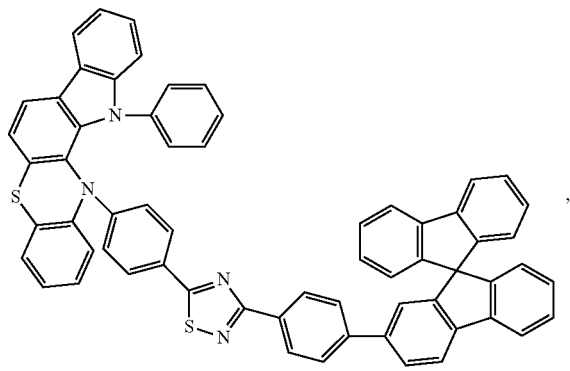
(8-7)
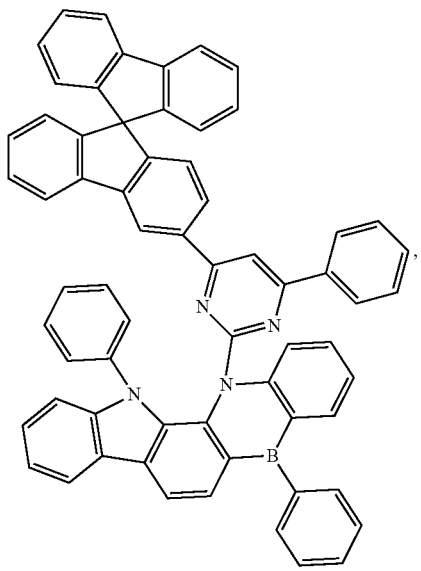
(8-8)
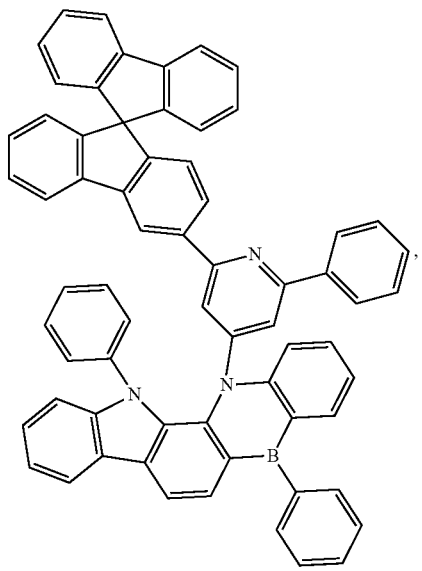

-continued
(8-9)
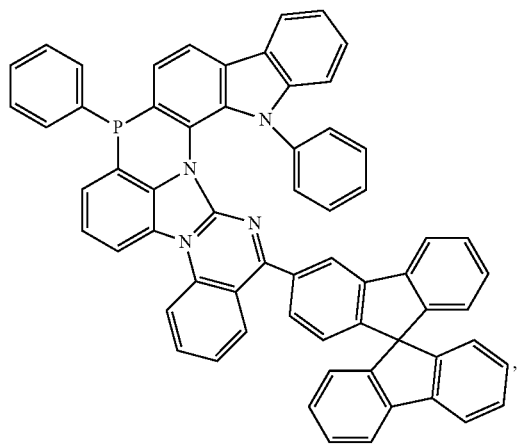
(8-10)
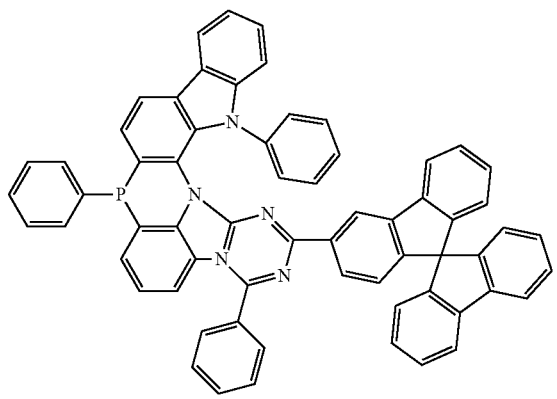
(8-11)
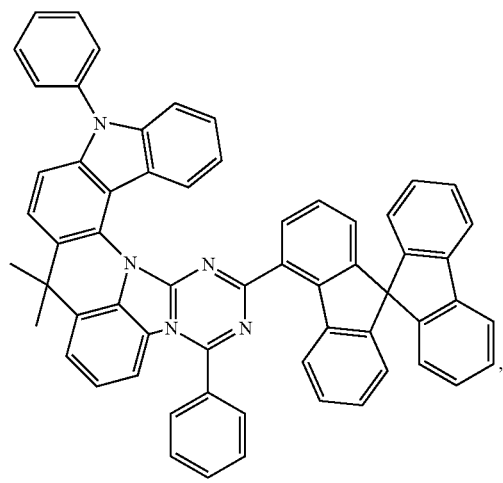
(8-12)
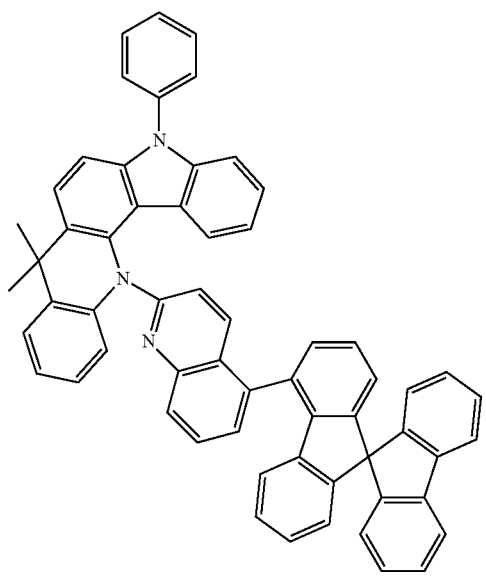
(8-13)
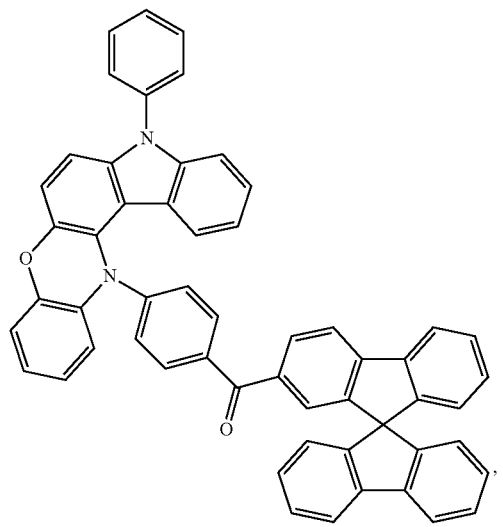
(8-14)
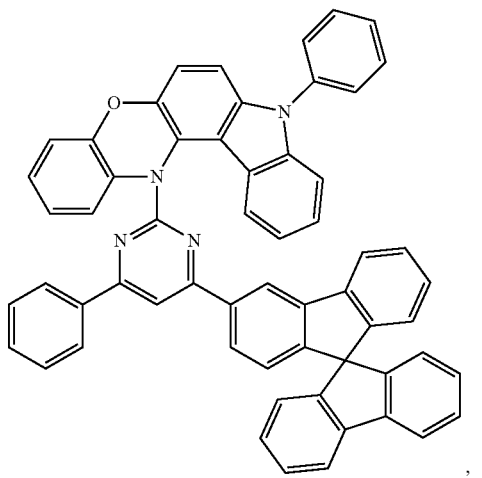

-continued
(8-15)
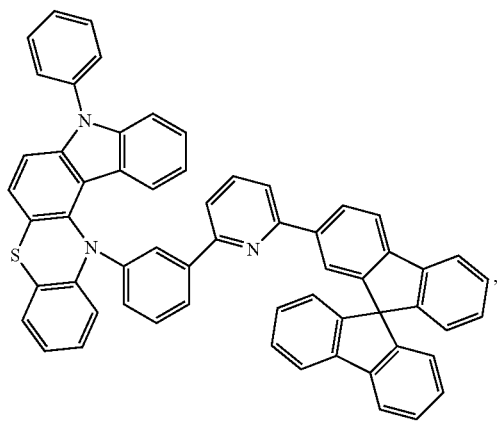
(8-16)
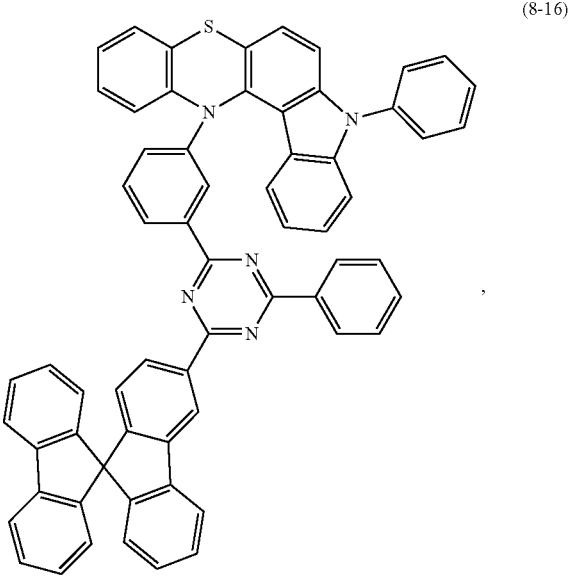
(8-17)
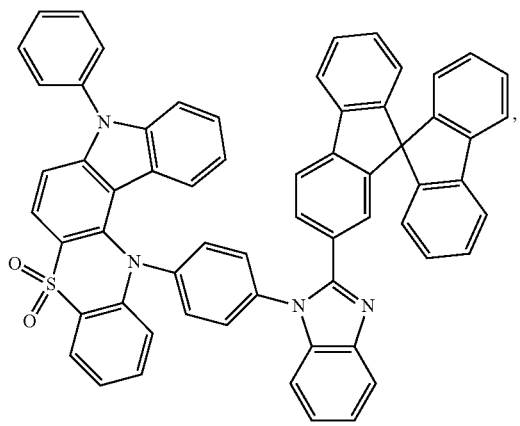
(8-18)
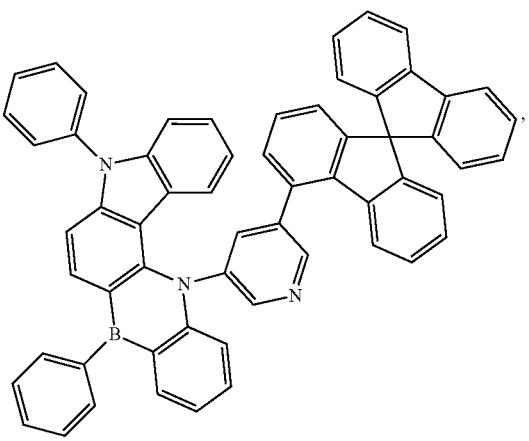
(8-19)
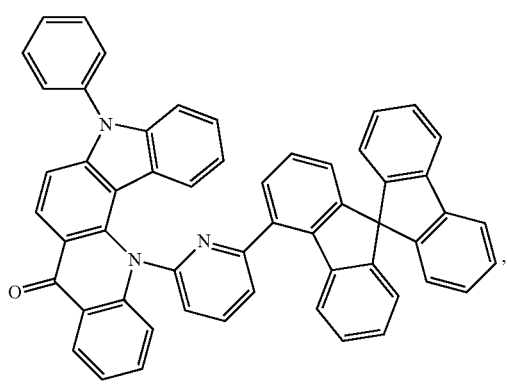
(9-1)
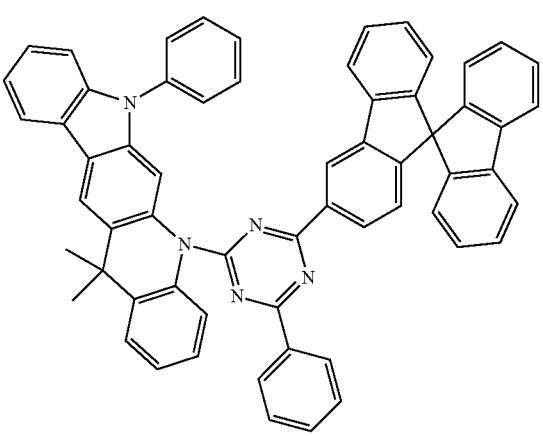

-continued
(9-2)
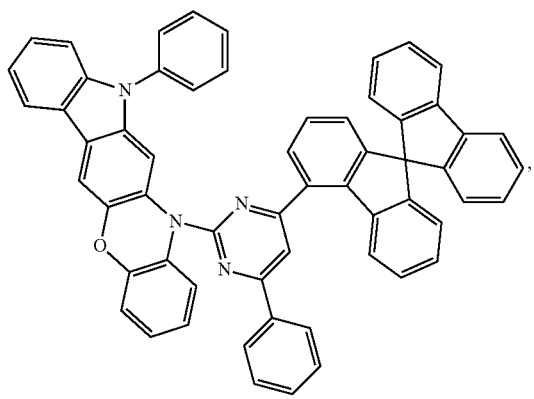
(9-3)
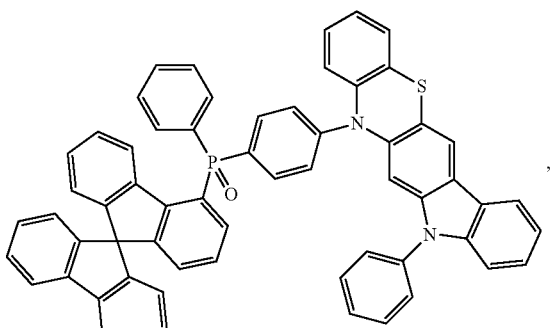
(9-4)
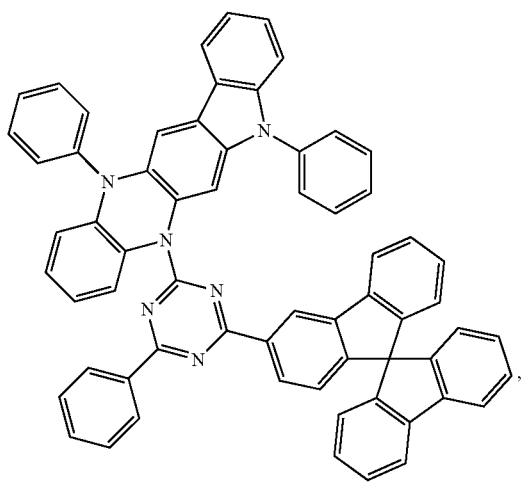
(9-5)
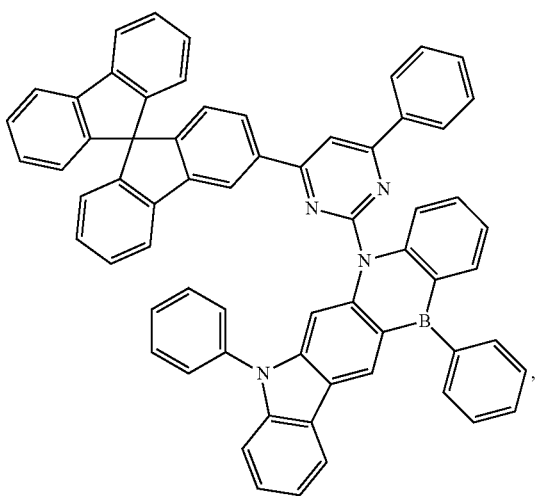
(9-6)
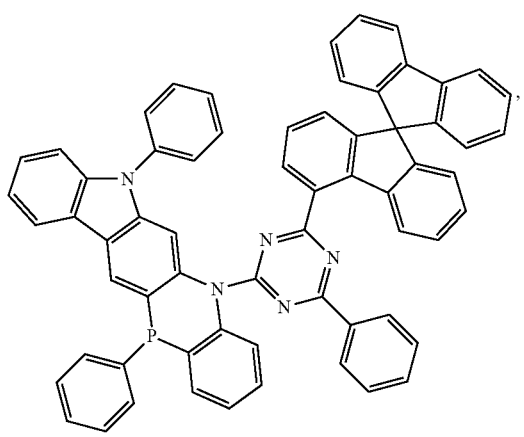
(9-7)
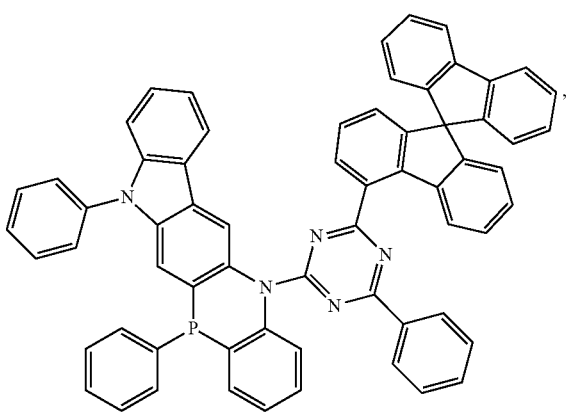

(9-8)
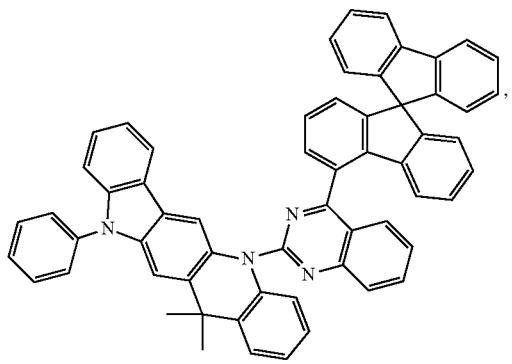
(9-9)
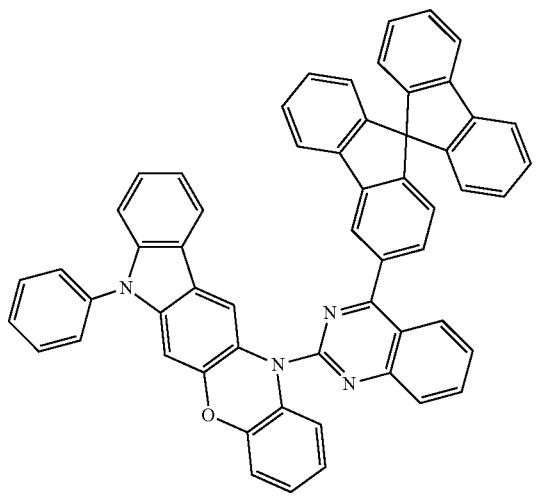
(9-10)
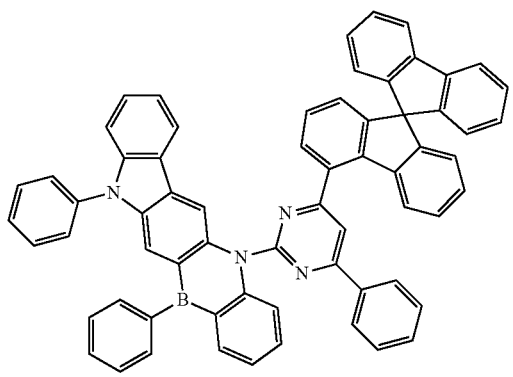
(9-11)
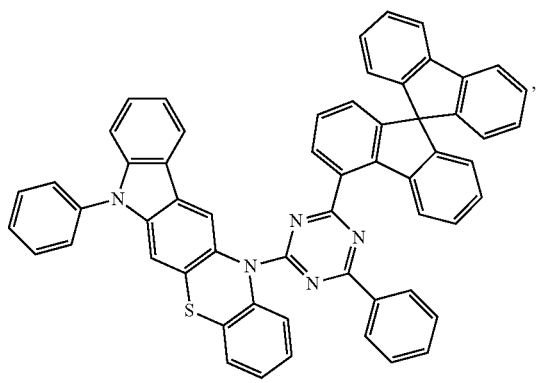
(9-12)
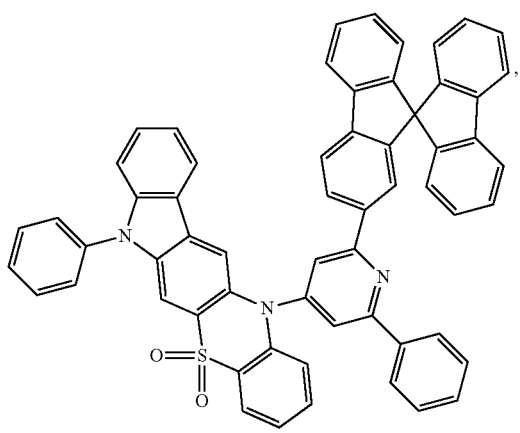
(10-1)
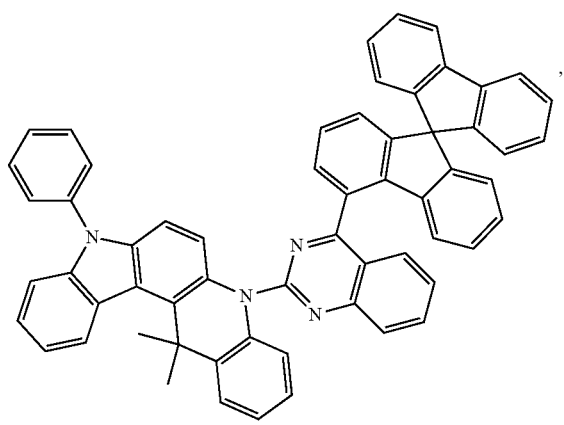

(10-2)
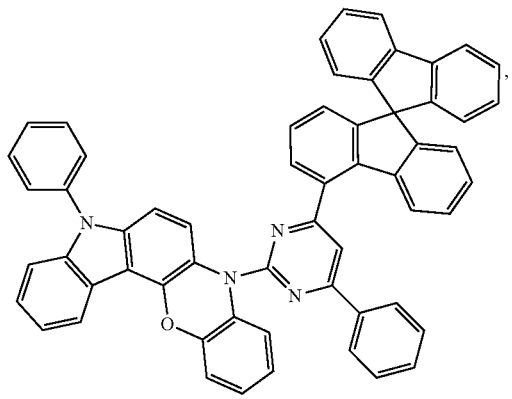
(10-3)
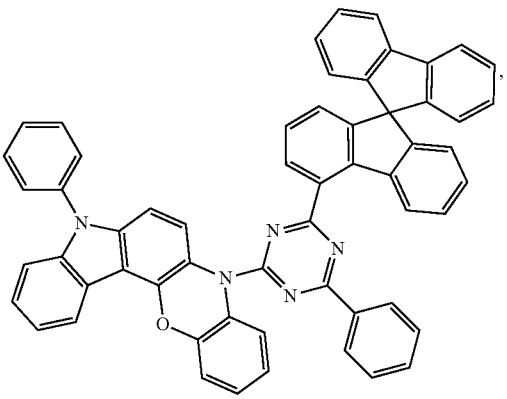
(10-4)
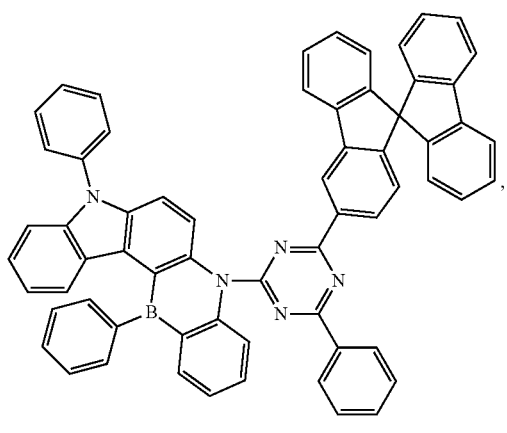
(10-5)
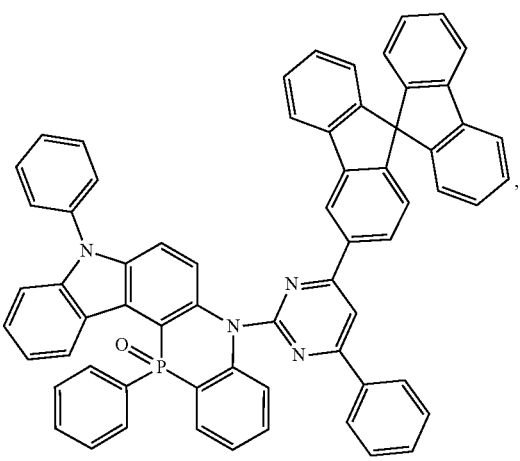
(10-6)
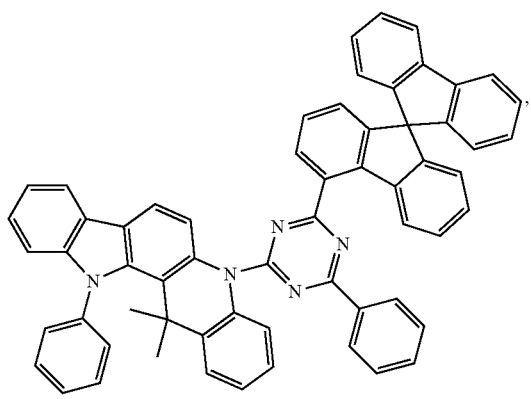
(10-7)
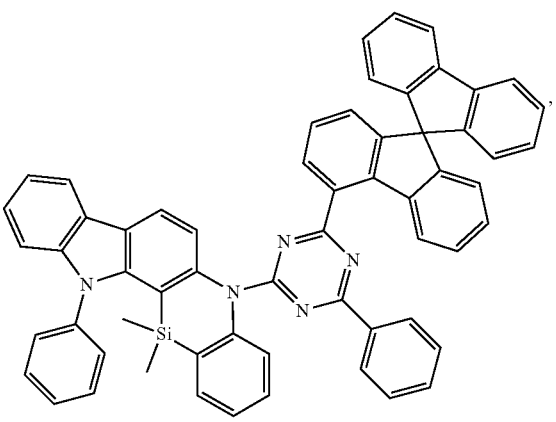

-continued
(10-8)
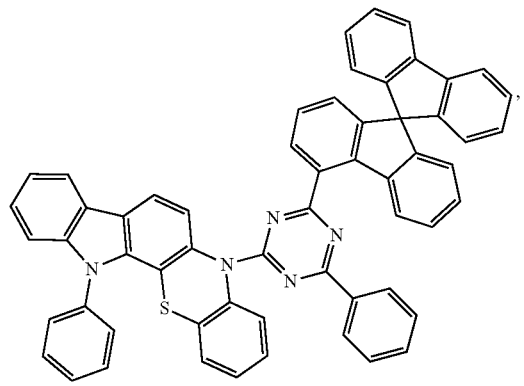
(10-9)
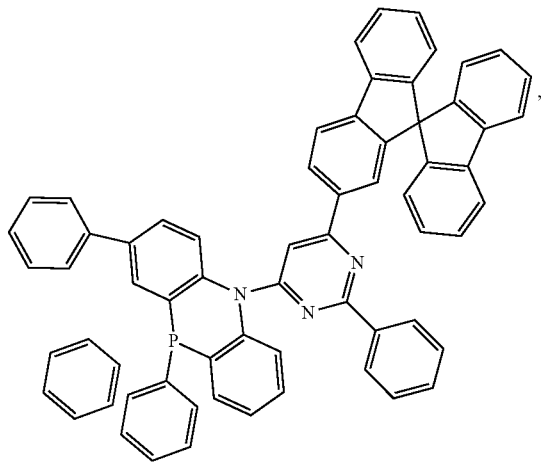
(10-10)
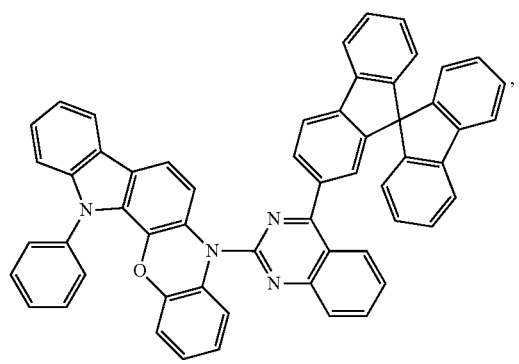
(11-1)
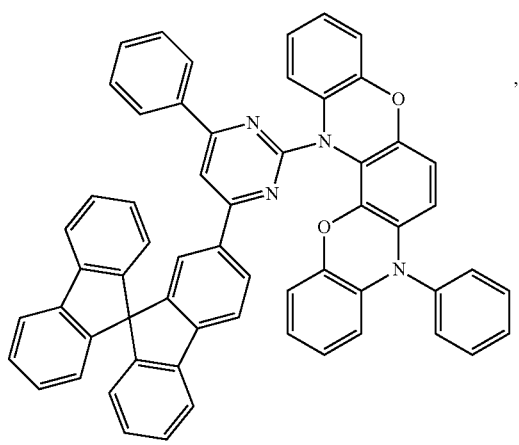
(11-2)
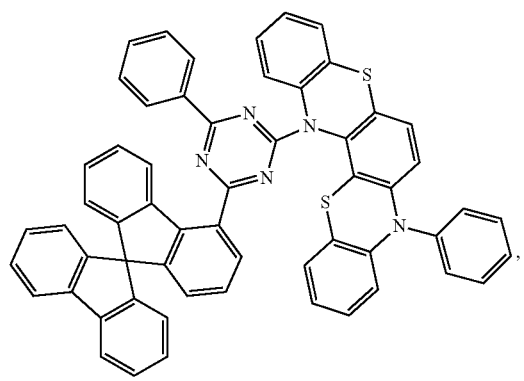
(11-3)
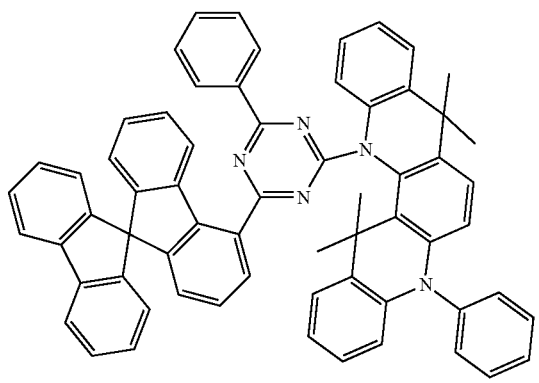

-continued
(11-4)
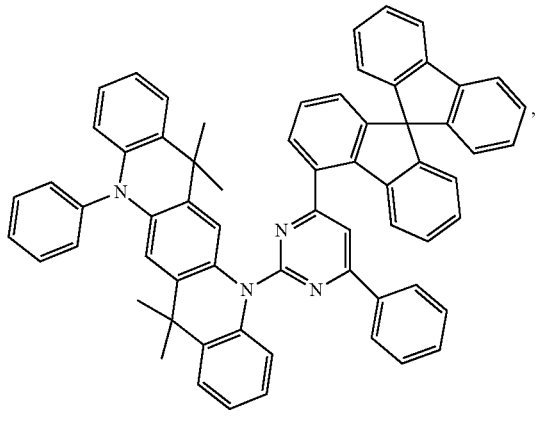
(11-5)
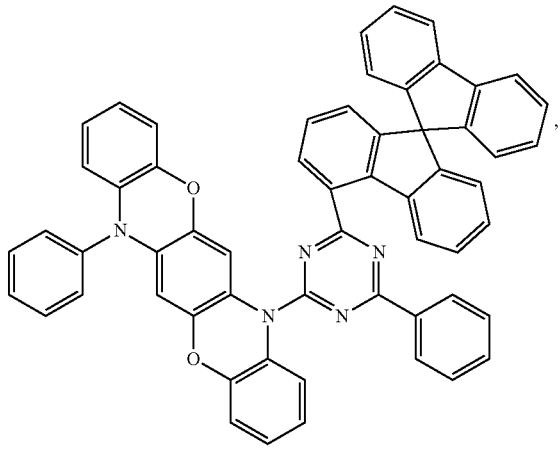
(11-6)
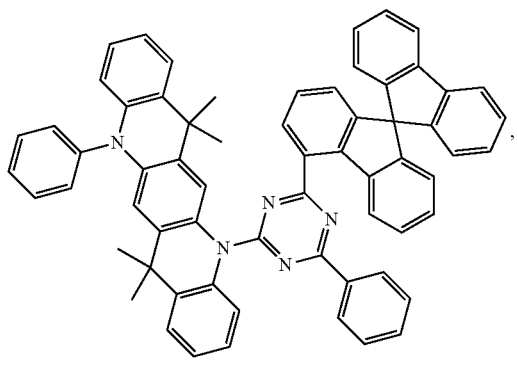
(11-7)
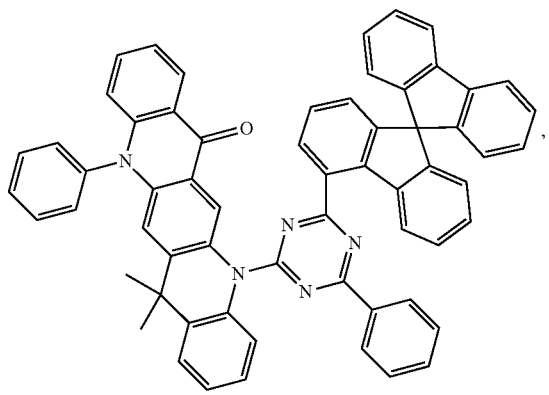
(11-8)
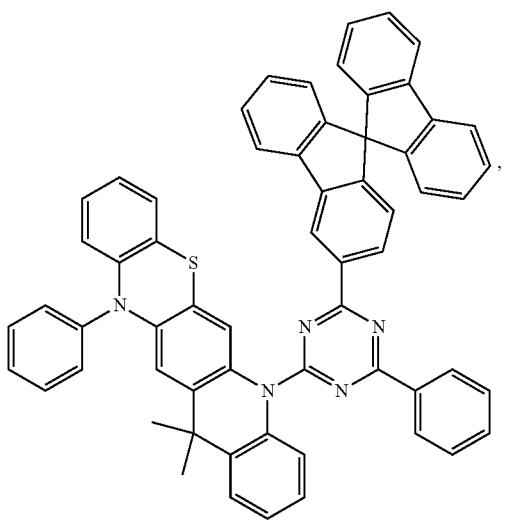
(11-9)
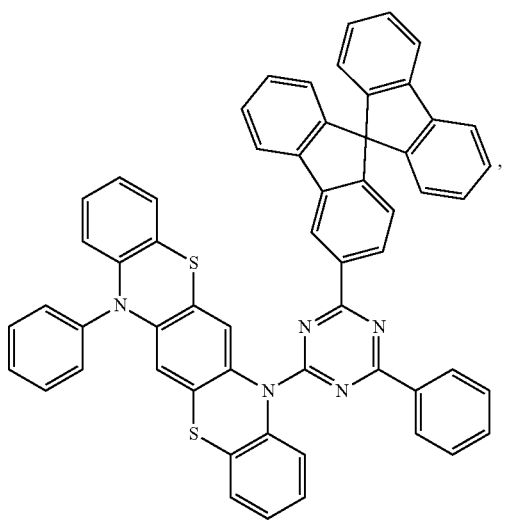

(11-10)
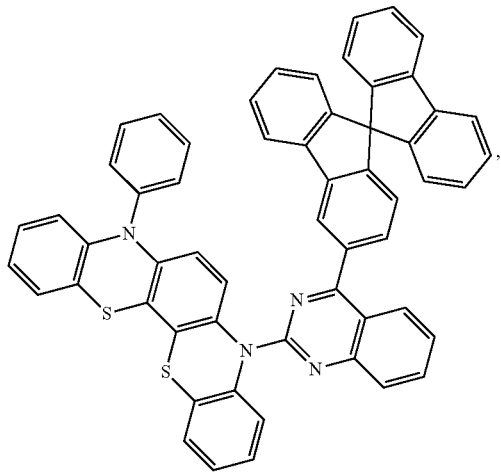
(11-11)
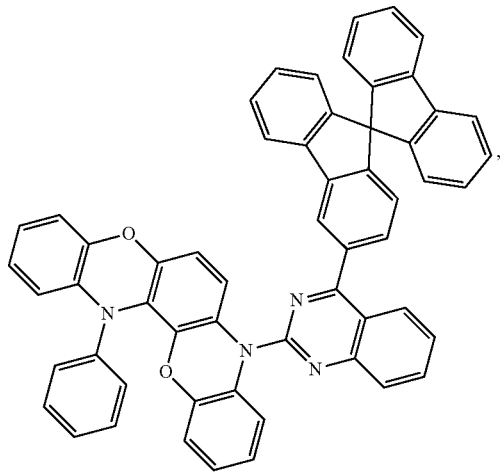
(11-12)
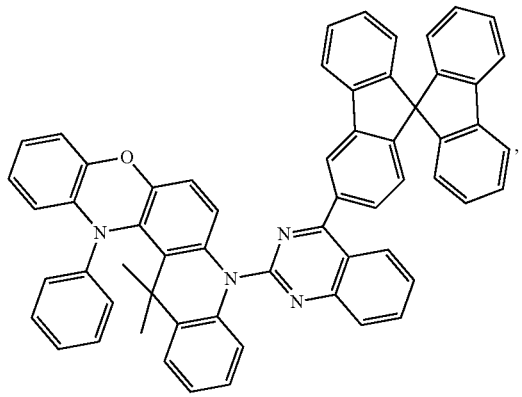
(12-1)
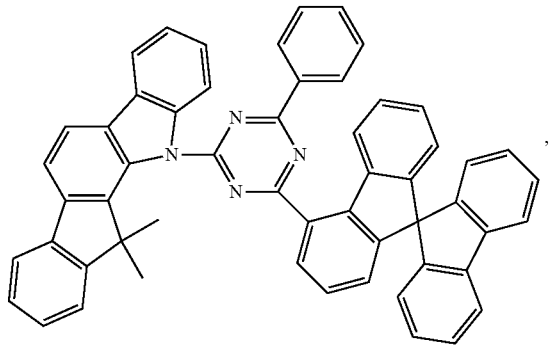
(12-2)
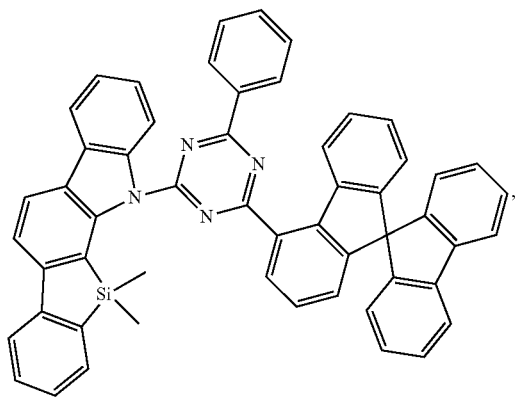
(12-3)
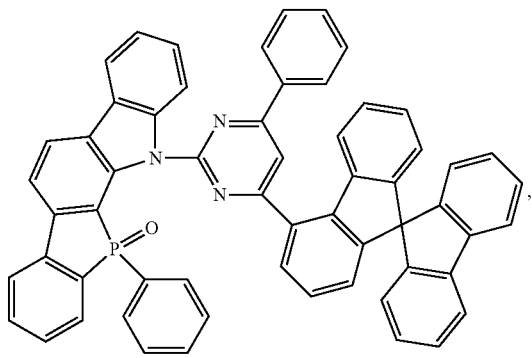

-continued
(12-4)
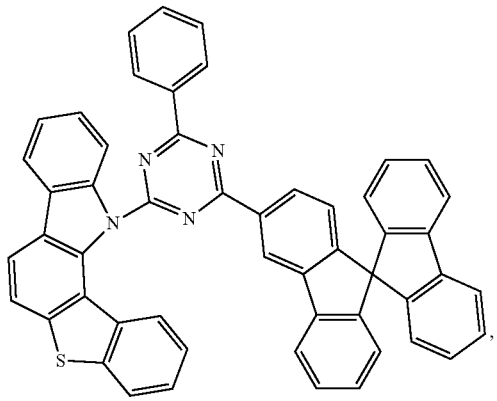
(12-5)
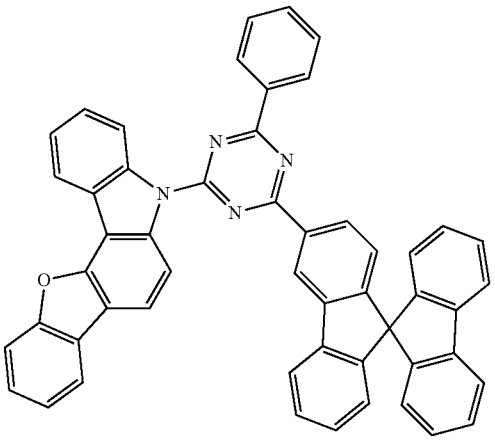
(12-6)
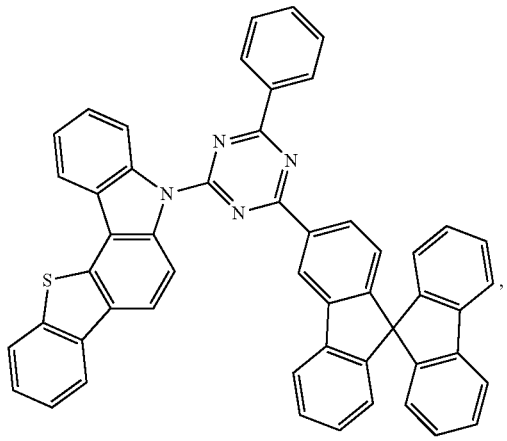
(12-7)
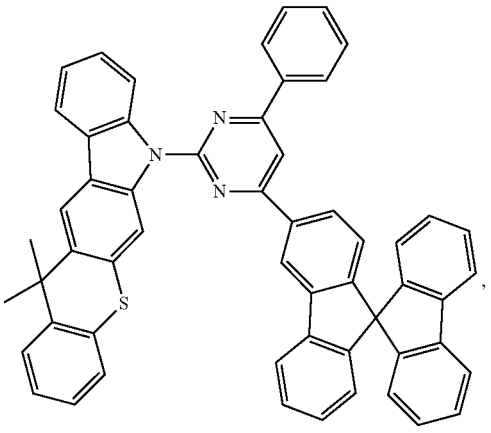
(12-8)
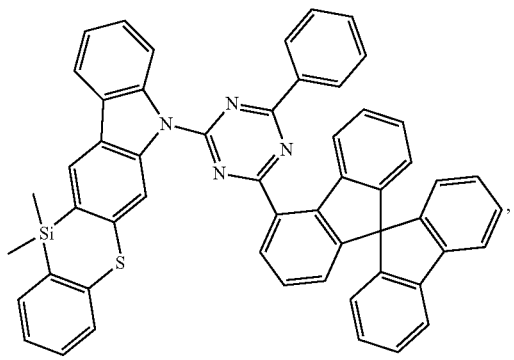
(12-9)
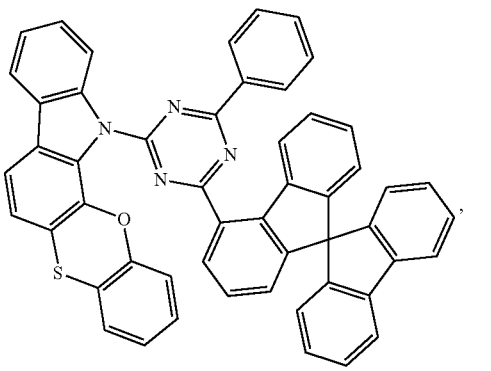
(12-10)
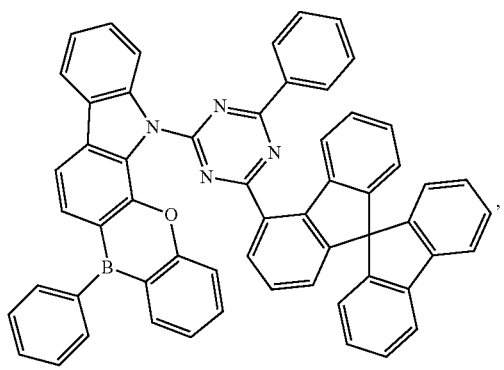
(12-11)
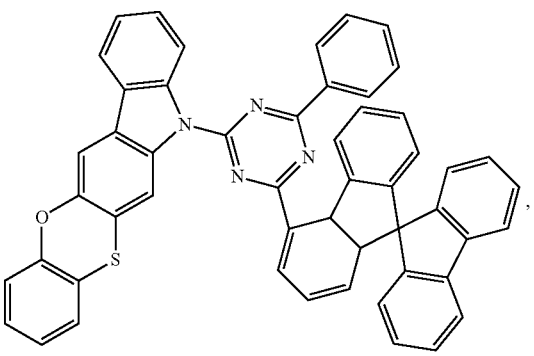

-continued
(12-12)
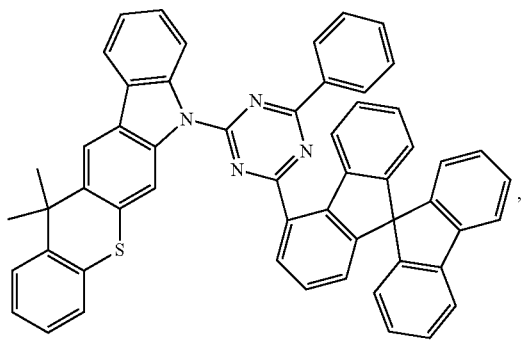
(12-13)
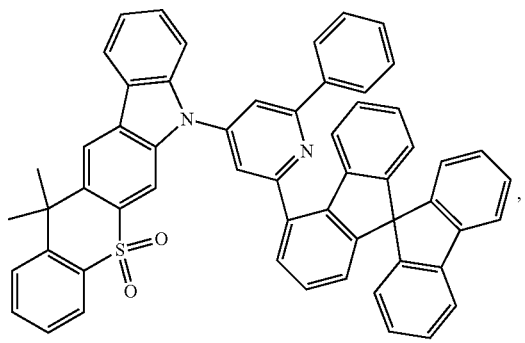
(12-14)
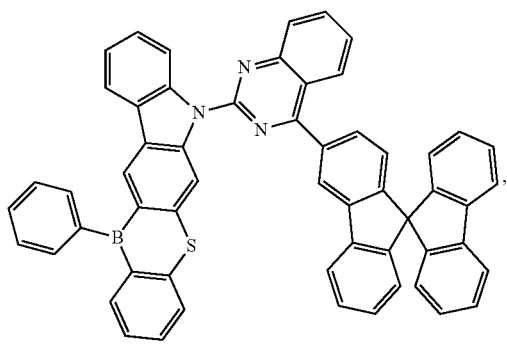
(12-15)
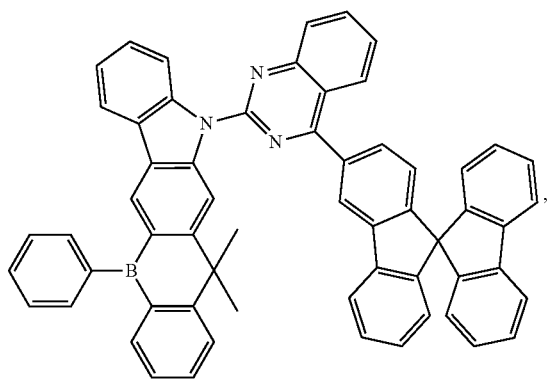
(12-16)
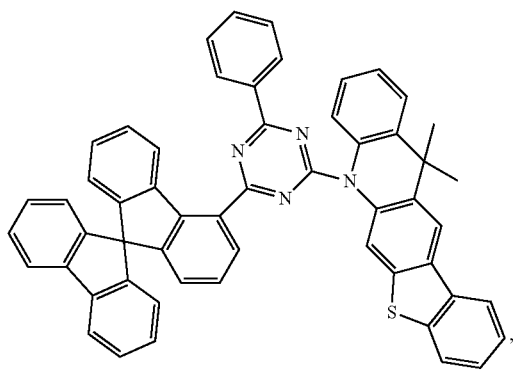
(12-17)
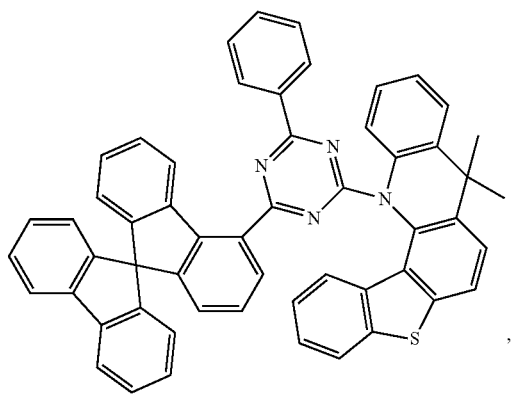
(12-18)
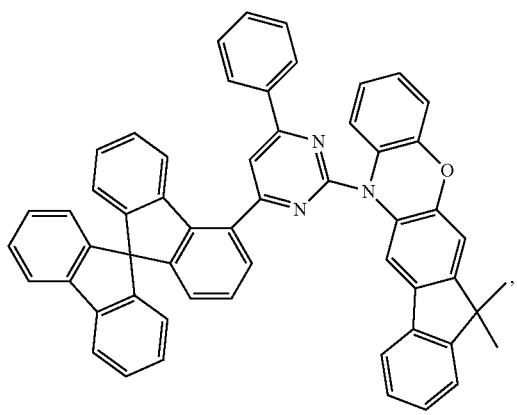
(12-19)
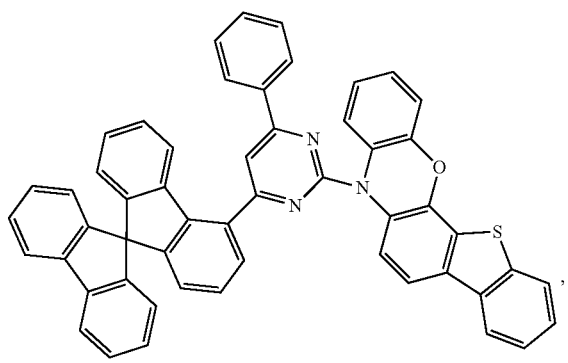

-continued
(12-20)
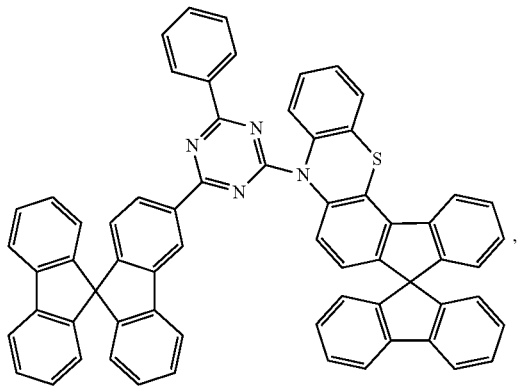
(12-21)
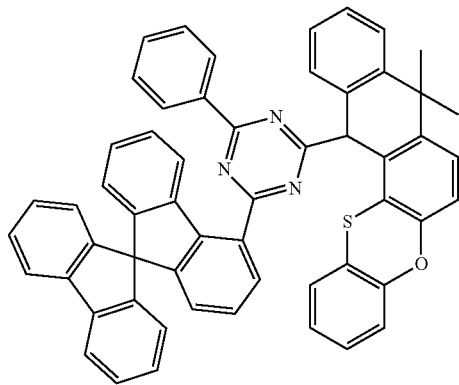
(12-22)
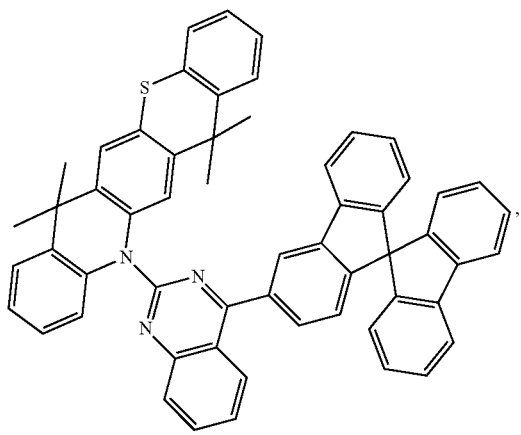
(12-23)
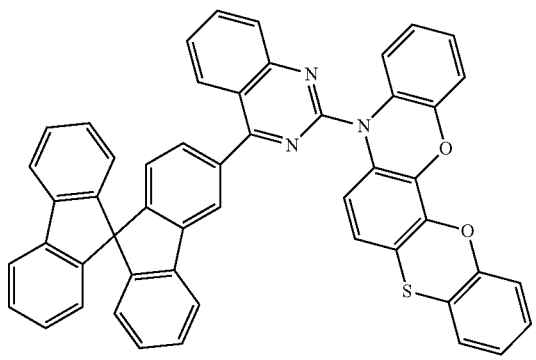
(13-1)
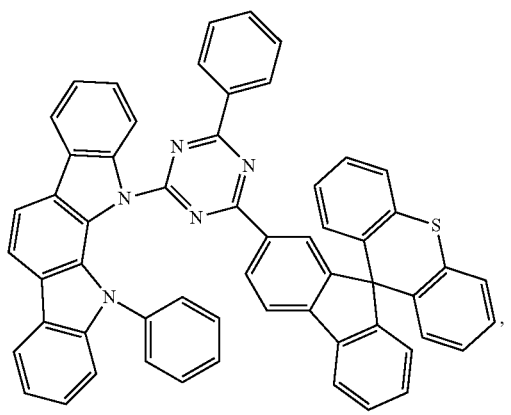
(13-2)
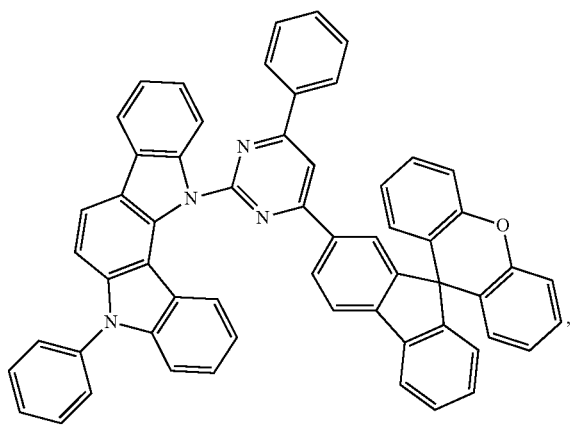

-continued
(13-3)
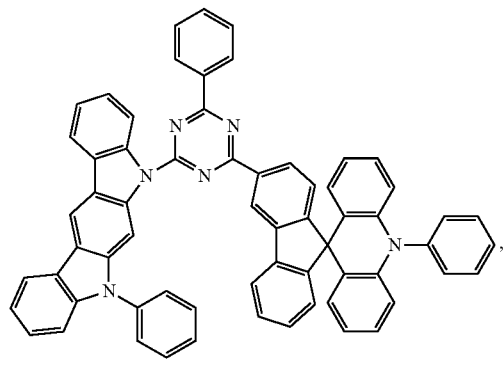
(13-4)
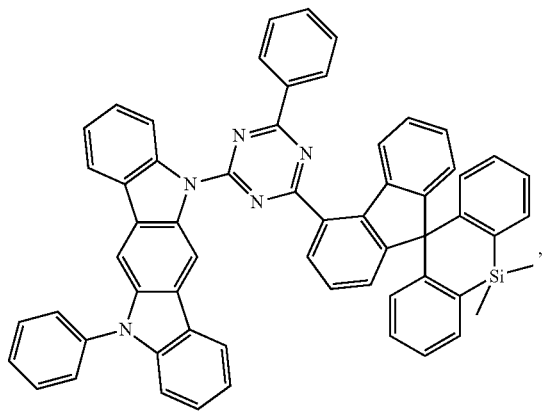
(13-5)
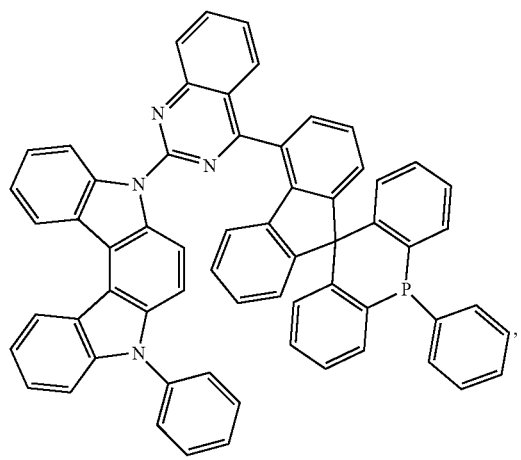
(13-6)
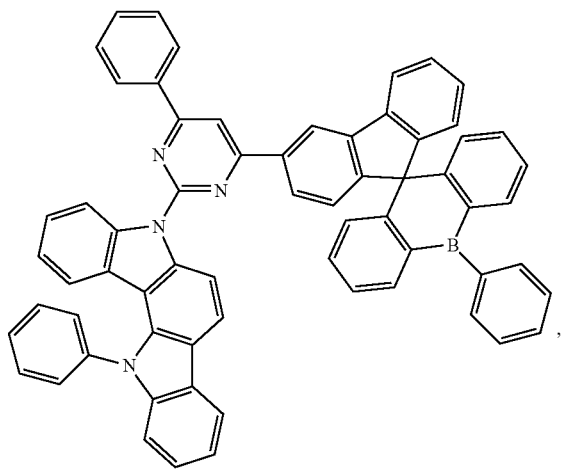
(13-7)
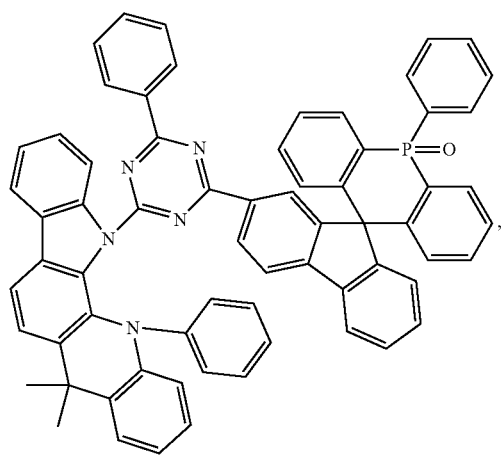
(13-8)
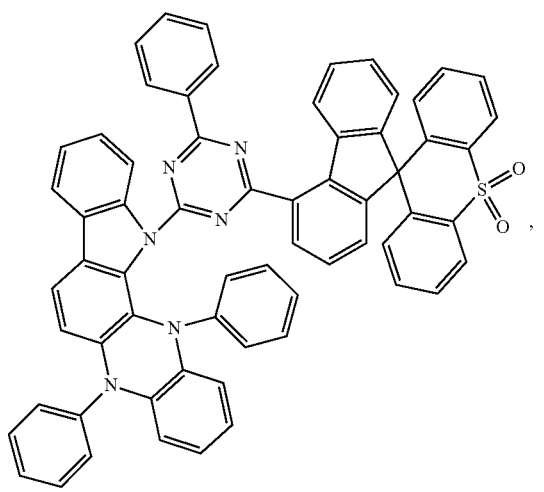

(13-9)
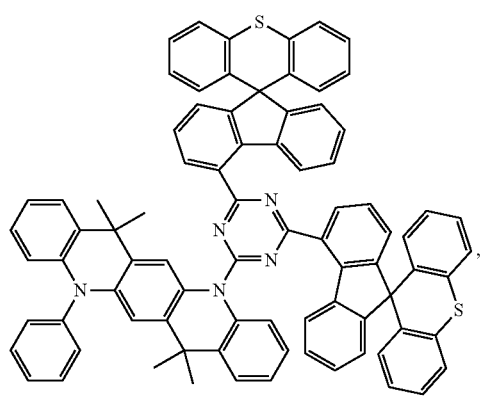
(14-1)
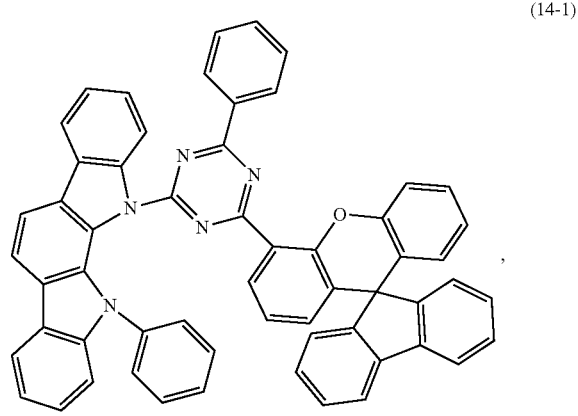
(14-2)
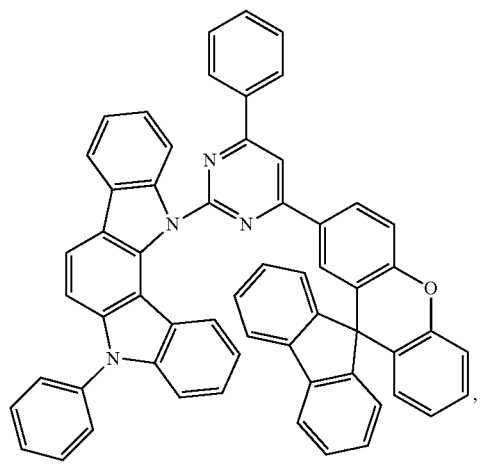
(14-3)
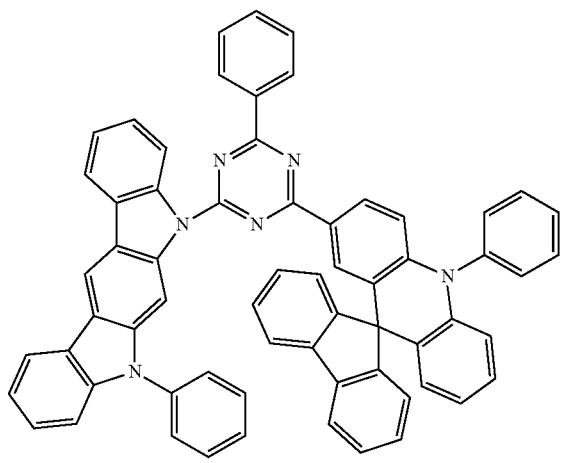
(14-4)
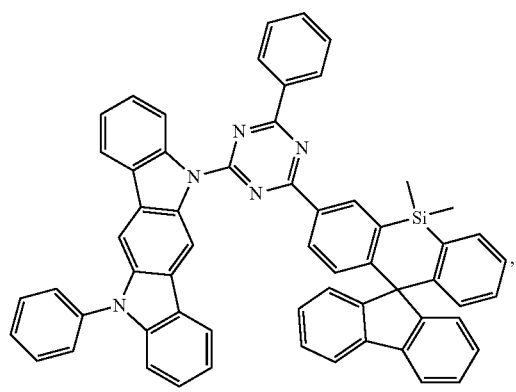
(14-5)
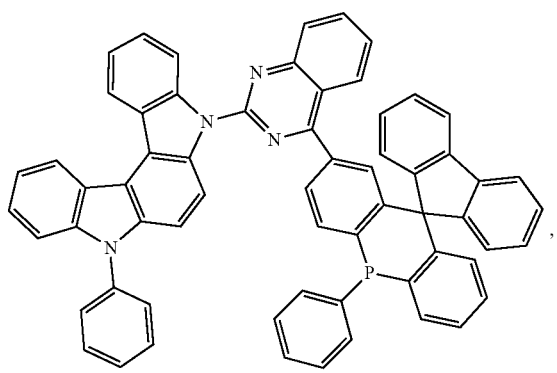

-continued
(14-6)
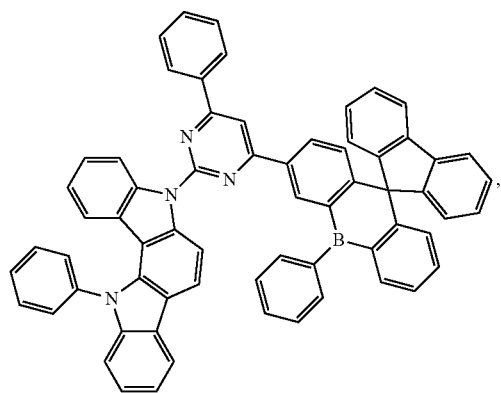
(14-7)
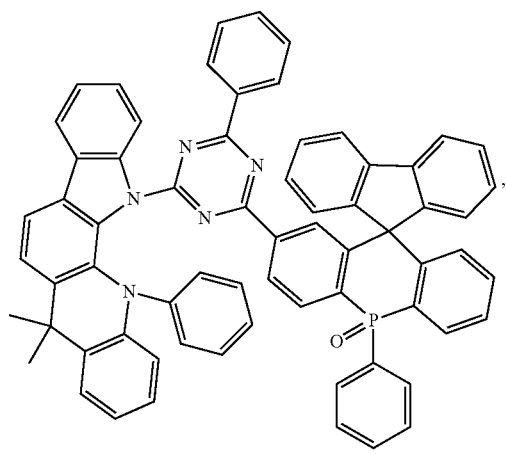
(14-8)
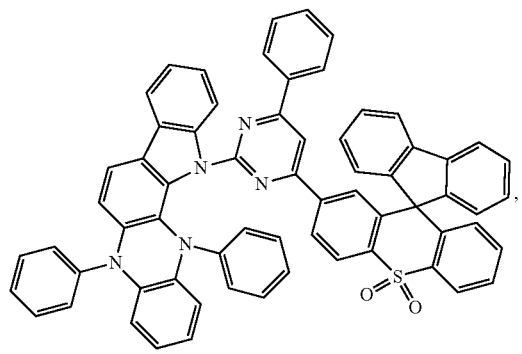
(14-9)
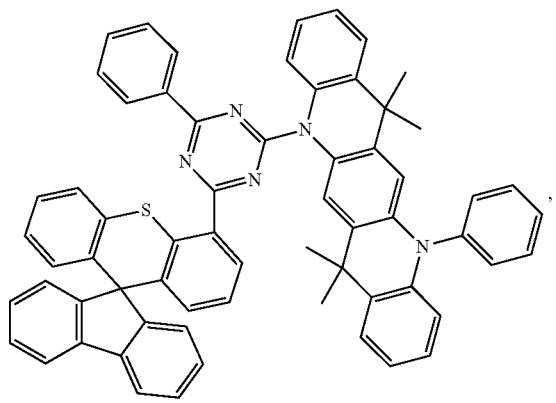
(15-1)
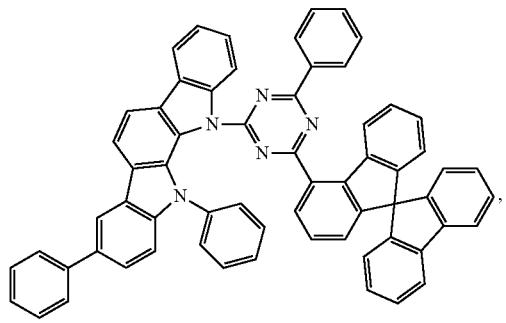
(15-2)
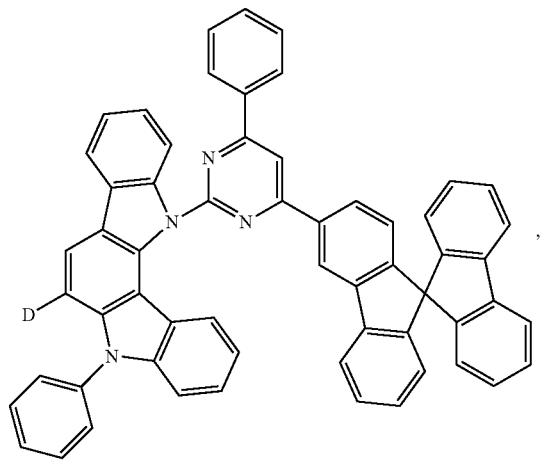

-continued (15-3)
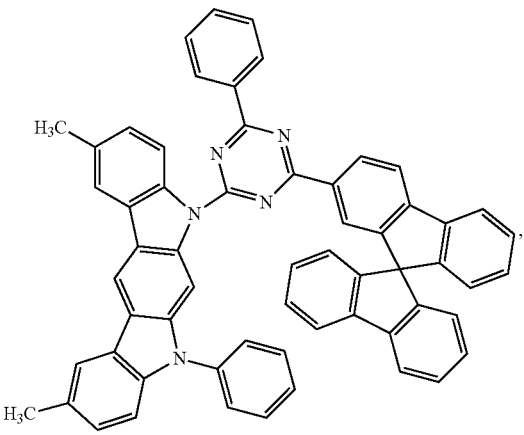

(15-4)
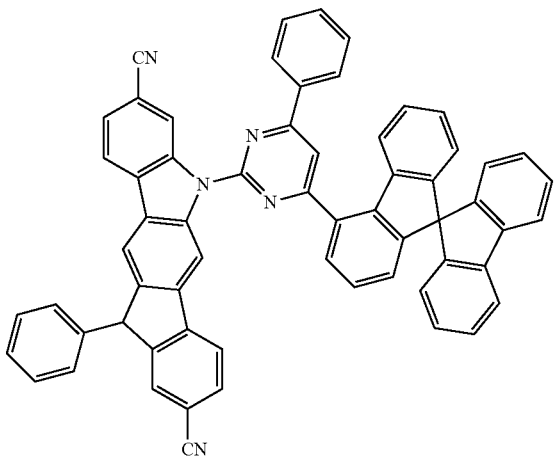

(15-5)
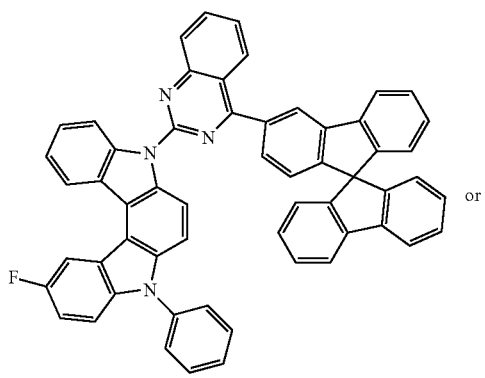

or (15-6)
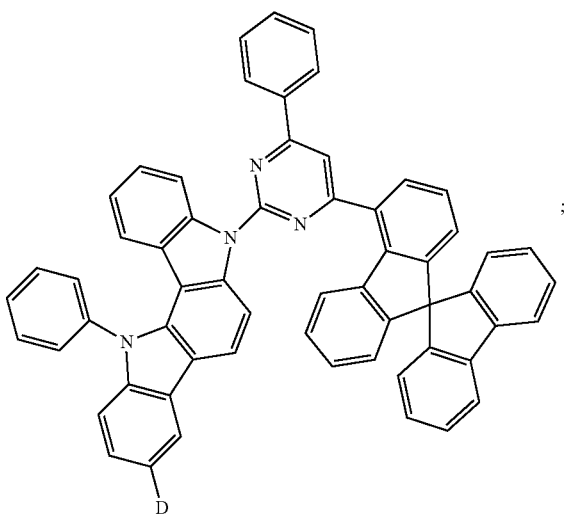

;

wherein the numbers in parentheses after each structural formula only represent the numbering of the compound of the formula, and have no other meaning. For example, (15-6) represents compound 15-6.

In one embodiment, the nitrogen-containing fused heterocyclic compound has a $T_g$ (glass transition temperature) greater than or equal to 100° C. A higher $T_g$ allows the compound to have a better thermal stability, thereby giving the compound greater scope of application.

In one embodiment, the nitrogen-containing fused heterocyclic compound has a $T_g$ greater than or equal to 120° C.

In one embodiment, the nitrogen-containing fused heterocyclic compound has a $T_g$ greater than or equal to 140° C.

In one embodiment, the nitrogen-containing fused heterocyclic compound has a $T_g$ greater than or equal to 160° C.

In one embodiment, the nitrogen-containing fused heterocyclic compound has a $T_g$ greater than or equal to 180° C.

In one embodiment, the nitrogen-containing fused heterocyclic compound can be used as a hole injection material (HIM), a hole transporting material (HTM), an electron transporting material (ETM), an electron injection material (EIM), an electron blocking material (EBM), a hole blocking material (HBM), an emitter and a host material (Host).

In one embodiment, the nitrogen-containing fused heterocyclic compound can be used as a host material, an electron transporting material, or a hole transporting material.

In one embodiment, the nitrogen-containing fused heterocyclic compound can be used as a phosphorescent host material.

In one embodiment, the nitrogen-containing fused heterocyclic compound is a small molecule compound, i.e., a molecule that is not a polymer, oligomer, dendrimer or copolymer.

In one embodiment, the nitrogen-containing fused heterocyclic compound is a small molecule compound having a molecular mass less than or equal to 3000 g/mol.

In one embodiment, the nitrogen-containing fused heterocyclic compound is a small molecule compound having a molecular mass less than or equal to 2000 g/mol.

In one embodiment, the nitrogen-containing fused heterocyclic compound is a small molecule compound having a molecular mass less than or equal to 1500 g/mol.

In one embodiment, the nitrogen-containing fused heterocyclic compound has a molecular mass less than or equal to 1100 g/mol. The nitrogen-containing fused heterocyclic compound has a molecular mass less than or equal to 1100 g/mol so that the compound can be used in evaporation-based OLEDs.

In one embodiment, the nitrogen-containing fused heterocyclic compound has a molecular mass less than or equal to 1000 g/mol.

In one embodiment, the nitrogen-containing fused heterocyclic compound has a molecular mass less than or equal to 900 g/mol.

In one embodiment, the nitrogen-containing fused heterocyclic compound has a molecular mass less than or equal to 800 g/mol.

In one embodiment, the nitrogen-containing fused heterocyclic compound has a molecular mass less than or equal to 750 g/mol.

In one embodiment, the nitrogen-containing fused heterocyclic compound has a molecular mass less than or equal to 700 g/mol. The nitrogen-containing fused heterocyclic compound has a molecular mass greater than or equal to 700 g/mol so that the compound can be used in the printed OLEDs.

In one embodiment, the nitrogen-containing fused heterocyclic compound has a molecular mass greater than or equal to 900 g/mol.

In one embodiment, the nitrogen-containing fused heterocyclic compound has a molecular mass greater than or equal to 950 g/mol.

In one embodiment, the nitrogen-containing fused heterocyclic compound has a molecular mass greater than or equal to 1000 g/mol.

In one embodiment, the nitrogen-containing fused heterocyclic compound has a solubility in toluene of 10 mg/mL at 25° C.

In one embodiment, the nitrogen-containing fused heterocyclic compound has a solubility in toluene of 15 mg/mL at 25° C.

In one embodiment, the nitrogen-containing fused heterocyclic compound has a solubility in toluene of 20 mg/mL at 25° C.

The nitrogen-containing fused heterocyclic compound of one embodiment has at least the following advantages:

(1) a spiro group is introduced into the formula of the foregoing nitrogen-containing fused heterocyclic compound. The spiro group has a vertical spatial structure and has a good solubility, stability and optoelectronic property, thus it can enhance the solubility, stability and optoelectronic property of the nitrogen-containing fused heterocyclic compound. Meanwhile, the direct connection between the spiro group and the electron-accepting group can effectively avoid the close packing of the electron-accepting group and reduce the exciton quenching, thereby improving the stability of the nitrogen-containing fused heterocyclic compound, and further improving the stability and lifetime of materials and devices including the nitrogen-containing fused heterocyclic compounds.

(2) the foregoing nitrogen-containing fused heterocyclic compound has a $T_1$ greater than or equal to 2.0 eV and a $\Delta E_{ST}$ less than or equal to 0.30 eV. The sufficiently small $\Delta E_{ST}$ allows the compound to have the characteristics of a TADF material, i.e., triplet excitons can be converted to singlet excitons by internal reversion, thereby achieving efficient luminescence.

(3) the nitrogen-containing fused heterocyclic compound has a $T_g$ greater than or equal to 100° C. A higher $T_g$ allows the compound to have a better thermal stability, which thereby gives the compound greater scope of application.

(4) the foregoing nitrogen-containing fused heterocyclic compound can be used as a hole injection material, a hole transporting material, an electron transporting material, an electron injection material, an electron blocking material, a hole blocking material, an emitter or a host material, and has a broad range of applications.

The nitrogen-containing fused heterocyclic compound of one embodiment includes a repeating unit which includes the foregoing nitrogen-containing fused heterocyclic compound.

In one embodiment, the nitrogen-containing fused heterocyclic polymer is a homopolymer, i.e., the polymer is polymerized by only one repeating unit; wherein the repeating unit includes the foregoing nitrogen-containing fused heterocyclic compound.

In one embodiment, the nitrogen-containing fused heterocyclic polymer is a copolymer, i.e., the polymer is polymerized by two or more repeating units.

In one embodiment, the nitrogen-containing fused heterocyclic polymer is a copolymer obtained by polymerizing two repeating units one of which is a group of the foregoing nitrogen-containing fused heterocyclic structure and the other of which is an aromatic cyclic group or a heteroaromatic ring group.

In one embodiment, the nitrogen-containing fused heterocyclic polymer is a block copolymer, i.e., the polymer is formed by linking two or more polymer segments having different properties.

In one embodiment, the nitrogen-containing fused heterocyclic polymer is a block copolymer formed by linking two polymer segments of different properties one of which comprises the foregoing nitrogen-containing heterocyclic structure and the other is composed of another aromatic ring group or another heteroaromatic ring group.

In one embodiment, the nitrogen-containing fused heterocyclic polymer is a dendrimer.

In one embodiment, the nitrogen-containing fused heterocyclic polymer has at least one repeating unit. And, it should be noted that the number of repeating units can be set as needed.

In one embodiment, the nitrogen-containing fused heterocyclic polymer is a conjugated polymer, i.e., the main chain of the polymer is formed mainly by sp2 hybrid orbitals of C atoms. And, it should be noted that when the C atoms in the main chain of the polymer is substituted by other non-C atoms or the sp2 hybridization of the main chain is interrupted by some natural defects, the polymer is still considered to be a conjugated polymer. Meanwhile, when the main chain of the polymer includes an aryl amine, an aryl phosphine, other heteroaromatics, organometallic complexes and the like, the polymer is still considered to a conjugated polymer.

In one embodiment, the nitrogen-containing fused heterocyclic polymer is a non-conjugated polymer, and the foregoing nitrogen-containing fused heterocyclic compound is located on the side chain of the polymer.

The nitrogen-containing fused heterocyclic polymer of one embodiment has at least the following advantages:

The foregoing nitrogen-containing fused heterocyclic polymer including the foregoing nitrogen-containing fused heterocyclic compound has a good solubility, stability and optoelectronic property, and can be used as a hole injection material, a hole transporting material, an electron transporting material, an electron injection material, an electron blocking material, a hole blocking material, an emitter and a host material, and has a wide range of applications, and materials and devices including the nitrogen-containing fused heterocyclic polymer have a good stability and a long lifetime.

An organic electroluminescent material of one embodiment includes the foregoing nitrogen-containing fused heterocyclic compound or the foregoing nitrogen-containing fused heterocyclic polymer, and an organic functional material.

In one embodiment, said organic functional material is one selected from the group consisting of a hole injection material, a hole transporting material, an electron injection material, an electron transporting material, a hole blocking material, an electron blocking material, a host material, a singlet emitter, and a thermally activated delayed fluorescent material, a triplet emitter, a host material and an organic dye. Among them, various organic functional materials are described in detail in WO 2010135519A1, US 20090134784A1 and WO 2011110277A1, and the organic functional materials in these three patents can be used as organic functional materials in the organic electroluminescent materials in the present embodiment.

Singlet emitters, also known as fluorescent emitters, usually have a larger conjugated π-electron system.

In one embodiment, styrylamine and derivates thereof disclosed in JP 2913116B and WO 2001021729A1 can be used as organic functional materials of the present embodiment.

In one embodiment, indenofluorene and derivates thereof disclosed in WO 2008/006449 and WO 2007/140847 can be used as organic functional materials of the present embodiment.

In one embodiment, indenofluorene-amine and indenofluorene-diamine disclosed in WO 2006/122630, benzoindenofluorene-amine and benzoindenofluorene-diamine disclosed in WO 2008/006449 and dibenzoindenofluorene-amine and dibenzoindenofluorene-diamine disclosed in WO2007/140847 can be used as organic functional materials of the present embodiment.

In one embodiment, the singlet emitter is one selected from the group consisting of an aryl amine, a styrylphosphine, a styryl ether, a monostyrylamine, a distyrylamine, a tristyrylamine, and a tetrastyrylamine.

In one embodiment, an aryl amine is a compound in which three unsubstituted or substituted aromatic ring groups or heteroaromatic ring groups are directly bonded to a nitrogen, and at least one of the three aromatic ring groups or the heteroaromatic ring groups contains a fused ring, wherein the heteroatom in the heteroaromatic ring group is N, O or S.

In one embodiment, when the aryl amine is a compound in which three substituted aromatic ring groups or heteroaromatic ring groups are directly bonded to a nitrogen, the substituted aromatic ring group or heteroaromatic ring group is benzene, biphenyl, naphthalene, anthracene, phenanthrene, fluorene, carbazole, benzofuran or benzothiophene.

In one embodiment, the aromatic ring of the aryl amine has atoms greater than or equal to 14.

In one embodiment, the aryl amine is an aryl anthramine, an aryl anthradiamine, an aryl pyrene diamine, an aryl chrysene amine or an aryl chrysene diamine.

In one embodiment, when a styrylphosphine is a compound containing one substituted styryl group and at least one phosphino group, the substituent is benzene, biphenyl, naphthalene, anthracene, phenanthrene, fluorene, carbazole, benzofuran or benzothiophene.

In one embodiment, the styryl group in the styrylphosphine is a distyryl group.

In one embodiment, a styryl ether is a compound containing one unsubstituted or substituted styryl group and at least one ether group.

In one embodiment, when the styryl ether is a compound containing one substituted styryl group and at least one ether group, the substituent is benzene, biphenyl, naphthalene, anthracene, phenanthrene, fluorene, carbazole, benzofuran or benzothiophene.

In one embodiment, the styryl group in the styryl ether is a distyryl group

In one embodiment, a monostyrylamine is a compound containing one non-substituted or substituted styryl group and at least one amino group.

In one embodiment, when the monostyrylamine is a compound containing one substituted styryl group and at least one amino group, the substituent is benzene, biphenyl, naphthalene, anthracene, phenanthrene, fluorene, carbazole, benzofuran or benzothiophene.

In one embodiment, the amino group in the monostyrylamine is an aromatic amino group.

In one embodiment, the styryl group in the monostyrylamine is a distyryl group.

In one embodiment, a distyrylamine is a compound containing two non-substituted or substituted styryl groups and at least one amino group.

In one embodiment, when the distyrylamine is a compound containing two substituted styryl groups and at least one amino group, the substituent is benzene, biphenyl, naphthalene, anthracene, phenanthrene, fluorene, carbazole, benzofuran or benzothiophene.

In one embodiment, the amino group in the distyrylamine is an aromatic amino group.

In one embodiment, the styryl group in the distyrylamine is a distyryl group.

In one embodiment, a tristyrylamine is a compound containing three non-substituted or substituted styryl groups and at least one amino group.

In one embodiment, when the tristyrylamine is a compound containing three substituted styryl groups and at least one amino group, the substituent is benzene, biphenyl, naphthalene, anthracene, phenanthrene, fluorene, carbazole, benzofuran or benzothiophene.

In one embodiment, the amino group in the tristyrylamine is an aromatic amino group.

In one embodiment, the styryl group in the tristyrylamine is a distyryl group.

In one embodiment, a tetrastyrylamine is a compound containing one non-substituted or substituted styryl group and at least one amino group.

In one embodiment, when the tetrastyrylamine is a compound containing one substituted styryl group and at least one amino group, the substituent is benzene, biphenyl, naphthalene, anthracene, phenanthrene, fluorene, carbazole, benzofuran or benzothiophene.

In one embodiment, the amino group in the tetrastyrylamine is an aromatic amino group.

In one embodiment, the styryl group in the tetrastyrylamine is a distyryl group.

In one embodiment, polystyrylamine and aryl amines disclosed in WO 2006/000388, WO 2006/058737, WO 2006/000389, WO 2007/065549, WO 2007/115610, U.S. Pat. No. 7,250,532B2, DE 102005058557A1, CN 1583691A, JP 08053397A, U.S. Pat. No. 6,251,531B1, US 2006/210830A, EP 1957606A1 and US 2008/0113101A1 can be used as organic functional materials of the present embodiment.

In one embodiment, the singlet emitter is 9,10-di-naphthylanthracene, naphthalene, tetraphenyl, oxyanthene, phenanthrene, 2,5,8,11-tetra-t-butylperylene, indenopyrene, 4,4'-bis(9-ethyl-3-carbazovinylene)-1,1'-biphenyl), periflanthene, decacyclene, coronene, fluorene, spirobifluorene, aryl pyren (e.g., the aryl pyren as disclosed in US20060222886), arylenevinylene (e.g., the arylenevinylenes disclosed in U.S. Pat. Nos. 5,121,029, 5,130,603), tetraphenylcyclopentadiene, rubrene, coumarine, rhodamine, quinacridone, 4 (dicyanoethylene)-6-(4-p-dimethylaminostyryl-2-methyl)-4H-pyrane, thiapyran, bis(azinyl)imine-boron compounds (e.g., the bis(azinyl)imine-boron compounds disclosed in US 2007/0092753 A1), bis(azinyl)methene compounds, carbostyryl compounds, oxazone, benzoxazole, benzothiazole, benzimidazole, and diketopyrrolopyrrole In one embodiment, the singlet light-emitting materials disclosed in US 20070252517 A1, U.S. Pat. Nos. 4,769,292, 6,020,078, US 2007/0252517A1 and US 2007/0252517A1 can be used as organic functional materials of the present embodiment.

In one embodiment, the singlet emitter has a structural formula as:

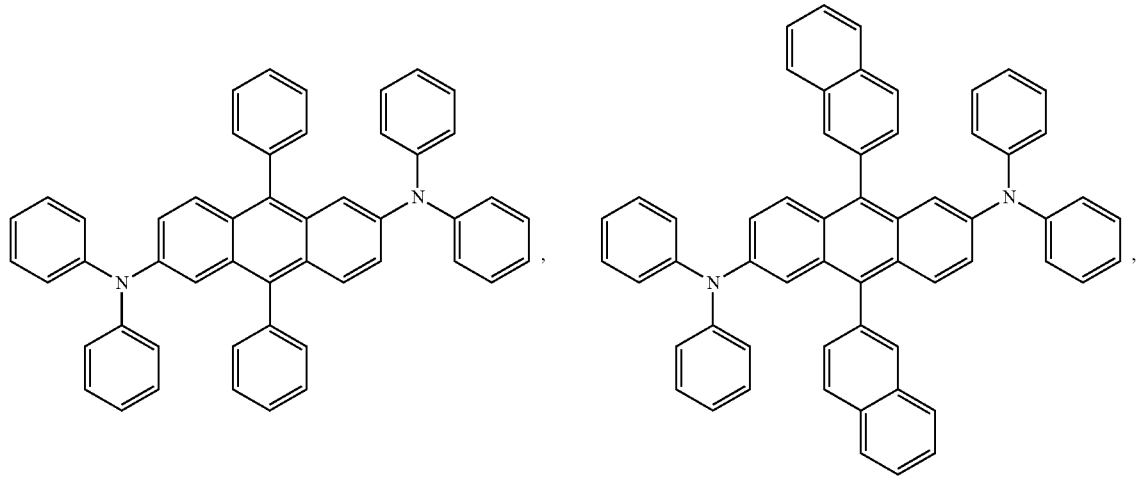

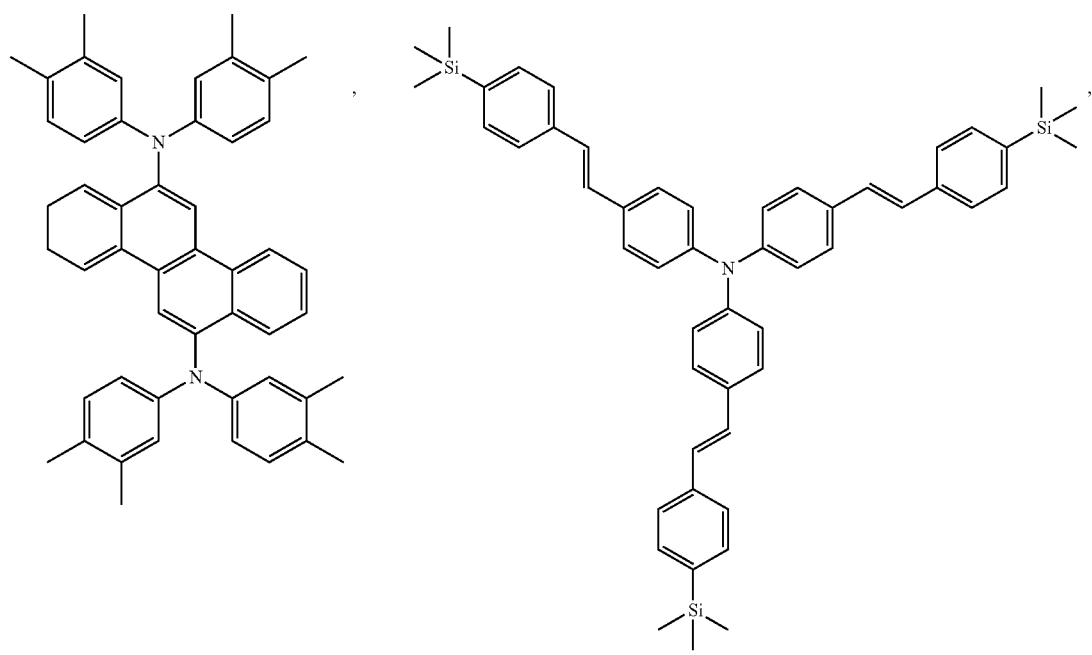

-continued
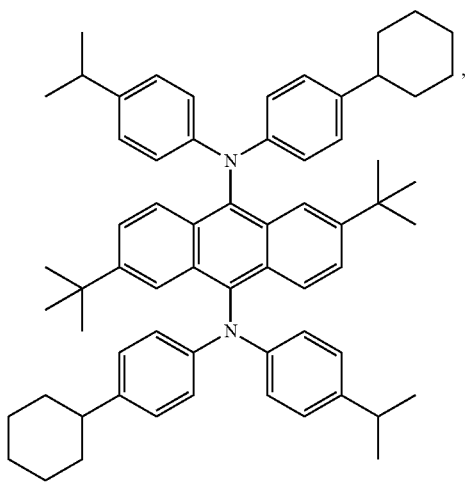
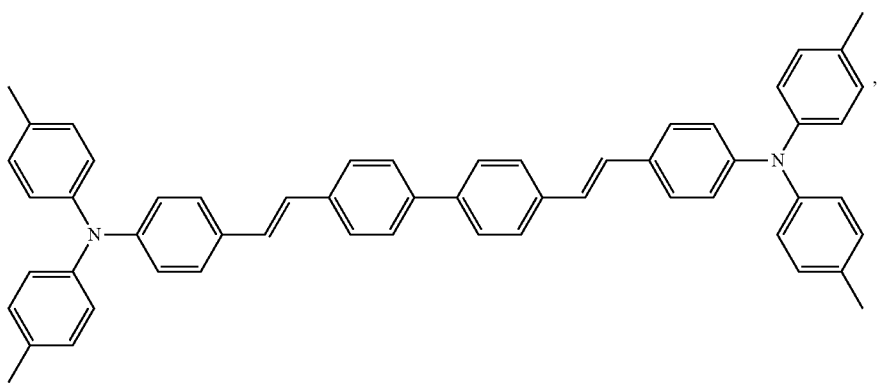
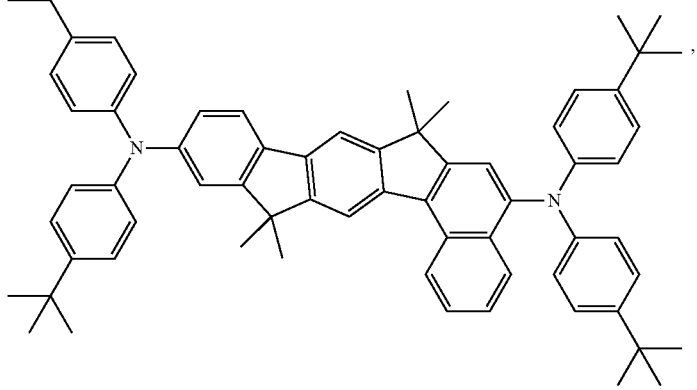
or
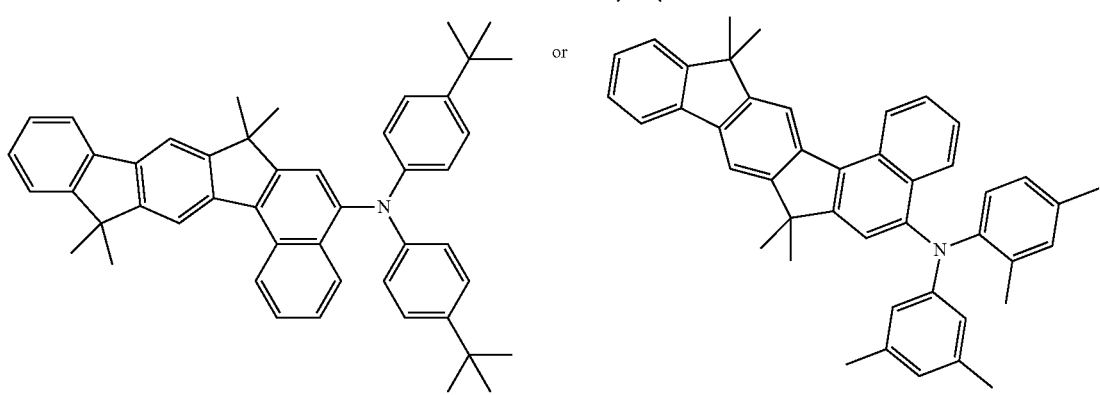

Thermally-activated delayed fluorescent materials are the third generation of organic light-emitting materials, having a small ΔEst, and triplet excitons can be converted to singlet excitons by anti-intersystem crossing. The TADF material has a good stability and the internal quantum efficiency of the device can reach 100%. However, traditional organic fluorescent materials can only emit light using 25% singlet excitonic luminescence formed by electrical excitation, and the devices have relatively low internal quantum efficiency (up to 25%). The phosphorescent material enhances the intersystem crossing due to the strong spin-orbit coupling of the heavy atom center, and the singlet exciton and the triplet exciton formed by the electric excitation can be effectively utilized for luminescence, so that the internal quantum efficiency of the device can reach 100%, however, the phosphorescent materials are expensive, the material stability is poor, and the device efficiency roll-off is a serious problem, which limit its application in OLED.

In one embodiment, the TADF material has a ΔEst less than 0.3 eV.

In one embodiment, the TADF material has a ΔEst less than 0.2 eV.

In one embodiment, the TADF material has a ΔEst less than 0.1 eV.

In one embodiment, the TADF material has a ΔEst less than 0.05 eV.

In one embodiment, the TADF material has a fluorescence quantum efficiency of 30% to 90%.

In one embodiment, the TADF materials disclosed in CN 103483332A, TW 201309696A, TW 201309778A, TW 201343874A, TW 201350558A, US 20120217869A1, WO 2013133359A1, WO 2013154064A1, Adachi, et. al. Adv. Mater., 21, 2009, 4802, Adachi, et. al. Appl. Phys. Lett., 98, 2011, 083302, Adachi, et. al. Appl. Phys. Lett., 101, 2012, 093306, Adachi, et. al. Chem. Commun., 48, 2012, 11392, Adachi, et. al. Nature Photonics, 6, 2012, 253, Adachi, et. al. Nature, 492, 2012, 234, Adachi, et. al. J. Am. Chem. Soc, 134, 2012, 14706, Adachi, et. al. Angew. Chem. Int. Ed, 51, 2012, 11311, Adachi, et. al. Chem. Commun., 48, 2012, 9580, Adachi, et. al. Chem. Commun., 48, 2013, 10385, Adachi, et. al. Adv. Mater., 25, 2013, 3319, Adachi, et. al. Adv. Mater., 25, 2013, 3707, Adachi, et. al. Chem. Mater., 25, 2013, 3038, Adachi, et. al. Chem. Mater., 25, 2013, 3766, Adachi, et. al. J. Mater. Chem. C., 1, 2013, 4599, Adachi, et. al. J. Phys. Chem. A., 117, 2013, 5607 can be used as organic functional materials in the present embodiment.

In one embodiment, the TADF material has a structural formula as:

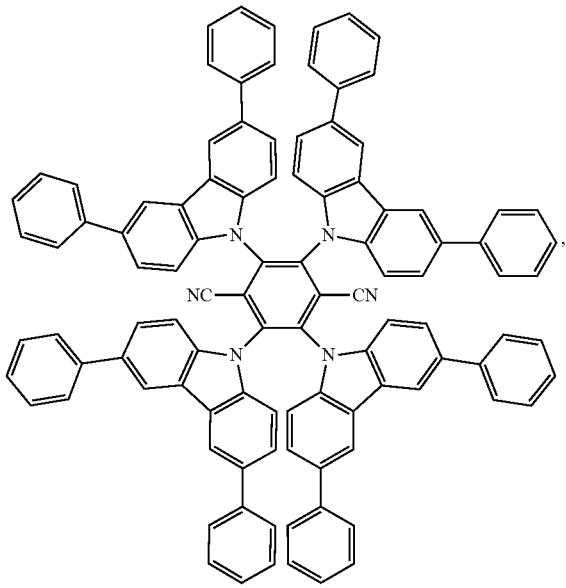

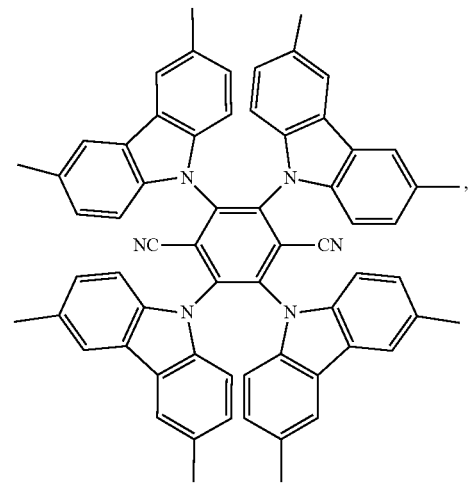

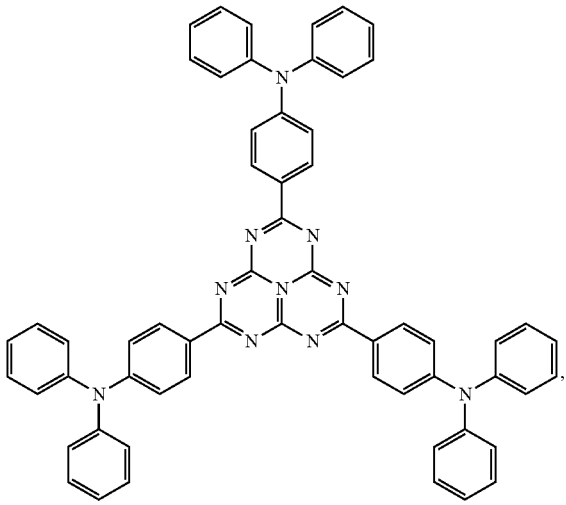

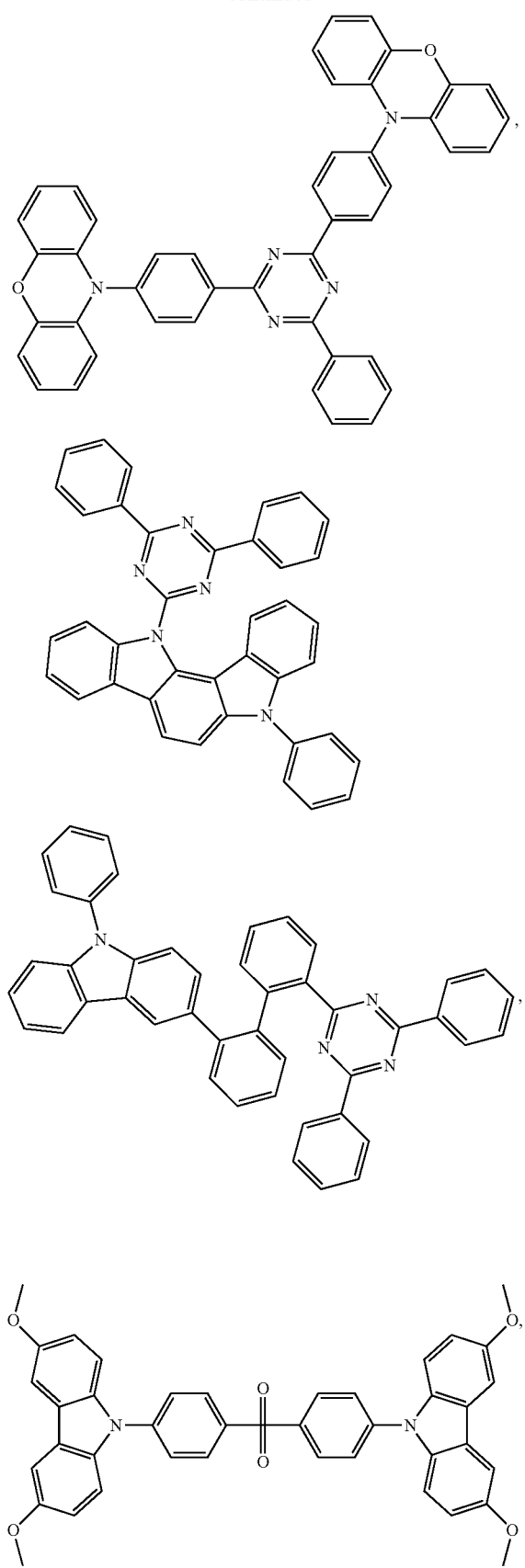
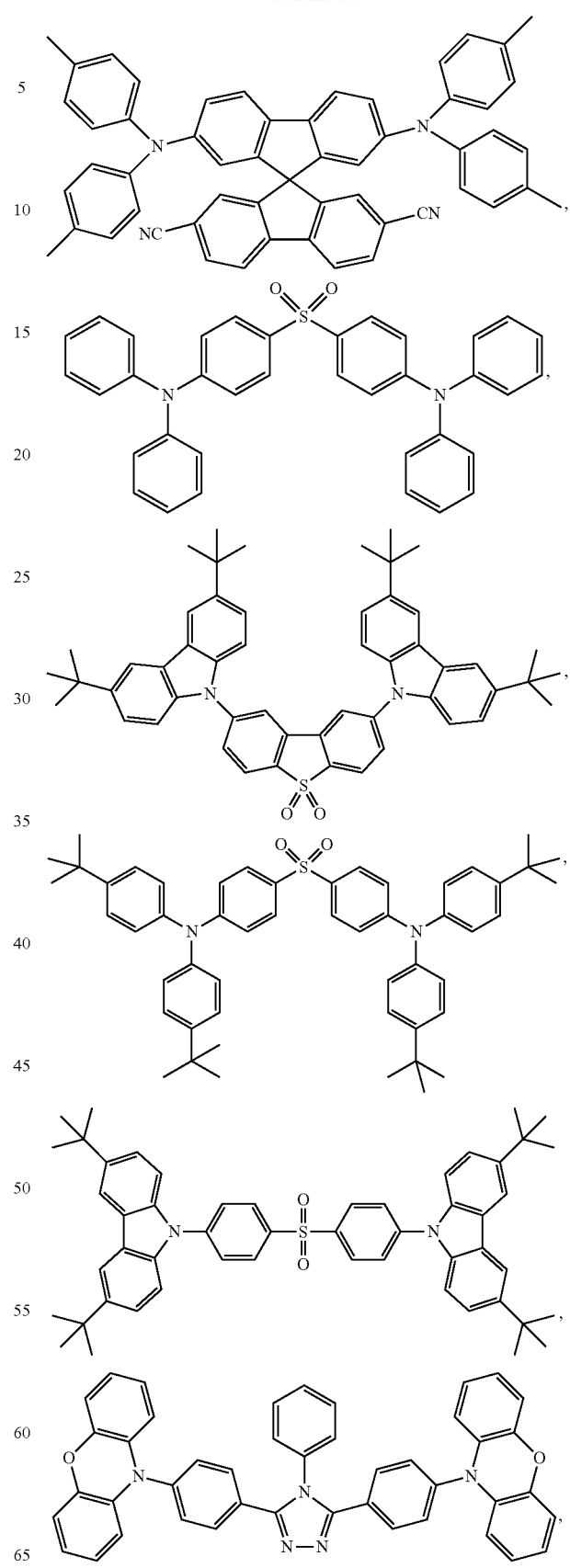

83
-continued
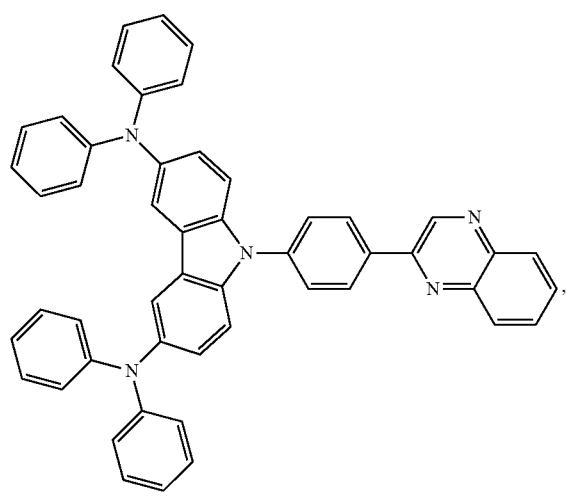
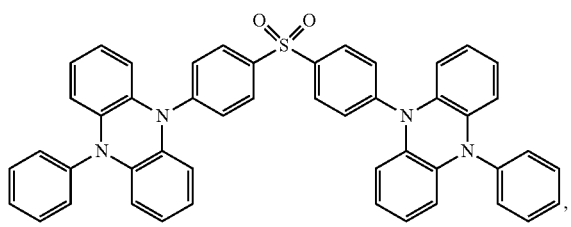
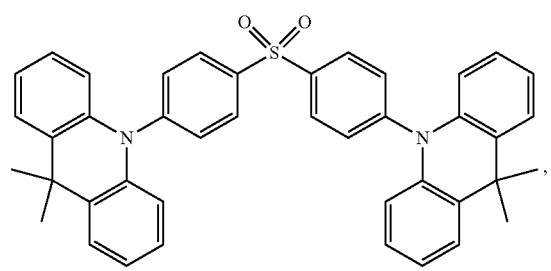
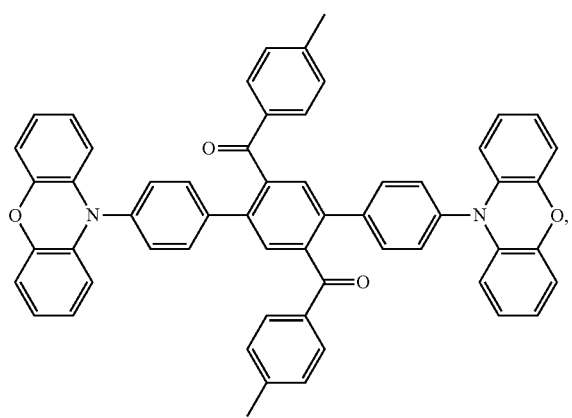
84
-continued
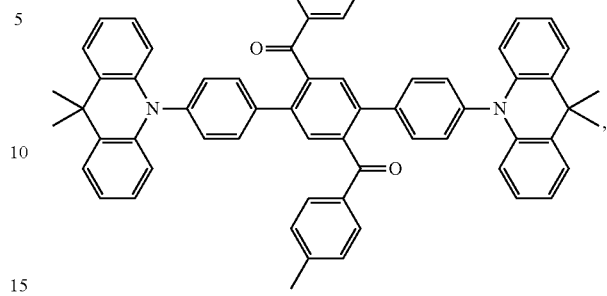
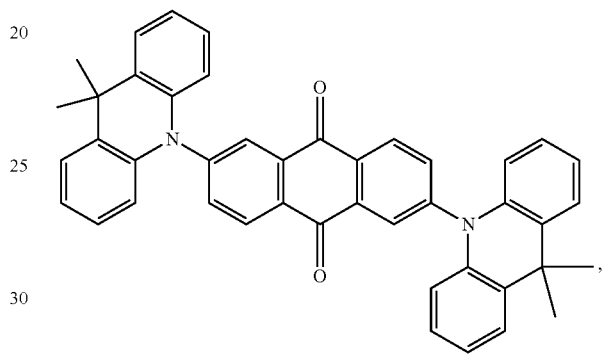
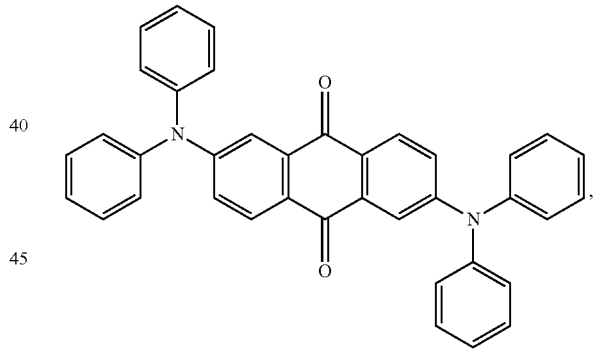
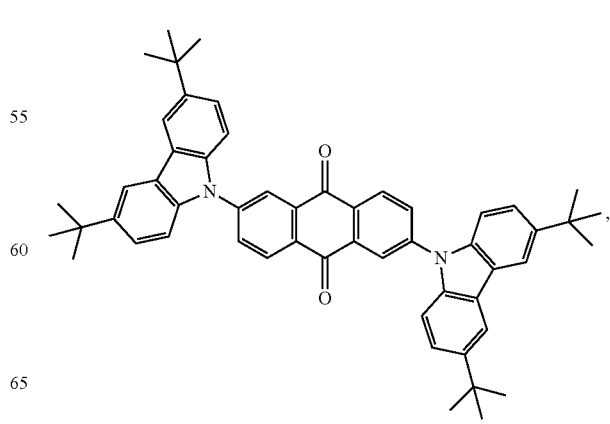

85
-continued
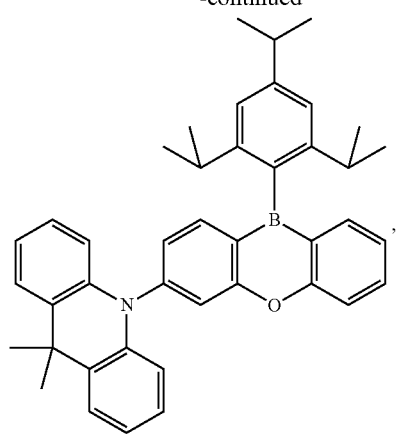
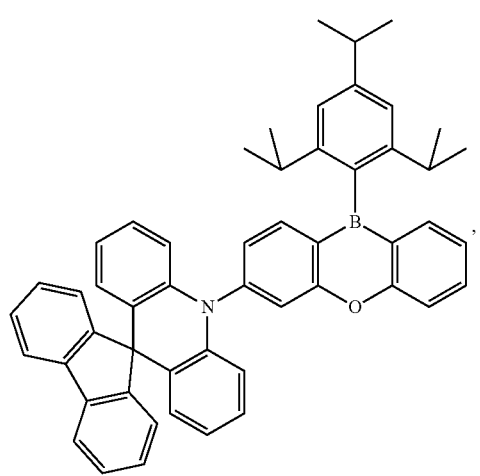
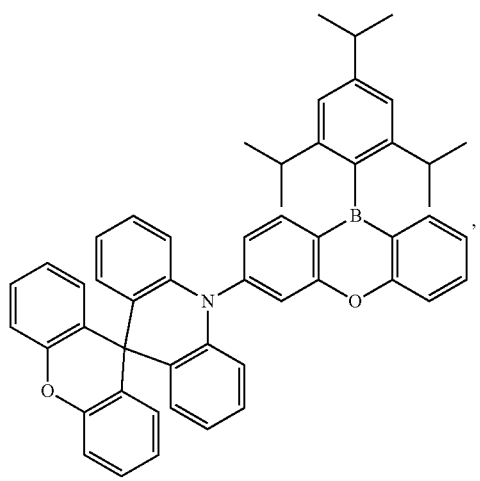
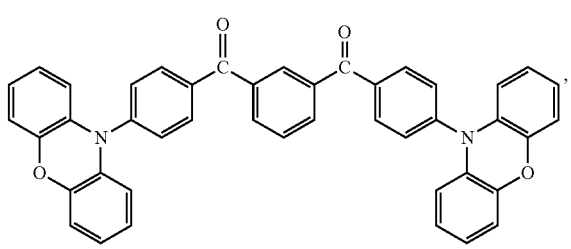
86
-continued
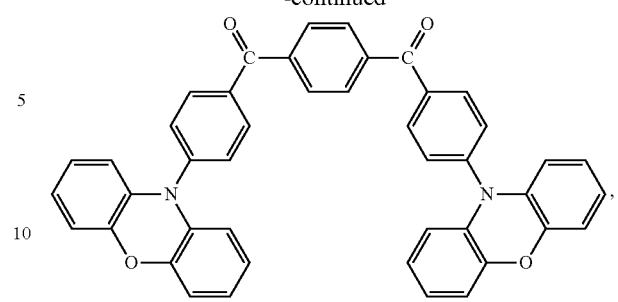
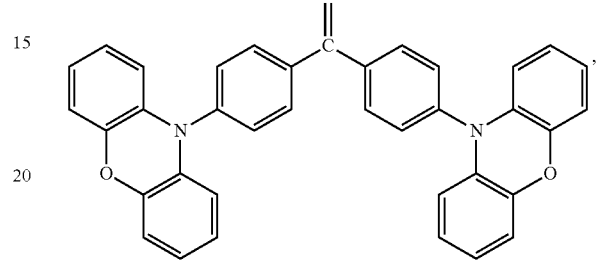
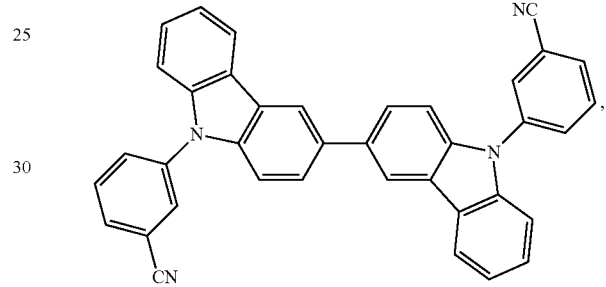
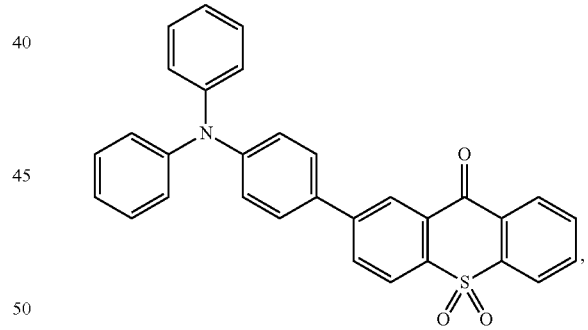
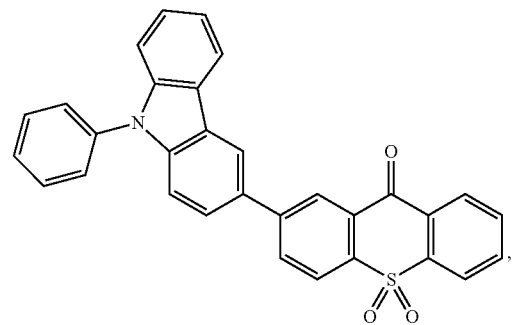

A triplet emitter is also called a phosphorescent emitter.

In one embodiment, the triplet emitter is a metal complex.

In one embodiment, the triplet emitter has a structural formula as G(L)t$_1$, wherein G is a metal atom, L is an organic ligand, and L is chemically or coordinately bonded to G through one or more positions; t$_1$ is an integer greater than 1.

It should be noted that a compound is obtained by linking a metal complex to a polymer through one or more positions may also used as a triplet emitter.

In one embodiment, the metal complex is linked to a polymer through one or more locations of L.

In one embodiment, G is a transition metal element, a lanthanide element or an actinide element.

In one embodiment, G is Ir, Pt, Pd, Au, Rh, Ru, Os, Sm, Eu, Gd, Tb, Dy, Re, Cu or Ag.

In one embodiment, G is Os, Ir, Ru, Rh, Re, Pd or Pt.

In one embodiment, t$_1$ of Ls in one structural formula of the triplet emitter may be the same ligand or different ligands.

In one embodiment, the organic ligand is a chelating ligand, i.e., the organic ligand is linked to the metal by at least two bonding sites to form a coordinate bond. Chelating ligands help to improve stability of metal complexes.

In one embodiment, the organic ligand is a bidentate ligand or a multidentate ligand.

In one embodiment, the triplet emitter includes 2 to 3 identical or different bidentate ligands or multidentate ligands.

In one embodiment, the organic ligand is a phenylpyridine derivative, a 7,8-benzoquinoline derivative, a 2-(2-thienyl)-pyridine derivative, a 2-(1-naphthyl)-pyridine derivative, or a 2 phenylquinoline derivative. And, it should be noted that all the organic ligand may be substituted, for example, with fluoromethyl or trifluoromethyl.

In one embodiment, t$_1$ is selected from 1, 2, 3, 4, 5 or 6.

In one embodiment, when the triplet emitter is a metal complex, an auxiliary ligand is further included, and the auxiliary ligand is acetylacetonate or picric acid.

In one embodiment, when the triplet emitter is a metal complex, the triplet emitter has a formula as follow:

$$[L\!-\!\!\!\!\!_{t_1}\!\!G\!\!<\!\!\begin{array}{c}f_1\\|\\f_2\end{array}]_{t_2},$$

wherein G is a transition metal element, a lanthanide element or an actinide element.

L is an organic ligand;

f$_1$ is a cyclic group containing at least one donor atom (i.e., an atom having a lone pair of electrons), and f$_1$ is bonded to G through a donor atom;

f$_2$ is a cyclic group containing at least one C atom, and f$_2$ is bonded to G through a C atom;

f$_1$ and f$_2$ are connected by a covalent bond;

t$_1$ is 0, 1 or 2.

t$_2$ is 1, 2 or 3.

In one embodiment, t$_1$ of Ls in one structural formula of the triplet emitter may be the same ligand or different ligands.

In one embodiment, L is a bidentate chelating ligand.

In one embodiment, L is a monoanionic bidentate chelating ligand.

In one embodiment, in one structural formula of the triplet emitter, t$_2$ of f$_1$s may be the same group or different groups.

In one embodiment, the donor atom is nitrogen or phosphorus.

In one embodiment, f$_1$ is a cyclic group having one or more substituent groups.

In one embodiment, the substituent group of f$_1$ is oxygen, pyridyl, diazole or triazole.

In one embodiment, in one structural formula of the triplet emitter, t$_2$ of f$_2$s may be the same group or different groups.

In one embodiment, f$_2$ is a cyclic group having one or more substituent groups.

In one embodiment, the substituent group of f$_2$ is oxygen, phenyl or dibenzofuran.

In one embodiment, when both f$_1$ and f$_2$ are cyclic groups having substituents, f$_1$ and f$_2$ may be bonded by forming a covalent bond between the substituents of them.

In one embodiment, t$_1$ is 1 or 2.

In one embodiment, t$_1$ is 0.

In one embodiment, t$_2$ is 2 or 3.

In one embodiment, t$_2$ is 3.

In one embodiment, the triplet emitters disclosed in WO 200070655, WO 200141512, WO 200202714, WO 200215645, EP 1191613, EP 1191612, EP 1191614, WO 2005033244, WO 2005019373, US 2005/0258742, WO 2009146770, WO 2010015307, WO 2010031485, WO 2010054731, WO 2010054728, WO 2010086089, WO 2010099852, WO 2010102709, US 20070087219A1, US 20090061681A1, US 20010053462A1, US 20090061681A1, US 20090061681A1, US 2007/0252517A1, U.S. Pat. Nos. 6,824,895, 7,029,766, 6,835, 469, 6,830,828, US 20010053462A1, WO 2007095118A1, US 2012004407A1, WO 2012007088A1, WO2012007087A1, WO 2012007086A1, US 2008027220A1, WO 2011157339A1, CN 102282150A, WO 2009118087A1, Baldo, Thompson et al. Nature 403, (2000), 750-753, Adachi et al. Appl. Phys. Lett. 78 (2001), 1622-1624, J. Kido et al. Appl. Phys. Lett. 65 (1994), 2124, Kido et al. Chem. Lett. 657, 1990, Johnson et al., JACS 105, 1983, 1795, Wrighton, JACS 96, 1974, 998, Ma et al., Synth. Metals 94, 1998, 245 can be used as organic functional materials in the present embodiment.

In one embodiment, the triplet emitter has a structural formula selected from the following structural formulas:

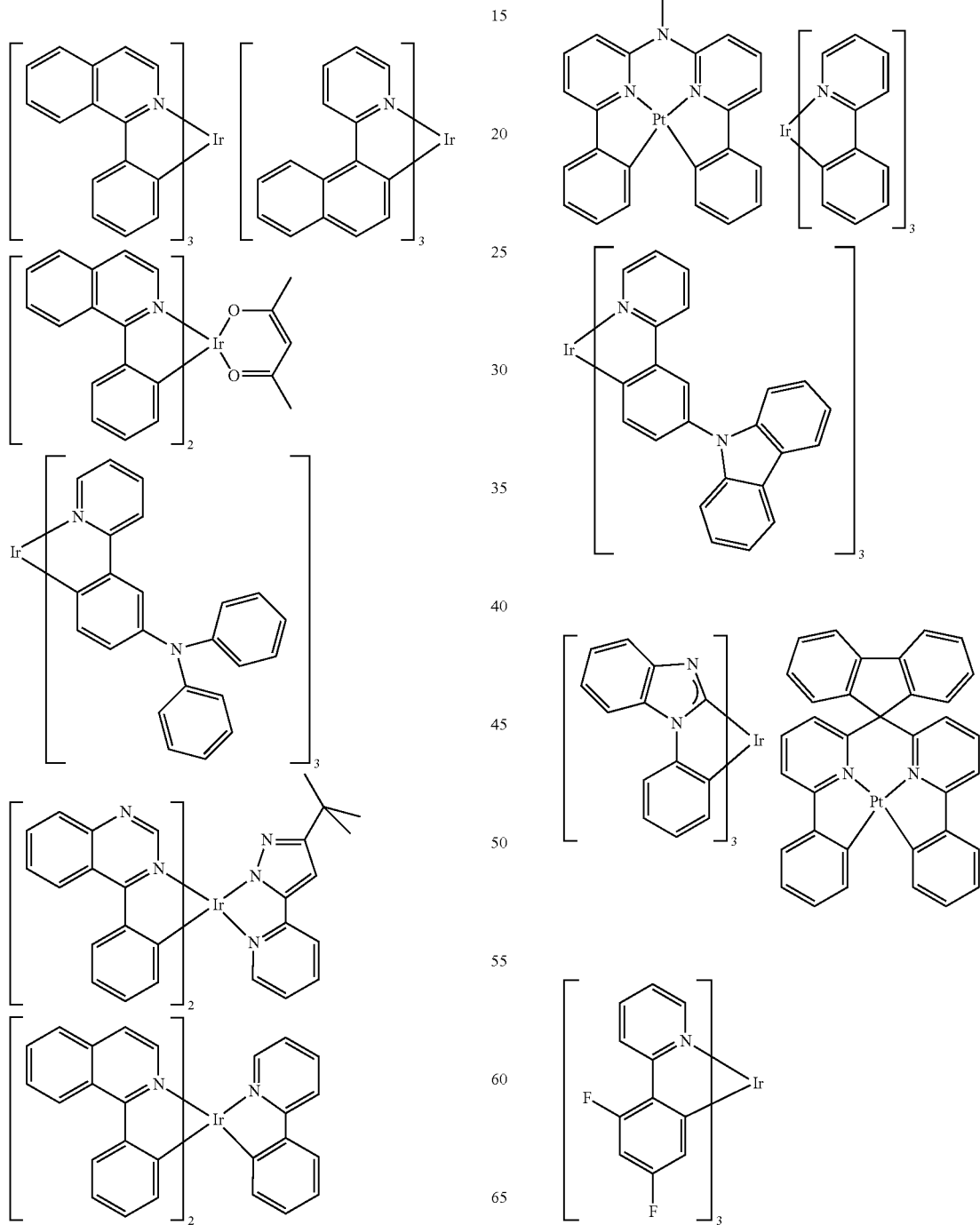

-continued
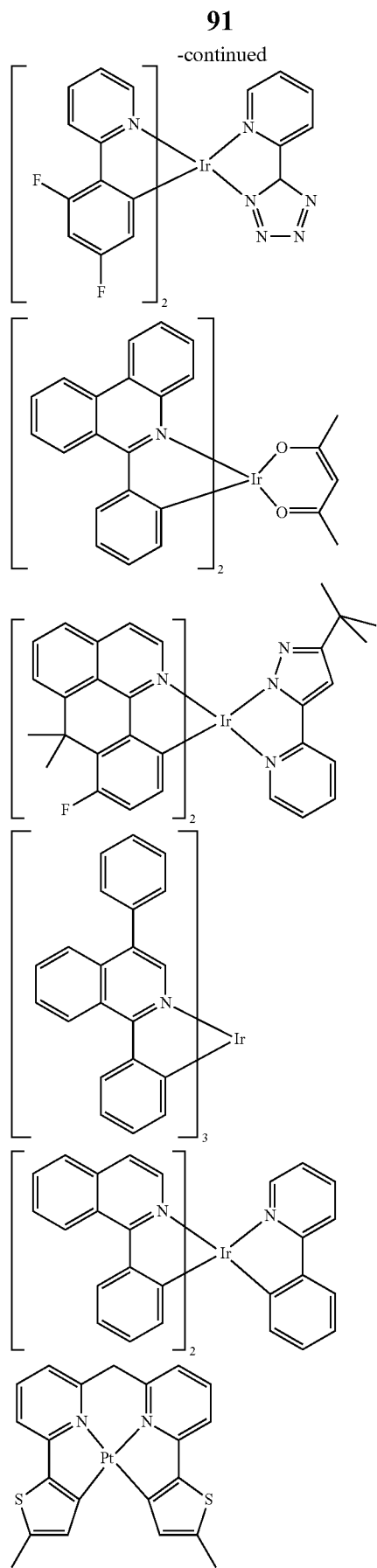
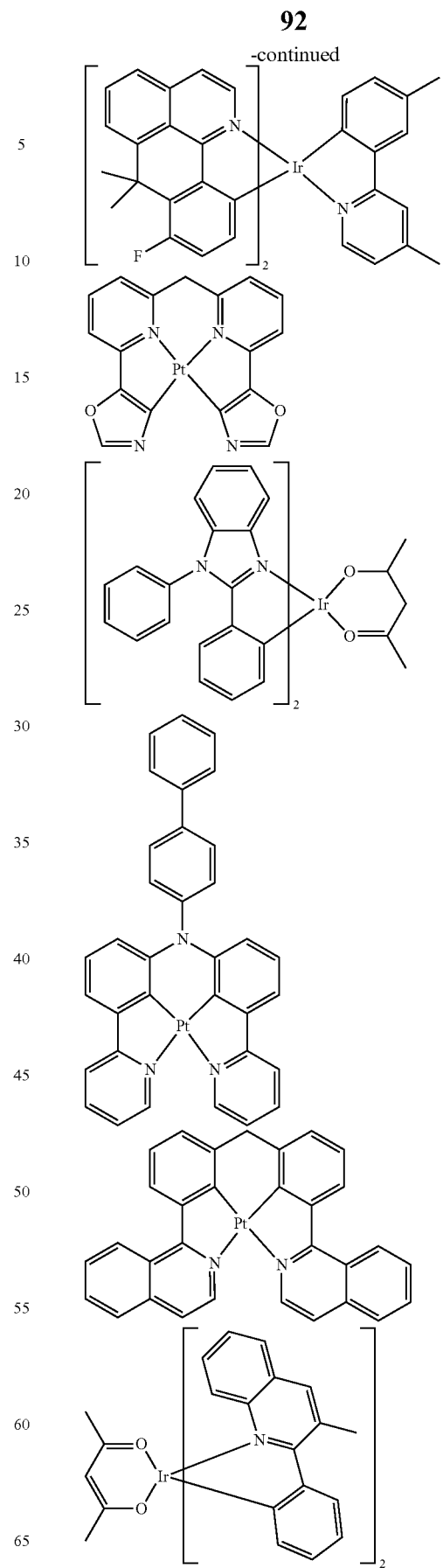

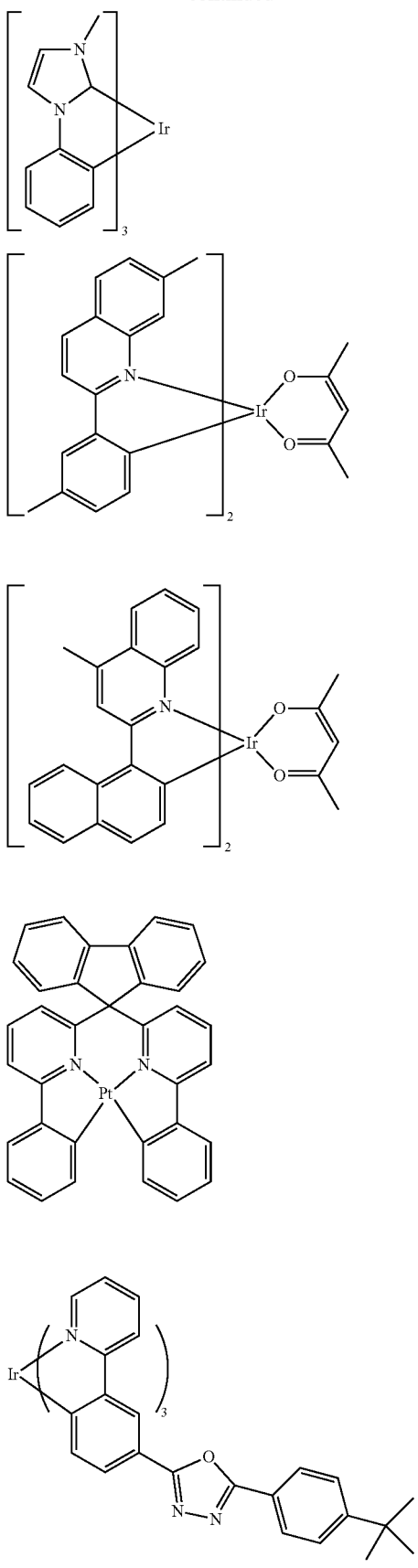
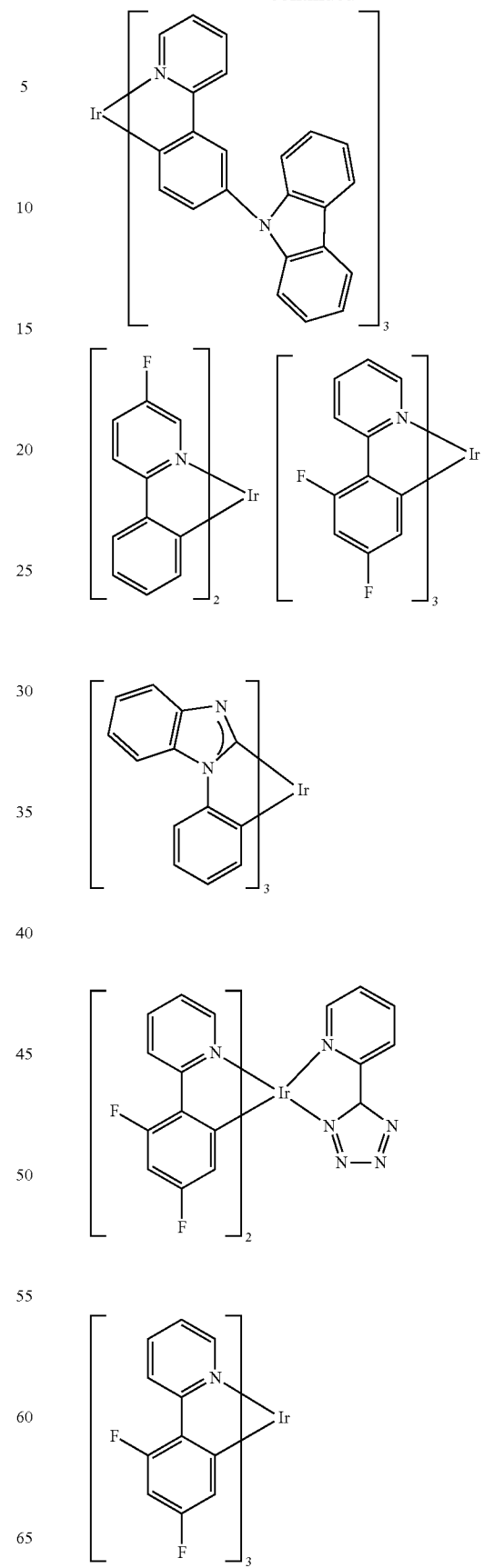

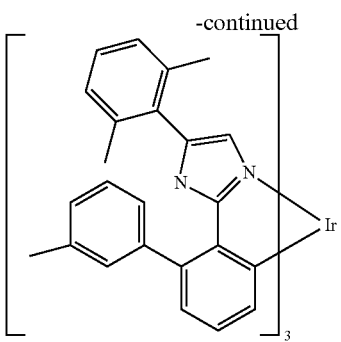

In one embodiment, the organic functional material is a light-emitting metal organic complex.

In one embodiment, the nitrogen-containing fused heterocyclic compound or the nitrogen-containing fused heterocyclic polymer in the organic electroluminescent material has a mass percentage of 50 wt % to 99.9 wt %.

In one embodiment, the nitrogen-containing fused heterocyclic compound or the nitrogen-containing fused heterocyclic polymer in the organic electroluminescent material has a mass percentage of 60 wt % to 97 wt %.

In one embodiment, the nitrogen-containing fused heterocyclic compound or the nitrogen-containing fused heterocyclic polymer in the organic electroluminescent material has a mass percentage of 70 wt % to 95 wt %.

In one embodiment, the nitrogen-containing fused heterocyclic compound or the nitrogen-containing fused heterocyclic polymer in the organic electroluminescent material has a mass percentage of 70 wt % to 90 wt %.

In one embodiment, the organic electroluminescent material comprises the nitrogen-containing fused heterocyclic compound or the nitrogen-containing fused heterocyclic polymer and a triplet emitter, wherein the nitrogen-containing fused heterocyclic compound or the nitrogen-containing fused heterocyclic polymer is used as a host material.

In one embodiment, the organic electroluminescent material includes 70% to 99% by mass of the nitrogen-containing fused heterocyclic compound or the nitrogen-containing fused heterocyclic polymer, and 1% to 30% by mass of a triplet emitter.

In one embodiment, the organic electroluminescent material includes 75% to 99% by mass of the nitrogen-containing fused heterocyclic compound or the nitrogen-containing fused heterocyclic polymer, and 1% to 25% by mass of a triplet emitter.

In one embodiment, the organic electroluminescent material includes 80% to 99% by mass of the nitrogen-containing fused heterocyclic compound or the nitrogen-containing fused heterocyclic polymer, and 1% to 20% by mass of a triplet emitter.

In one embodiment, the organic electroluminescent material includes the nitrogen-containing fused heterocyclic compound or the nitrogen-containing fused heterocyclic polymer, a host material, and a triplet emitter.

In one embodiment, the organic electroluminescent material includes 10% to 89% by mass of the nitrogen-containing fused heterocyclic compound or the nitrogen-containing fused heterocyclic polymer, 1% to 20% by mass of a host material, and 10% to 70% by mass of a triplet emitter; wherein the nitrogen-containing fused heterocyclic compound or the nitrogen-containing fused heterocyclic polymer is used together with the host material as the main light-emitting layer material.

In one embodiment, the organic electroluminescent material includes 10% to 79% by mass of the nitrogen-containing fused heterocyclic compound or the nitrogen-containing fused heterocyclic polymer, 1% to 20% by mass of a host material, and 20% to 70% by mass of a triplet emitter.

In a further embodiment, the organic electroluminescent material includes 10% to 69% by mass of the nitrogen-containing fused heterocyclic compound or the nitrogen-containing fused heterocyclic polymer, 1% to 20% by mass of a host material, and 30% to 70% by mass of a triplet emitter.

In one embodiment, the organic electroluminescent material includes 10% to 59% by mass of the nitrogen-containing fused heterocyclic compound or the nitrogen-containing fused heterocyclic polymer, 1% to 20% by mass of a host material, and 40% to 70% by mass of a triplet emitter.

In one embodiment, the organic electroluminescent material includes the nitrogen-containing fused heterocyclic compound or the nitrogen-containing fused heterocyclic polymer, a host material, and a triplet emitter; wherein the nitrogen-containing fused heterocyclic compound or the nitrogen-containing fused heterocyclic polymer and the host material are auxiliary light-emitting material.

In one embodiment, the mass ratio of the nitrogen-containing fused heterocyclic compound or the nitrogen-containing fused heterocyclic polymer to the triplet emitter is 1:2 to 2:1.

In one embodiment, the T1 of the nitrogen-containing fused heterocyclic compound or the nitrogen-containing fused heterocyclic polymer is higher than that of the triplet emitter.

In one embodiment, the organic electroluminescent material includes the nitrogen-containing fused heterocyclic compound or the nitrogen-containing fused heterocyclic polymer, and a TADF material.

In one embodiment, the organic electroluminescent material includes 50% to 99% by mass of the nitrogen-containing fused heterocyclic compound or the nitrogen-containing fused heterocyclic polymer, and 1% to 50% by mass of a TADF material.

In one embodiment, the organic electroluminescent material includes the nitrogen-containing fused heterocyclic compound or the nitrogen-containing fused heterocyclic polymer, and an ETM material.

In one embodiment, the organic electroluminescent material includes 10% to 99% by mass of the nitrogen-containing fused heterocyclic compound or the nitrogen-containing fused heterocyclic polymer, and 1% to 90% by mass of an ETM material.

The foregoing organic electroluminescent material has at least the following advantages:

The foregoing organic electroluminescent material including the foregoing nitrogen-containing fused heterocyclic compound or the foregoing nitrogen-containing fused heterocyclic polymer has a good solubility, stability and optoelectronic property, and can be used as a hole injection material, a hole transporting material, an electron transporting material, and an electron injection material, an electron blocking material, a hole blocking material, an emitter and a host material, and has a wide range of applications, and the materials and the devices including the nitrogen-containing fused heterocyclic polymer have a good stability and a long lifetime.

An organic electroluminescent material of another embodiment includes the foregoing nitrogen-containing fused heterocyclic compound or the foregoing nitrogen-containing fused heterocyclic polymer, and an organic solvent.

In one embodiment, the organic solvent is at least one selected from the group consisting of an aromatic solvent, a heteroaromatic solvent, an aromatic ketone solvent, an aromatic ether solvent, an ester solvent, an aliphatic ketone solvent, and an aliphatic ether solvent.

In one embodiment, the organic solvent is at least one selected from an aliphatic chain-substituted aromatic solvent and an aliphatic ring-substituted aromatic solvent.

In one embodiment, the aromatic solvent or the heteroaromatic solvent is p-diisopropylbenzene, pentylbenzene, tetrahydronaphthalene, cyclohexyl benzene, chloronaphthalene, 1,4-dimethylnaphthalene, 3-isopropylbiphenyl, p-cymene, dipentylbenzene, tripentylbenzene, pentyltoluene, o-xylene, m-xylene, p-xylene, o-diethylbenzene, m-diethylbenzene, p-diethylbenzene, 1,2,3,4-tetramethylbenzene, 1,2,3,5-tetramethylbenzene, 1,2,4,5-tetramethylbenzene, butylbenzene, dodecylbenzene, dihexylbenzene, dibutylbenzene, p-diisopropylbenzene, 1-methoxynaphthalene, cyclohexylbenzene, dimethylnaphthalene, 3-isopropylbiphenyl, p-cymene, 1-methylnaphthalene, 1,2,4-trichlorobenzene, 1,3-dipropoxybenzene, 4,4-difluorodiphenylmethane, 1,2-dimethoxy-4-(1-propenyl)benzene, diphenylmethane, 2-phenylpyridine, 3-phenylpyridine, N-methyldiphenylamine 4-isopropylbiphenyl, α,α-dichlorodiphenylmethane, 4-(3-phenylpropyl)pyridine, benzylbenzoate, 1,1-di(3,4-dimethylphenyl)ethane, 2-isopropylnaphthalene or dibenzylether.

In one embodiment, the aromatic ketone solvent is 1-tetralone, 2-tetralone, 2-(phenylepoxy)tetralone, 6-(methoxyl)tetralone, acetophenone, phenylacetone, benzophenone, and derivatives thereof.

In one embodiment, derivatives of the aromatic ketone solvent is 4-methylacetophenone, 3-methylacetophenone, 2-methylacetophenone, 4-methylphenylacetone, 3-methylphenylacetone, 2-methylphenylacetone, isophorone, 2,6,8-trimethy-1-4-nonanone, fenchone, 2-nonanone, 3-nonanone, 5-nonanone, 2-decanone, 2,5-hexanedione, phorone or di-n-amyl ketone.

In one embodiment, the aromatic ether solvent is 3-phenoxytoluene, butoxybenzene, benzylbutylbenzene, p-anisaldehyde dimethyl acetal, tetrahydro-2-phenoxy-2H-pyran, 1,2-dimethoxy-4-(1-propenyl)benzene, 1,4-benzodioxane, 1,3-dipropylbenzene, 2,5-dimethoxytoluene, 4-ethylphenetole, 1,2,4-trimethoxybenzene, 4-(1-propenyl)-1,2-dimethoxybenzene, 1,3-dimethoxybenzene, glycidyl phenyl ether, dibenzyl ether, 4-tert-butylanisole, trans-p-propenylanisole, 1,2-dimethoxybenzene, 1-methoxynaphthalene, diphenyl ether, 2-phenoxymethyl ether, 2-phenoxytetrahydrofuran, ethyl-2-naphthyl ether, pentyl ether, hexyl ether, dioctyl ether, ethylene glycol dibutyl ether, diethylene glycol diethyl ether, diethylene glycol butyl methyl ether, diethylene glycol dibutyl ether, triethylene glycol dimethyl ether, triethylene glycol ethyl methyl ether, triethylene glycol butyl methyl ether, tripropylene glycol dimethyl ether or tetraethylene glycol dimethyl ether.

In one embodiment, the ether solvent is alkyl octoate, alkyl sebacate, alkyl stearate, alkyl benzoate, alkyl phenylacetate, alkyl cinnamate, alkyl oxalate, alkyl maleate, alkyl lactone, alkyl oleate.

In one embodiment, the aliphatic ketone solvents are 2-nonanone, 3-nonanone, 5-nonanone, 2-decanone, 2,5-hexanedione, 2,6,8-trimethyl-4-nonanone, phorone or di-n-pentyl ketone In one embodiment, the aliphatic ether is amyl ether, hexyl ether, dioctyl ether, ethylene glycol dibutyl ether, diethylene glycol diethyl ether, diethylene glycol butyl methyl ether, diethylene glycol dibutyl ether, triethylene glycol dimethyl ether, triethyl ether alcohol ethyl methyl ether, triethylene glycol butyl methyl ether, tripropylene glycol dimethyl ether or tetraethylene glycol dimethyl ether.

In one embodiment, the organic solvent has a mass percentage of 70% to 99.7% in the organic electroluminescent material, and the forgoing nitrogen-containing fused heterocyclic compound or the forgoing nitrogen-containing fused heterocyclic polymer has a mass percentage of 0.3 wt % to 30 wt %. And, it should be noted that the mass percentage of the organic solvent and the foregoing nitrogen-containing fused heterocyclic compound or the foregoing nitrogen-containing fused heterocyclic polymer in the organic electroluminescent material is not limited to the above-mentioned range, and may be adjusted as needed, e.g., the content of each component in the organic electroluminescent material can be adjusted according to the desired viscosity.

In one embodiment, the organic solvent has a mass percentage of 80% to 99.8% in the organic electroluminescent material, and the foregoing nitrogen-containing fused heterocyclic compound or the foregoing nitrogen-containing fused heterocyclic polymer has a mass percentage of 0.2% to 20% by mass.

In one embodiment, the organic solvent has a mass percentage of 85% to 99.5% in the organic electroluminescent material, and the foregoing nitrogen-containing fused heterocyclic compound or the foregoing nitrogen-containing fused heterocyclic polymer has a mass percentage of 0.5% to 15% by mass.

In one embodiment, the organic solvent has a mass percentage of 90% to 99.5% in the organic electroluminescent material, and the foregoing nitrogen-containing fused heterocyclic compound or the foregoing nitrogen-containing fused heterocyclic polymer has a mass percentage of 0.5% to 10% by mass.

In one embodiment, the organic solvent has a mass percentage of 95% to 99.0% in the organic electroluminescent material, and the foregoing nitrogen-containing fused heterocyclic compound or the foregoing nitrogen-containing fused heterocyclic polymer has a mass percentage of 1% to 5%.

In one embodiment, the organic electroluminescent material further includes an auxiliary solvent for adjusting aggregation during the film formation of the organic electroluminescent material and thin film surface morphology.

In one embodiment, the auxiliary solvent is at least one selected from methanol, ethanol, 2-methoxyethanol, dichloromethane, trichloromethane, chlorobenzene, o-dichlorobenzene, tetrahydrofuran, anisole, morpholine, toluene, o-xylene, m-xylene, p-xylene, 1,4-dioxane, acetone, methyl ethyl ketone, 1,2-dichloroethane, 3-phenoxy toluene, 1,1,1-trichloroethane, 1,1,2,2-tetrachloroethane, ethyl acetate, butyl acetate, dimethylformamide, dimethylacetamide, dimethyl sulfoxide, tetrahydronaphthalene, decalin and indene.

In one embodiment, the organic electroluminescent material includes 10% to 50% by mass of the foregoing nitrogen-containing fused heterocyclic compound or the foregoing nitrogen-containing fused heterocyclic polymer, 40% to 85% by mass of an organic solvent, and 5% to 50% by mass of an auxiliary solvent.

In one embodiment, the organic electroluminescent material further includes a modifier for adjusting the viscosity, film-forming property or adhesion of the organic electroluminescent material.

In one embodiment, the modifier is one selected from a surfactant, a lubricant, a wetting agent, a dispersing agent, a hydrophobic agent, and a binder.

In one embodiment, the organic electroluminescent material includes 10% to 50% by mass of the foregoing nitrogen-containing fused heterocyclic compound or the foregoing nitrogen-containing fused heterocyclic polymer, 40% to 85% by mass of an organic solvent, 5% to 40% by mass of an auxiliary solvent, and 5% to 30% of a modifier.

In one embodiment, the organic electroluminescent material is a solution.

In one embodiment, the organic electroluminescent material is a suspension.

The organic electroluminescent material of another embodiment has at least the following advantages:

The foregoing organic electroluminescent material including the foregoing nitrogen-containing fused heterocyclic polymer or the foregoing nitrogen-containing fused heterocyclic compound has a good solubility, stability and optoelectronic property, and has a wide range of applications, and materials and devices including the nitrogen-containing fused heterocyclic compound have a good stability and a long lifetime, and at the same time, the foregoing electroluminescent material further includes an organic solvent, an auxiliary solvent and a modifier, and properties, such as viscosity, film-forming property or adhesion, of the organic electroluminescent material can be adjusted by adjusting the ratio of each component, thereby making the properties of the organic electroluminescent material controllable.

An organic electroluminescent material of another embodiment can be used in ink preparation.

An ink of one embodiment includes the organic electroluminescent material of another embodiment. It should be noted that the foregoing organic electroluminescent material can be directly printed as an ink, or added to other acceptable auxiliary materials in printing industries such as an organic solvent to form an ink.

In one embodiment, the ink has a surface tension of 19 dyne/cm to 50 dyne/cm at 25° C. to 220° C.

In one embodiment, the ink has a surface tension of 22 dyne/cm to 35 dyne/cm at 25° C. to 220° C.

In one embodiment, the ink has a surface tension of 25 dyne/cm to 33 dyne/cm at 25° C. to 220° C.

In one embodiment, the ink has a viscosity of 1 cps to 100 cps at 25° C. to 220° C. The viscosity of 1 cps to 100 cps allows the ink to be used in inkjet printing. And, it should be noted that the viscosity of the ink is not limited to the above-mentioned range, and may be adjusted by different methods, such as selecting an organic solvent or an auxiliary solvent, the content of the nitrogen-containing fused heterocyclic compound or the nitrogen-containing fused heterocyclic polymer.

In one embodiment, the ink has a viscosity of 1 cps to 50 cps at 25° C. to 220° C.

In one embodiment, the ink has a viscosity of 1.5 cps to 20 cps at 25° C. to 220° C.

In one embodiment, the ink has a viscosity of 4.0 cps to 20 cps at 25° C. to 220° C.

An ink of one embodiment has at least the following advantages:

The foregoing ink at 25° C. to 220° C. has a surface tension of 19 dyne/cm to 50 dyne/cm and a viscosity of 1 cps to 100 cps, so that the ink can be applied to inkjet printing.

A thin film of one embodiment includes an organic electroluminescent material of another embodiment or an ink of one embodiment. The thin film can be applied to the preparation of electronic devices.

In one embodiment, the foregoing thin film is prepared by printing or coating.

In one embodiment, the foregoing thin film is prepared by inkjet printing, nozzle printing, typography, screen printing, dip coating, spin coating, blade coating, roller printing, twist roller printing, lithography, flexography, rotary printing, spray coating, brush coating or transfer printing or slot die coating.

In one embodiment, the thin film is prepared by inkjet printing, slot die coating, nozzle printing or gravure printing.

An electronic device of one embodiment includes the foregoing nitrogen-containing fused heterocyclic polymer or the foregoing nitrogen-containing fused heterocyclic compound.

In one embodiment, the electronic device is an organic light-emitting diode (OLED), an organic photovoltaic (OPT), an organic light emitting electrochemical cell (OLEEC), an organic field effect transistor (OFET), an organic light emitting field effect transistor, an organic laser, an organic spin electronic device, an organic sensor, or an organic plasmon emitting diode.

In one embodiment, the electronic device is an organic light-emitting diode (OLED).

In one embodiment, the organic electronic device includes a cathode, an anode, and a functional layer between the cathode and the anode, wherein the functional layer includes the foregoing nitrogen-containing fused heterocyclic polymer or the foregoing nitrogen-containing fused heterocyclic compound.

In one embodiment, the functional layer is a light-emitting layer, a hole injection layer (HIL), a hole transporting layer (HTL), an electron blocking layer (EBL), an electron injection layer (EIL), an electron transporting layer (ETL), or a hole blocking layer (HBL).

In one embodiment, the electronic device has an emission wavelength of 300 nm to 1000 nm.

In one embodiment, the electronic device has an emission wavelength of 350 nm to 900 nm.

In one embodiment, the electronic device has an emission wavelength of 400 nm to 800 nm.

An electronic device of one embodiment has at least the following advantages:

The foregoing electronic device including the foregoing nitrogen-containing fused heterocyclic polymer or the foregoing nitrogen-containing fused heterocyclic compound allows the foregoing electronic device to have a good stability and a longer lifetime.

An organic electroluminescent device of one embodiment includes a substrate, a light-emitting layer, another functional layer, an anode, and a cathode. The light-emitting layer includes the foregoing nitrogen-containing fused heterocyclic polymer or the foregoing nitrogen-containing fused heterocyclic compound. The other functional layer is a hole injection layer, a hole transporting layer, an electron blocking layer, an electron injection layer, an electron transporting layer or a hole blocking layer. And, it should be noted that the other functional layer may be omitted when the light-emitting layer can meet the needs.

The substrate is a transparent plate for preparing a transparent organic electroluminescent device. And, it should be noted that the substrate can be an opaque plate.

In one embodiment, the substrate may be plastic, metal, a semiconductor wafer, or glass.

In one embodiment, the substrate has a smooth surface.

In one embodiment, the substrate is rigid or elastic.

In one embodiment, the substrate is a polymer thin film or a plastic thin film.

In one embodiment, the substrate is polyethylene terephthalate (PET) or polyethylene 2,6-naphthalate (PEN).

In one embodiment, the substrate has a $T_g$ (glass transition temperature) greater than or equal to 150° C.

In one embodiment, the substrate has a $T_g$ greater than or equal to 200° C.

In one embodiment, the substrate has a $T_g$ greater than or equal to 250° C.

In one embodiment, the substrate has a $T_g$ greater than or equal to 300° C.

The anode is laminated on the substrate. The anode includes a conductive metal, a metallic oxide, or a conductive polymer, so that the anode can inject holes easily into the light-emitting layer or the other functional layer.

In one embodiment, the material of the anode is Al, Cu, Au, Ag, Mg, Fe, Co, Ni, Mn, Pd, Pt, ITO, or AZO (aluminum-doped zinc oxide). It should be understood that the material of the anode is not limited to the above-mentioned materials, and other materials acceptable in the field of electronic devices, such as nickel hydroxide, may be selected as needed.

In one embodiment, the anode is prepared by physical vapor deposition.

In one embodiment, the anode is prepared by a radio frequency magnetron sputtering, a vacuum thermal evaporation coating or an electron beam (e-beam) evaporation coating.

In one embodiment, the absolute value of the difference between the work function of the anode and the LUMO energy level or the valence band energy level of the light-emitting material in the light-emitting layer is smaller than 0.5 eV.

In one embodiment, the absolute value of the difference between the work function of the anode and the LUMO energy level or the valence band energy level of the light-emitting material in the light-emitting layer is smaller than 0.3 eV.

In one embodiment, the absolute value of the difference between the work function of the anode and the LUMO energy level or the valence band energy level of the light-emitting material in the light-emitting layer is smaller than 0.2 eV.

In one embodiment, when the other functional layer is a hole injection layer or a hole transporting layer, the absolute value of the difference between the work function of the anode and the LUMO energy level or the valence band energy level of the p-type semiconductor material in the other functional layer is smaller than 0.5 eV.

In one embodiment, when the other functional layer is a hole injection layer or a hole transporting layer, the absolute value of the difference between the work function of the anode and the LUMO energy level or the valence band energy level of the p-type semiconductor material in the other functional layer is smaller than 0.3 eV.

In one embodiment, when the other functional layer is a hole injection layer or a hole transporting layer, the absolute value of the difference between the work function of the anode and the LUMO energy level or the valence band energy level of the p-type semiconductor material in the other functional layer is smaller than 0.2 eV.

The light-emitting layer is laminated on the side of the anode away from the substrate. The light-emitting layer includes the foregoing nitrogen-containing fused heterocyclic polymer or the foregoing nitrogen-containing fused heterocyclic compound.

In one embodiment, the light-emitting layer includes the foregoing nitrogen-containing fused heterocyclic polymer or the foregoing nitrogen-containing fused heterocyclic compound, and an emitter.

In one embodiment, the emitter is one selected from a singlet emitter, a triplet emitter, and a thermally activated delayed fluorescent material.

In one embodiment, the light-emitting layer includes 70% to 99% by mass of the foregoing nitrogen-containing fused heterocyclic compound or the foregoing nitrogen-containing fused heterocyclic polymer, and 1% to 30% by mass of a light-emitting material.

In one embodiment, the light-emitting layer is prepared by a solution processing method.

The cathode is laminated on the side of the light-emitting layer away from the anode layer. The cathode includes a conductive metal or a metallic oxide, so that the cathode can inject electrons easily into the light-emitting layer or the other functional layer. And, it should be noted that the cathode may be laminated on the substrate, and accordingly, the light-emitting layer is laminated on the side of the cathode away from the substrate and the anode is laminated on the side of the light-emitting layer away from the cathode.

In one embodiment, the material of the cathode is Al, Au, Ag, Ca, Ba, Mg, LiF/Al, MgAg alloy, $BaF_2$/Al, Cu, Fe, Co, Ni, Mn, Pd, Pt or ITO. It should be understood that the material of the cathode is not limited to the above-mentioned materials, and other materials acceptable in the field of electronic devices, such as cadmium oxide, may be selected as needed.

In one embodiment, the absolute value of the difference between the work function of the anode and the LUMO energy level or the valence band energy level of the light-emitting material in the light-emitting layer is smaller than 0.5 eV.

In one embodiment, the absolute value of the difference between the work function of the anode and the LUMO energy level or the valence band energy level of the light-emitting material in the light-emitting layer is smaller than 0.3 eV.

In one embodiment, the absolute value of the difference between the work function of the anode and the LUMO energy level or the valence band energy level of the light-emitting material in the light-emitting layer is smaller than 0.2 eV.

In one embodiment, when the other functional layer is an electron injection layer, an electron transporting layer or a hole blocking layer, the absolute value of the difference between cathode and the LUMO energy level or the valence band energy level of the n type semiconductor material in the other functional layer is smaller than 0.5 eV.

In one embodiment, when the other functional layer is an electron injection layer, an electron transporting layer or a hole blocking layer, the difference between cathode and the LUMO energy level or the valence band energy level of the n type semiconductor material in the other functional layer is smaller than 0.3 eV.

In one embodiment, when the other functional layer is an electron injection layer, an electron transporting layer or a hole blocking layer, the difference between cathode and the LUMO energy level or the valence band energy level of the n type semiconductor material in the other functional layer is smaller than 0.2 eV.

In one embodiment, the cathode is prepared by physical vapor deposition.

In one embodiment, the cathode is prepared by a radio frequency magnetron sputtering, a vacuum thermal evaporation coating or an electron beam (e-beam) evaporation coating.

The other functional layer is a hole injection layer, a hole transporting layer, an electron blocking layer, an electron injection layer, an electron transporting layer or a hole blocking layer. And, it should be noted that when the other functional layer is a hole injection layer, a hole transporting layer or an electron blocking layer, the other functional layer is laminated on the side of the anode near the light-emitting layer and on the side of the light-emitting layer away from the cathode; when the other functional layer is an electron injection layer, an electron transporting layer or a hole injection layer, the other functional layer is laminated on the side of the cathode near the light-emitting layer and on the side of the light-emitting layer away from the anode.

In one embodiment, the other functional layer is a hole transporting layer, laminated on the side of the anode near the light-emitting layer and on the side of the light-emitting layer away from the cathode.

In one embodiment, the other functional layer includes the foregoing nitrogen-containing fused heterocyclic polymer or the foregoing nitrogen-containing fused heterocyclic compound.

In one embodiment, the material of the other functional layer is a material that is acceptable in the field of electronic devices.

In one embodiment, the materials disclosed in WO 2010135519A1, US 20090134784A1 and WO 2011110277A1 can be used as another functional layer of the present embodiment.

An organic electroluminescent device of one embodiment has at least the following advantages:

The foregoing electroluminescent device including the foregoing nitrogen-containing fused heterocyclic polymer or the foregoing nitrogen-containing fused heterocyclic compound allows the foregoing electronic device to have a good stability and a longer lifetime.

The foregoing electronic device can be used in an electronic equipment.

In one embodiment, the electronic equipment is selected from a display equipment, a lighting equipment, a light source, or a sensor.

Due to the better stability and longer lifetime of the foregoing electronic device, the electronic equipment has a good stability and a long lifetime.

The following are specific examples.

In the following examples, the numbers in parentheses after each structural formula only represent the numbering of the compound of the structural formula, and have no other meaning, for example: (5-3) represents compound 5-3.

In the following examples, the numbers below the structural formula in a specific reaction formula only represent the numbering of the compound of the structural formula, and have no other meaning, for example: "5-3-1" represents compound 5-3-1.

Example 1

This example is a preparation process of the nitrogen-containing fused heterocyclic compound 5-3:

The nitrogen-containing fused heterocyclic compound 5-3 has a structural formula as follow:

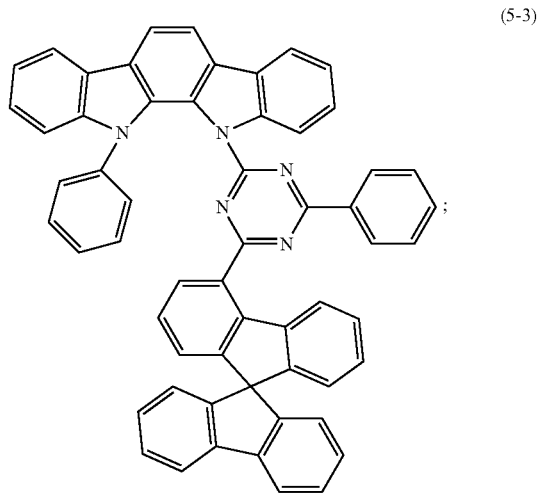 [SMILES: c1ccc(-c2nc(-c3cccc4c3-c3ccccc3C43c4ccccc4-c4ccccc43)nc(-n3c4ccccc4c4ccc5c6ccccc6n(-c6ccccc6)c5c43)n2)cc1]

(5-3)

1)

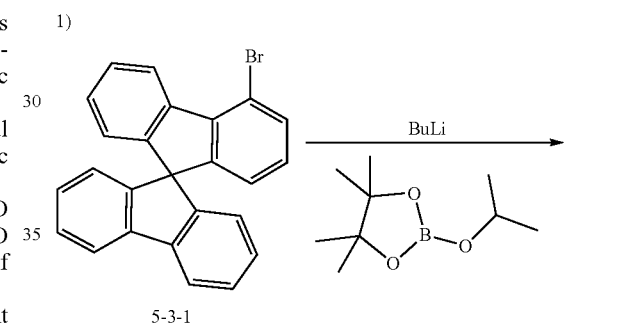

5-3-1

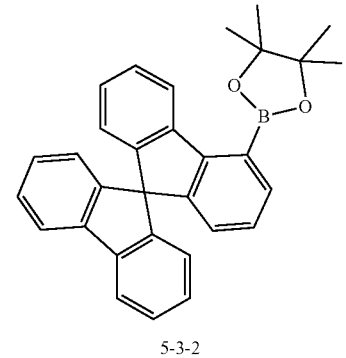

5-3-2

Compound 5-3-1 (19.8 g, 50 mmol) and anhydrous tetrahydrofuran (300 mL) were added to a 500 mL three-necked flask under nitrogen atmosphere. When the temperature was lowered to −78° C., 60 mmol of n-butyllithium was slowly added dropwise. After reacting for 2 hours, 65 mmol of isopropanol pinacol borate was added once. After the reaction temperature rose to room temperature naturally and the reaction was continued for 12 hours, pure water was added to quench the reaction. Most of the solvent was rotary evaporated off, and the reaction solution was extracted with dichloromethane and washed for three times with water. The organic phase was collected, spin dried and recrystallized, with a yield rate of 80%.

2)

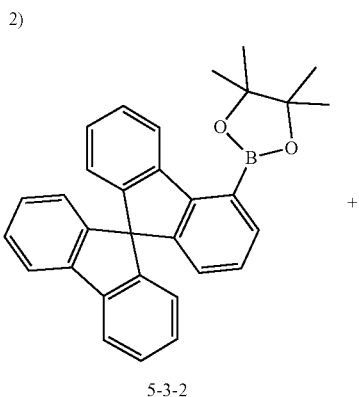

5-3-2

+

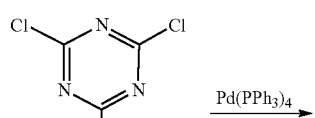

5-3-3

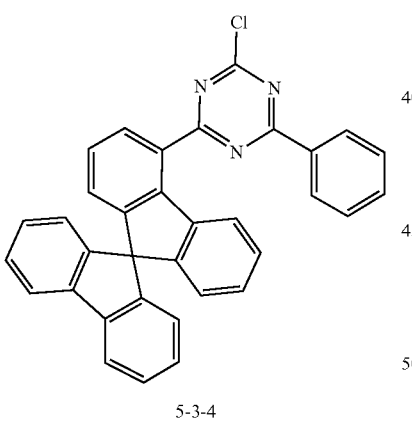

5-3-4

Compound 5-3-2 (13.3 g, 30 mmol), compound 5-3-3 (6.8 g, 30 mmol), sodium carbonate (3.2 g, 30 mmol), tetrakis (triphenylphosphine)palladium (1.8 g, 1.5 mmol), water (10 mL) and 1,4-dioxane (100 mL) were added to a 200 mL three-necked flask and heated at 140° C. for 12 hours under nitrogen atmosphere. The reaction solution was subjected to rotatory evaporation to remove most solvent, dissolved in dichloromethane, and washed for three times with water. The organic solution was collected and purified by silica gel column, with a yield rate of 85%.

3)

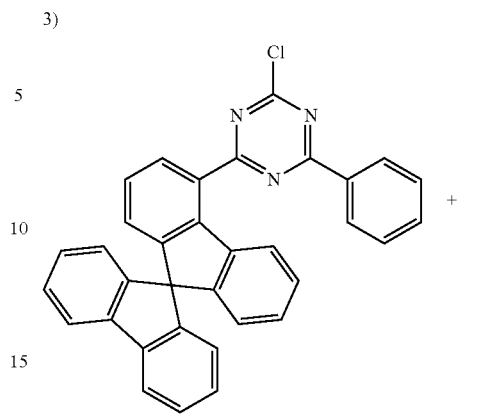

5-3-4

+

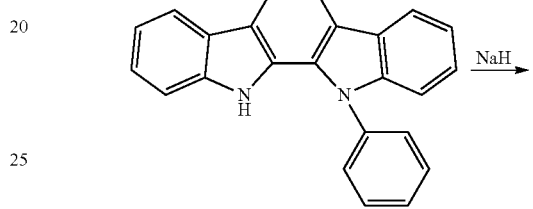

5-3-5

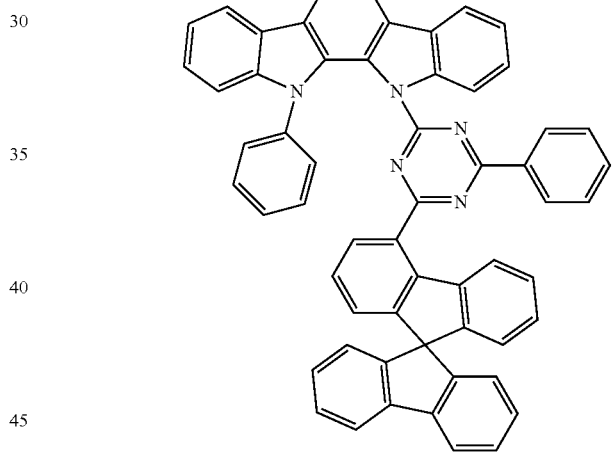

5-3

Compound 5-3-5 (5 g, 15 mmol), sodium hydride (20 mmol) and anhydrous tetrahydrofuran (80 mL) were added to a 200 mL three-necked flask, heated at 60° C. and stirred for 1 hour under nitrogen atmosphere. A solution of compound 5-3-4 (7.6 g, 15 mmol) in tetrahydrofuran was added and the reaction was continued for 12 hours. After the reaction, 500 mL of water was added to the reaction solution which was then extracted with dichloromethane, and washed for three times with water. The organic solution was collected and purified by silica gel column, with a yield rate of 60%.

Example 2

This example is a preparation process of the nitrogen-containing fused heterocyclic compound 6-2:

The nitrogen-containing fused heterocyclic compound 6-2 has a structural formula as follow:

(6-2)

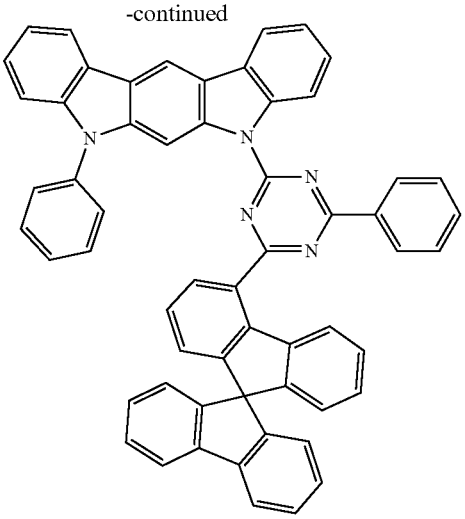

6-2

Compound 6-2-1 (5 g, 15 mmol), sodium hydride (20 mmol) and anhydrous tetrahydrofuran (80 mL) were added to a 200 mL three-necked flask, heated at 60° C. and stirred for 1 hour under nitrogen atmosphere. A solution of compound 5-3-4 (7.2 g, 15 mmol) in tetrahydrofuran was added and the reaction was continued for 12 hours. After the reaction, 500 mL of water was added to the reaction solution which was then extracted with dichloromethane, and washed for three times with water. The organic solution was collected and purified by silica gel column, with a yield rate of 65%.

Example 3

This example is a preparation process of the nitrogen-containing fused heterocyclic compound 7-1:

The nitrogen-containing fused heterocyclic compound 7-1 has a structural formula as follow:

1)

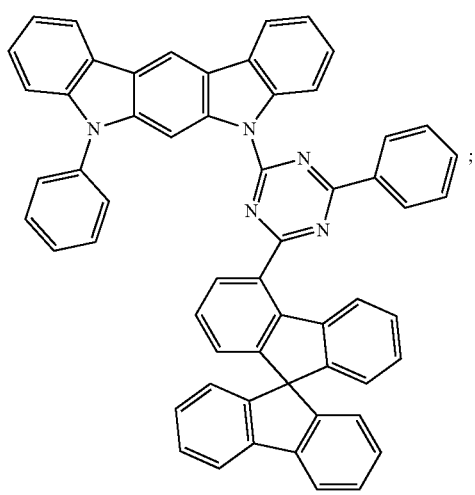

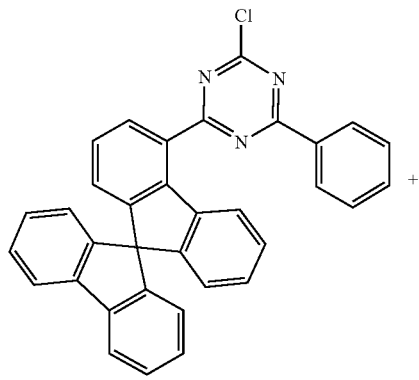

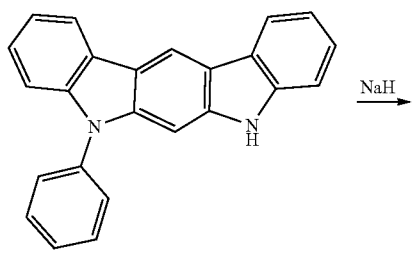

5-3-4

6-2-1

(7-1)

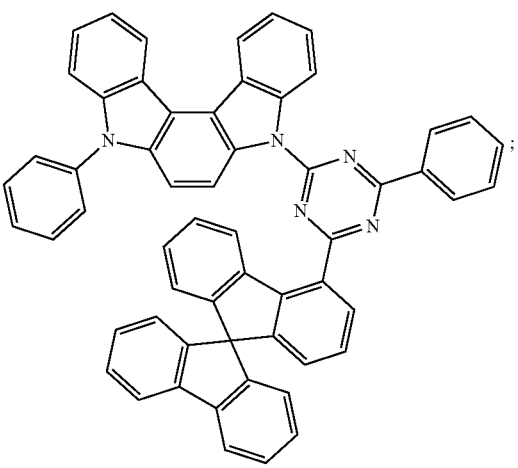

1)

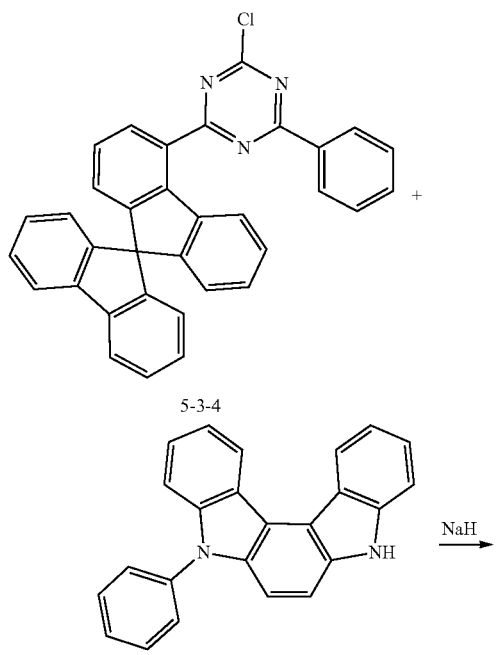

(8-14)

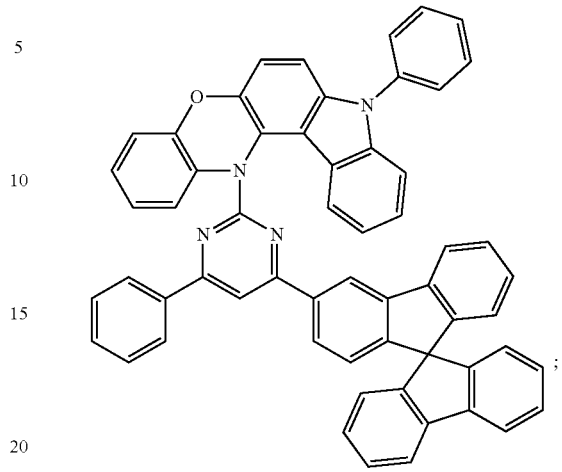

1)

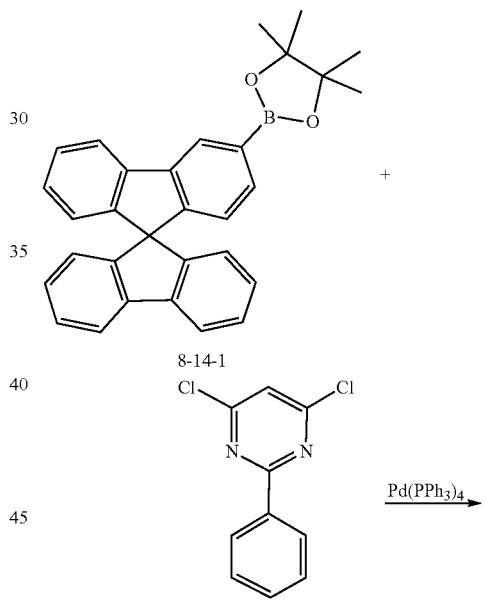

Compound 7-1-1 (5 g, 15 mmol), sodium hydride (20 mmol) and anhydrous tetrahydrofuran (80 mL) were added to a 200 mL three-necked flask, heated at 60° C. and stirred for 1 hour under nitrogen atmosphere. A solution of compound 5-3-4 (7.6 g, 15 mmol) in tetrahydrofuran was added and the reaction was continued for 12 hours. After the reaction, 500 mL of water was added to the reaction solution which was then extracted with dichloromethane, and washed for three times with water. The organic solution was collected and purified by silica gel column, with a yield rate of 70%.

Example 4

This example is a preparation process of the nitrogen-containing fused heterocyclic compound 8-14:

The nitrogen-containing fused heterocyclic compound 8-14 has a structural formula as follow:

Compound 8-14-1 (13.3 g, 30 mmol), compound 8-14-2 (6.8 g, 30 mmol), sodium carbonate (3.2 g, 30 mmol), tetrakis(triphenylphosphine)palladium (1.8 g, 1.5 mmol), water (10 mL) and 1,4-dioxane (100 mL) were added to a 200 mL three-necked flask and heated at 140° C. for 12 hours under nitrogen atmosphere. The reaction solution was subjected to rotatory evaporation to remove most solvent, dissolved in dichloromethane, and washed for three times with water. The organic solution was collected and purified by silica gel column, with a yield rate of 65%.

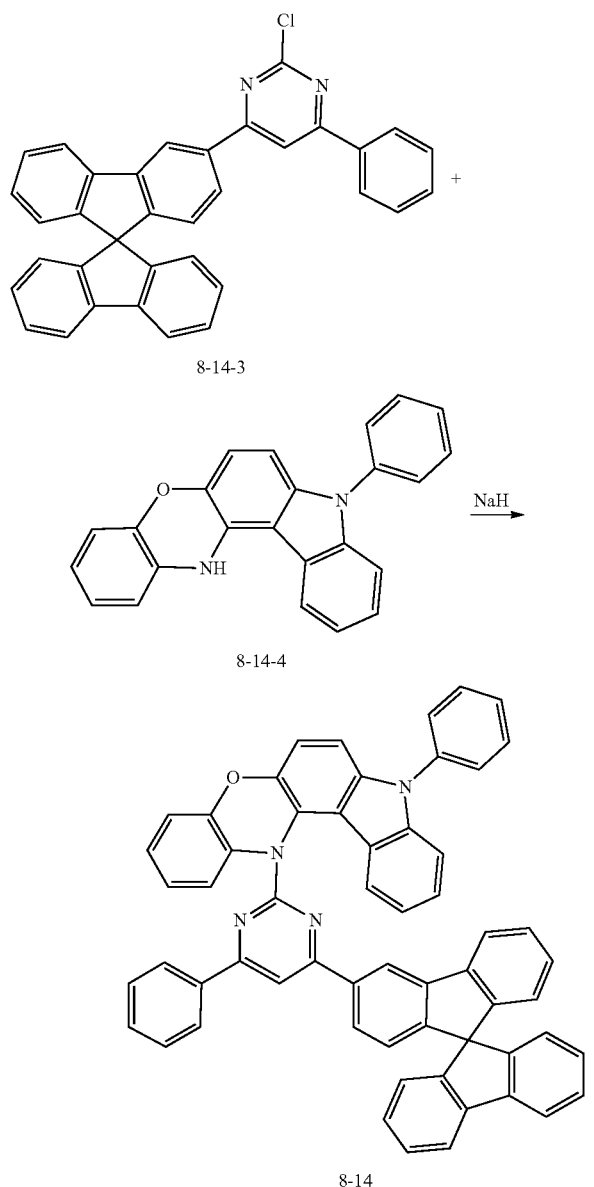

Compound 8-14-4 (5.2 g, 15 mmol), sodium hydride (20 mmol) and anhydrous tetrahydrofuran (80 mL) were added to a 200 mL three-necked flask, heated at 60° C. and stirred for 1 hour under nitrogen atmosphere. A solution of compound 8-14-3 (7.6 g, 15 mmol) in tetrahydrofuran was added and the reaction was continued for 12 hours. After the reaction, 500 mL of water was added to the reaction solution which was then extracted with dichloromethane, and washed for three times with water. The organic solution was collected and purified by silica gel column, with a yield rate of 60%.

Example 5

This example is a preparation process of the nitrogen-containing fused heterocyclic compound 9-1:

The nitrogen-containing fused heterocyclic compound 9-1 has a structural formula as follow:

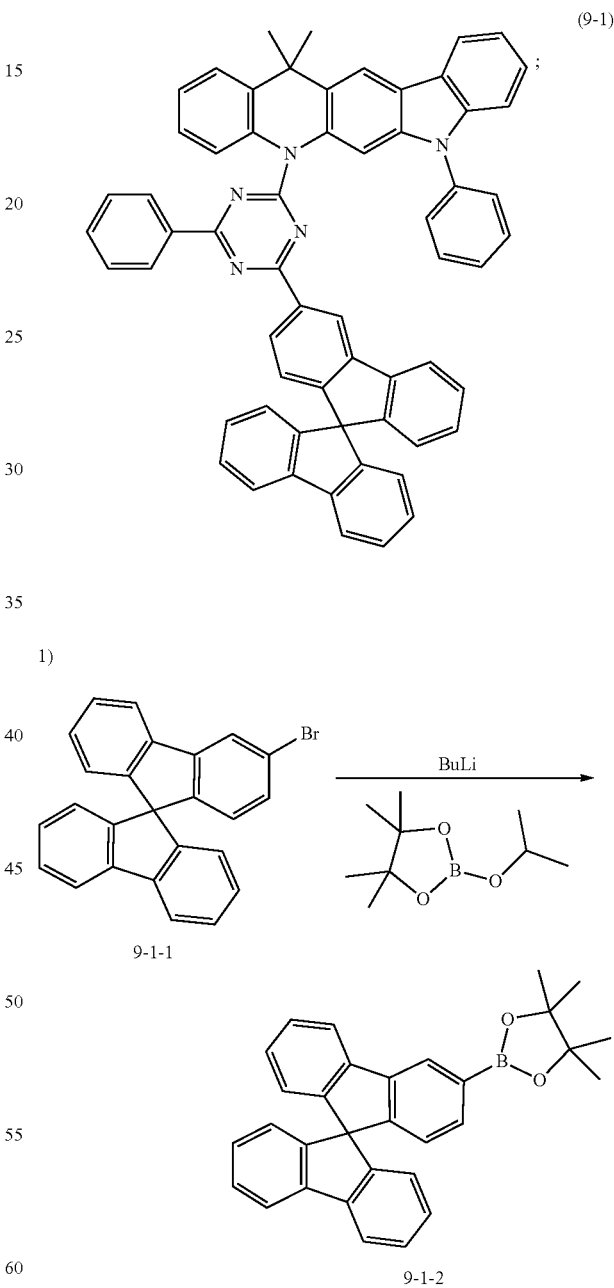

Compound 9-1-1 (19.8 g, 50 mmol) and anhydrous tetrahydrofuran (300 mL) were added to a 500 mL three-necked flask under nitrogen atmosphere. When the temperature was lowered to −78° C., 60 mmol of n-butyllithium was slowly added dropwise. After reacting for 2 hours, 65 mmol of isopropanol pinacol borate was added once. After the reaction temperature rose to room temperature naturally and the reaction was continued for 12 hours, pure water was added to quench the reaction. Most of the solvent was rotary evaporated off, and the reaction solution was extracted with dichloromethane and washed for three times with water. The organic solution was collected, spin dried and recrystallized, with a yield rate of 85%.

2)

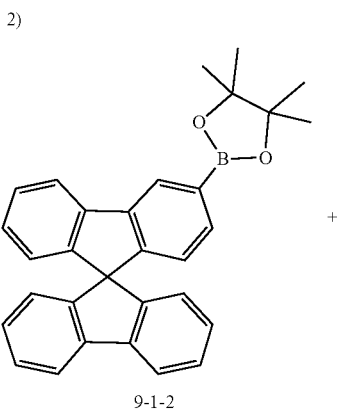

9-1-2

+

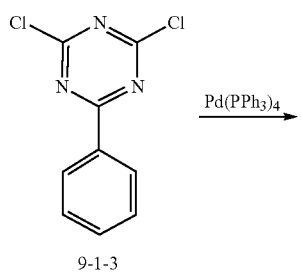

9-1-3

Pd(PPh₃)₄ →

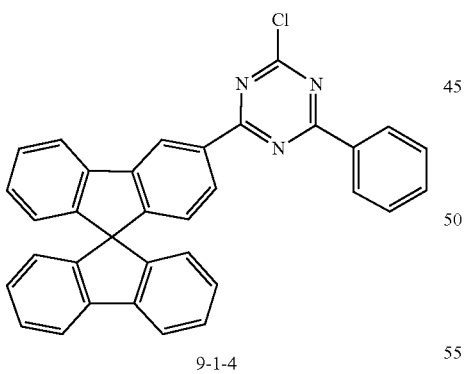

9-1-4

Compound 9-1-2 (13.3 g, 30 mmol), compound 9-1-3 (6.8 g, 30 mmol), sodium carbonate (3.2 g, 30 mmol), tetrakis(triphenylphosphine)palladium (1.8 g, 0.5 mmol), water (10 mL) and 1,4-dioxane (100 mL) were added to a 200 mL three-necked flask and heated at 140° C. for 12 hours under nitrogen atmosphere. The reaction solution was subjected to rotatory evaporation to remove most solvent, dissolved in dichloromethane, and washed for three times with water. The organic solution was collected and purified by silica gel column, with a yield rate of 80%.

3)

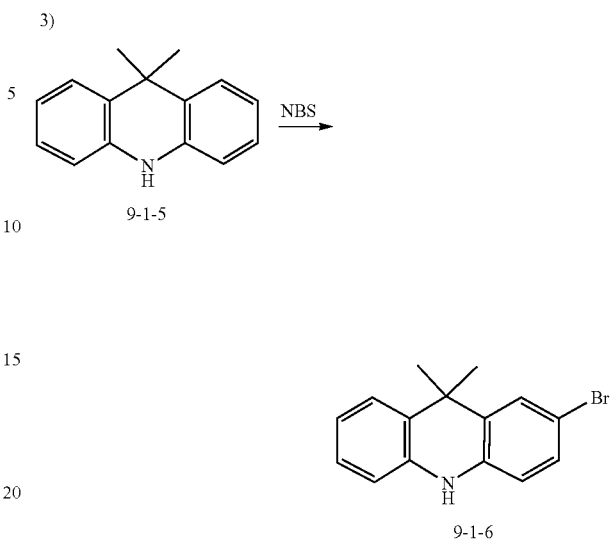

Compound 9-1-5 (21 g, 100 mmol) and N,N-dimethylformamide (100 mL) were added to a 250 mL single-neck flask, and 100 mmol of NBS in N,N-dimethyl was added dropwise in an ice bath. The reaction solution was stirred for 12 hours in the dark, and poured into 500 mL of water, suction filtered, and recrystallized, with a yield rate of 90%.

4)

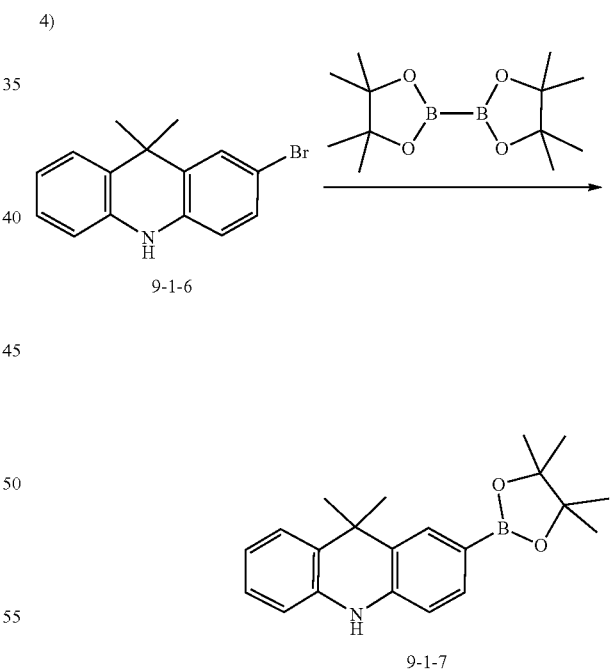

Compound 9-1-6 (17.3 g, 60 mmol), pinacol diborate (15.2 g, 60 mmol), Pd(dppf)Cl2 (3 mmol), potassium acetate (60 mmol) and 1,4-dioxane (100 mL) were added to a 250 mL two-necked flask, heated at 110° C. and stirred for 12 hours. After the reaction, the reaction solution was poured into 500 mL of water, suction filtered. The filter residue was collected and purified by silica gel column, with a yield rate of 80%.

5)

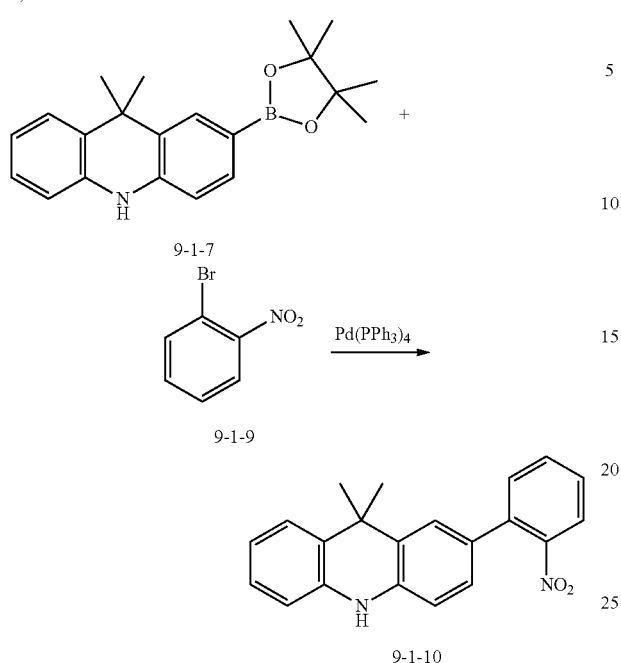

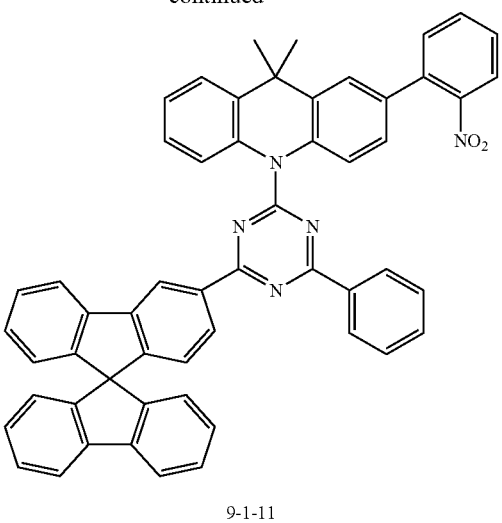

9-1-11

Compound 9-1-7 (13.4 g, 40 mmol), compound 9-1-9 (8 g, 40 mmol), tetrakis(triphenylphosphine)palladium (2.3 g, 2 mmol), tetrabutylammonium bromide (2.6 g, 8 mmol), sodium hydroxide (3.2 g, 80 mmol), water (10 mL) and toluene (100 mL) were added to a 250 mL three-necked flask, heated at 80° C. and stirred for 12 hours under nitrogen atmosphere. The reaction solution was subjected to rotatory evaporation to remove most solvent, dissolved in dichloromethane, and washed for three times with water. The organic solution was collected and purified by silica gel column, with a yield rate of 75%.

Compound 9-1-10 (6.6 g, 20 mmol), sodium hydride (30 mmol) and anhydrous tetrahydrofuran (80 mL) were added to a 200 mL three-necked flask, heated at 60° C. and stirred for 1 hour under nitrogen atmosphere. A solution of compound 9-1-4 (10.1 g, 20 mmol) in tetrahydrofuran was added and the reaction was continued for 12 hours. After the reaction, 300 mL of water was added to the reaction solution which was then extracted with dichloromethane, and washed for three times with water. The organic solution was collected and purified by silica gel column, with a yield rate of 65%.

6)

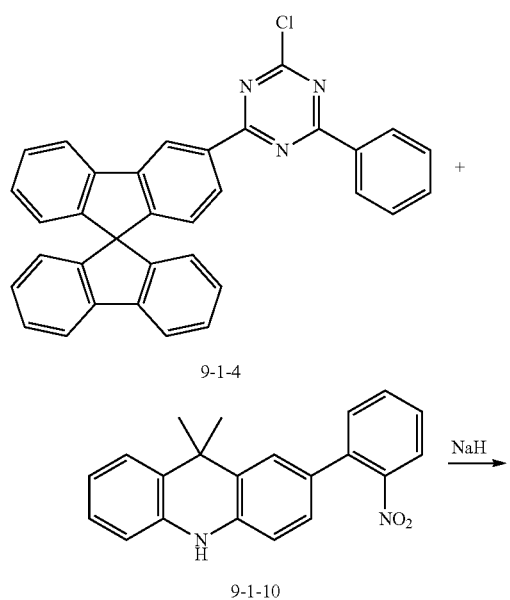

7)

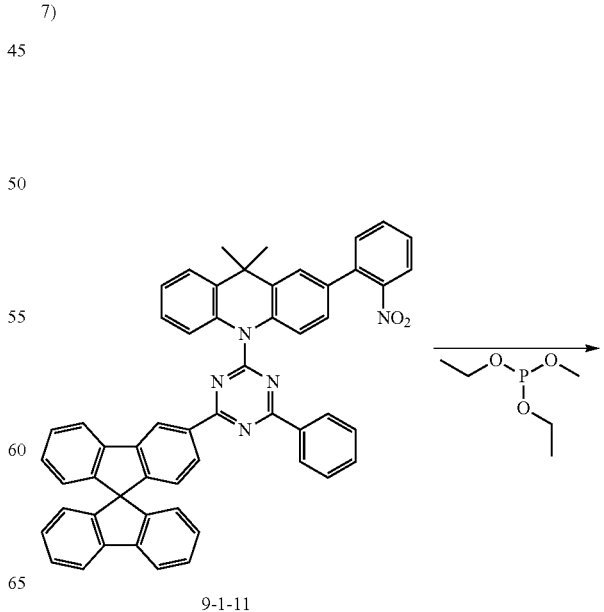

-continued

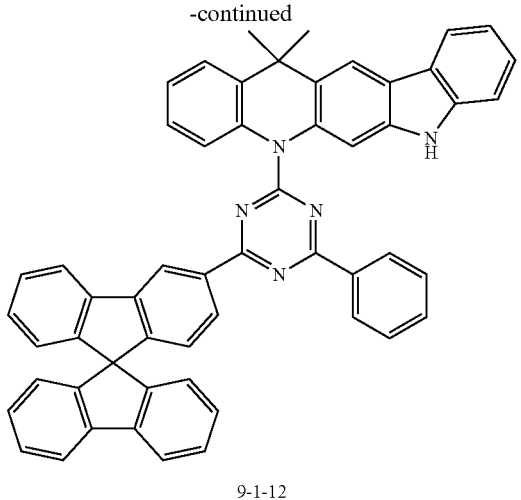

9-1-12

Compound 9-1-11 (8 g, 10 mmol) and triethylphosphorus (20.2 g, 50 mmol) were added to a 150 mL two-necked flask, heated at 190° C. and stirred for 12 hours under nitrogen atmosphere. After the reaction, the reaction solution was evaporated to remove most of the solvent under reduced pressure, dissolved in dichloromethane and washed with water for three times. The organic solution was collected and purified by silica gel column, with a yield rate of 85%.

8)

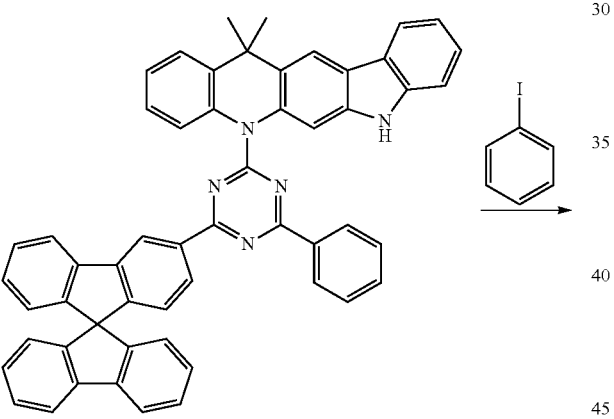

9-1-12

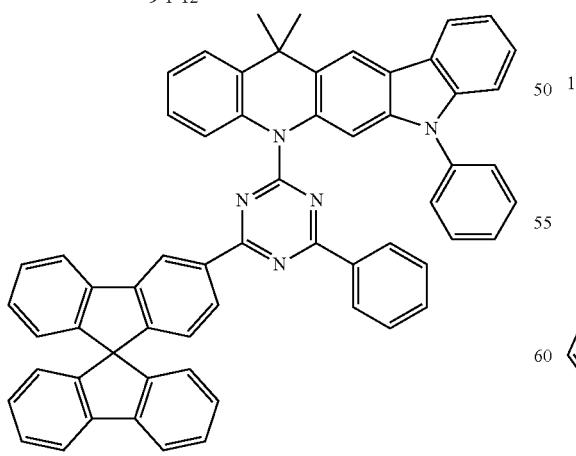

9-1

Compound 9-1-12 (4.6 g, 6 mmol), iodobenzene (2 g, 10 mmol), copper powder (0.13 g, 2 mmol), potassium carbonate (5.5 g, 40 mmol), 18-crown-6 (0.53 g, 1 mmol) and o-dichlorobenzene (50 mL) were added to a 100 mL two-neck flask, heated at 150° C. and stirred for 24 hours under nitrogen atmosphere. After the reaction, the reaction solution was subjected to evaporation under reduced pressure to remove most solvent, dissolved in dichloromethane and washed with water for three times. The organic solution was collected and purified by silica gel column, with a yield rate of 70%.

Example 6

This example is a preparation process of the nitrogen-containing fused heterocyclic compound 10-6:

The nitrogen-containing fused heterocyclic compound 10-6 has a structural formula as follow:

(10-6)

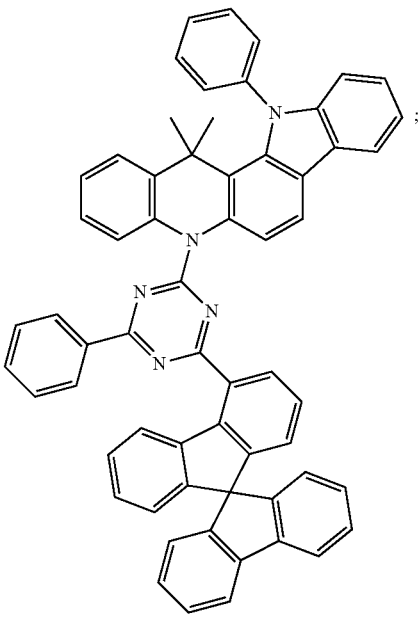

1)

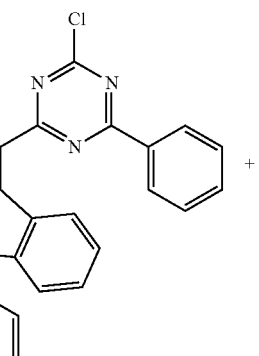

5-3-4

+

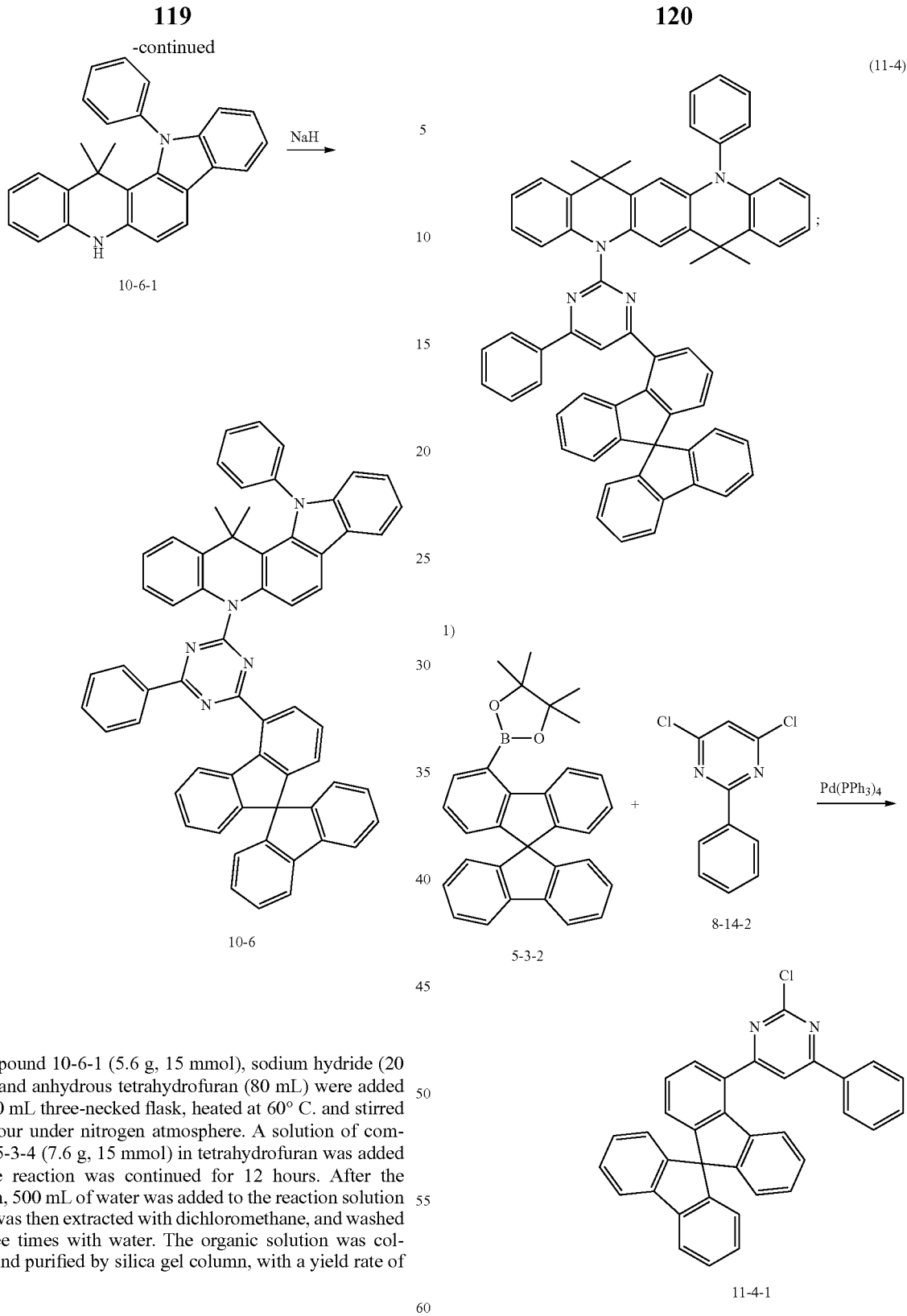

Compound 10-6-1 (5.6 g, 15 mmol), sodium hydride (20 mmol) and anhydrous tetrahydrofuran (80 mL) were added to a 200 mL three-necked flask, heated at 60° C. and stirred for 1 hour under nitrogen atmosphere. A solution of compound 5-3-4 (7.6 g, 15 mmol) in tetrahydrofuran was added and the reaction was continued for 12 hours. After the reaction, 500 mL of water was added to the reaction solution which was then extracted with dichloromethane, and washed for three times with water. The organic solution was collected and purified by silica gel column, with a yield rate of 80%.

Example 7

This example is a preparation process of the nitrogen-containing fused heterocyclic compound 11-4:

The nitrogen-containing fused heterocyclic compound 11-4 has a structural formula as follow:

Compound 5-3-2 (13.3 g, 30 mmol), compound 8-14-2 (6.8 g, 30 mmol), tetrakis(triphenylphosphine)palladium (3.2 g, 30 mmol), tetrakis(triphenylphosphine)palladium (1.8 g, 1.5 mmol), water (10 mL) and 1,4-dioxane (100 mL) were added to a 200 mL three-necked flask, heated at 140° C. and stirred for 12 hours under nitrogen atmosphere. The reaction solution was subjected to rotatory evaporation to remove most solvent and dissolved in dichloromethane, and washed for three times with water. The organic solution was collected and purified by silica gel column, with a yield rate of 70%.

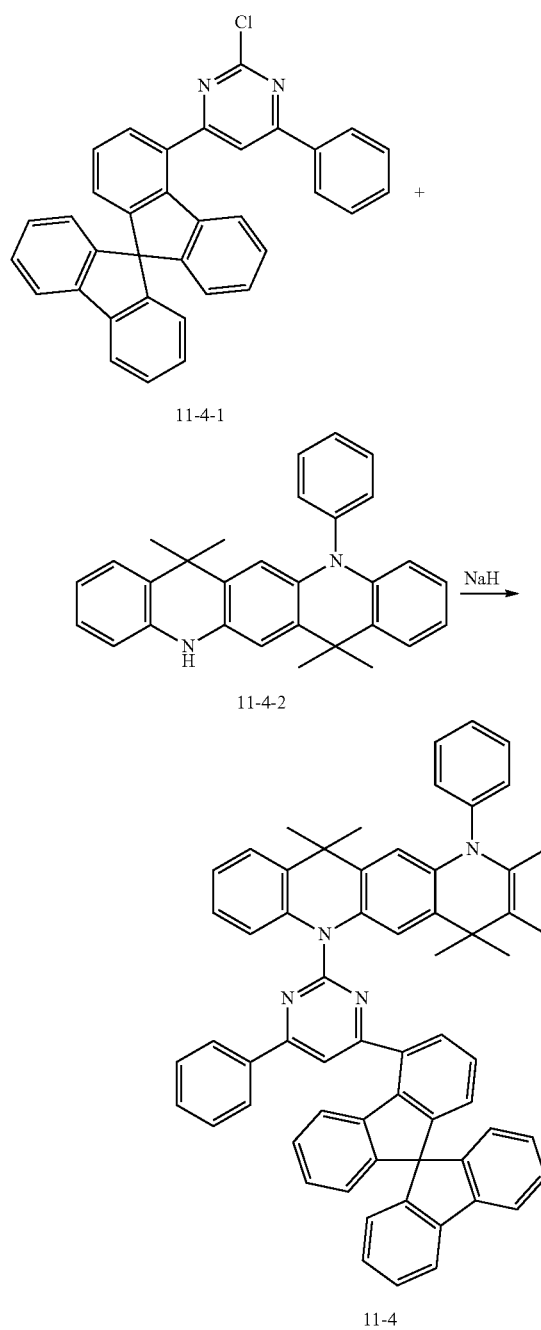

Compound 11-14-2 (6.3 g, 15 mmol), sodium hydride (20 mmol) and anhydrous tetrahydrofuran (80 mL) were added to a 200 mL three-necked flask, heated at 60° C. and stirred for 1 hour under nitrogen atmosphere. A solution of compound 11-14-1 (7.6 g, 15 mmol) in tetrahydrofuran was added and the reaction was continued for 12 hours. After the reaction, 500 mL of water was added to the reaction solution which was then extracted with dichloromethane, and washed for three times with water. The organic solution was collected and purified by silica gel column, with a yield rate of 70%.

Example 8

This example is a preparation process of the nitrogen-containing fused heterocyclic compound 12-1:

The nitrogen-containing fused heterocyclic compound 12-1 has a structural formula as follow:

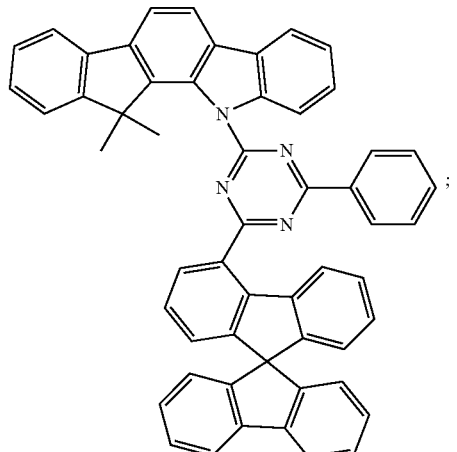

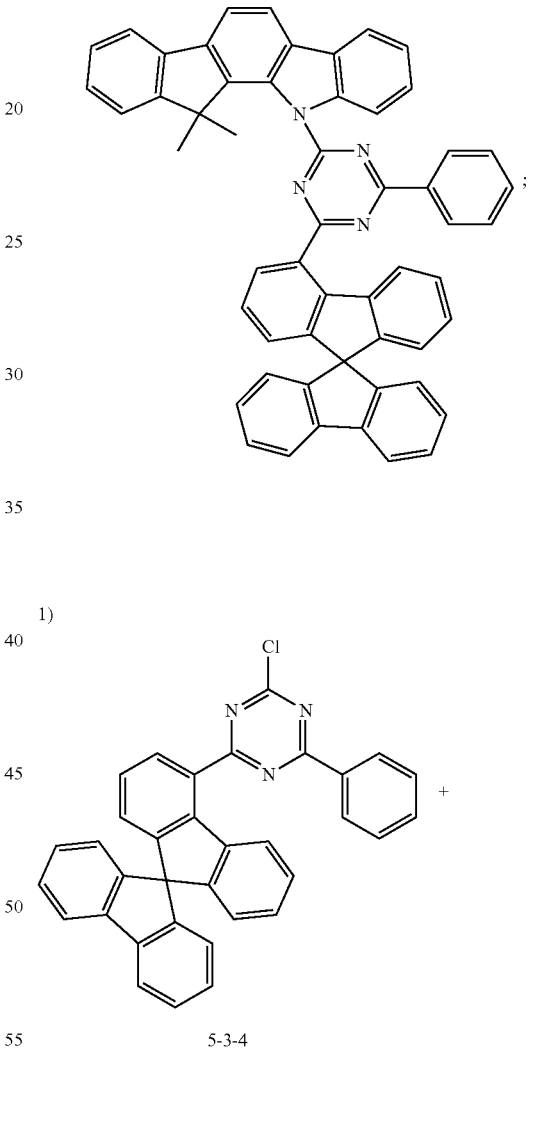

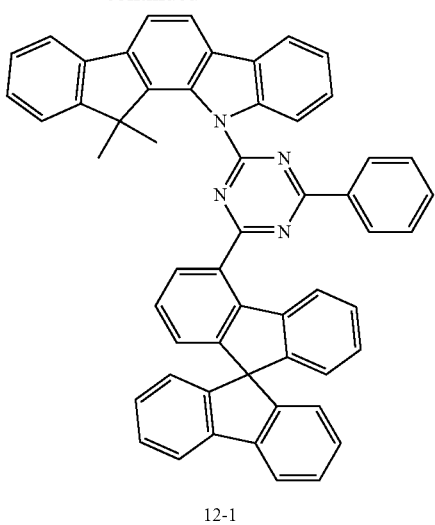

12-1

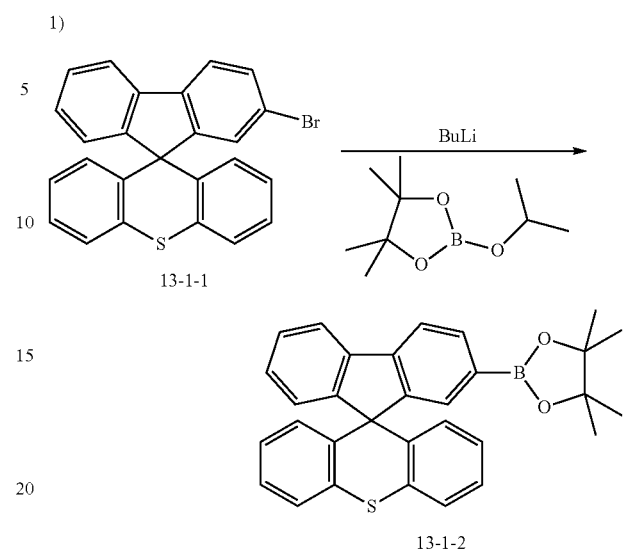

13-1-1

Compound 12-1-1 (4.2 g, 15 mmol), sodium hydride (20 mmol) and anhydrous tetrahydrofuran (80 mL) were added to a 200 mL three-necked flask, heated at 60° C. and stirred for 1 hour under nitrogen atmosphere. A solution of compound 5-3-4 (7.6 g, 15 mmol) in tetrahydrofuran was added and the reaction was continued for 12 hours. After the reaction, 500 mL of water was added to the reaction solution which was then extracted with dichloromethane, and washed for three times with water. The organic solution was collected and purified by silica gel column, with a yield rate of 70%.

Example 9

This example is a preparation process of the nitrogen-containing fused heterocyclic compound 13-1:

The nitrogen-containing fused heterocyclic compound 13-1 has a structural formula as follow:

(13-1)

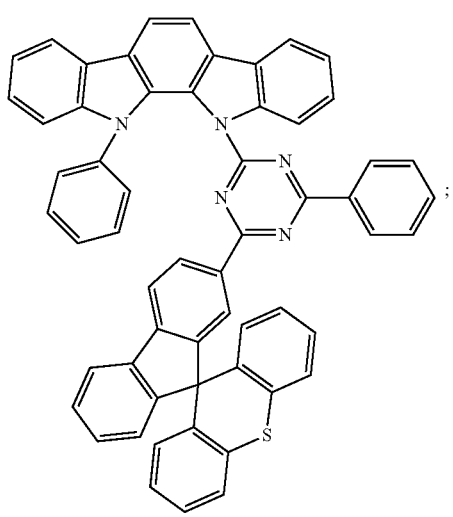

1)

Compound 13-1-1 (21.4 g, 50 mmol) and 300 mL of anhydrous tetrahydrofuran were added to a 500 mL three-necked flask under nitrogen atmosphere. When the temperature was lowered to −78° C., 60 mmol of n-butyllithium was slowly added dropwise. After reacting for 2 hours, 65 mmol of isopropanol pinacol borate was added once. After the reaction temperature rose to room temperature naturally and the reaction was continued for 12 hours, pure water was added to quench the reaction. Most of the solvent was rotary evaporated off, and the reaction solution was extracted with dichloromethane and washed for three times with water. The organic phase was collected, spin dried and recrystallized, with a yield rate of 85%.

2)

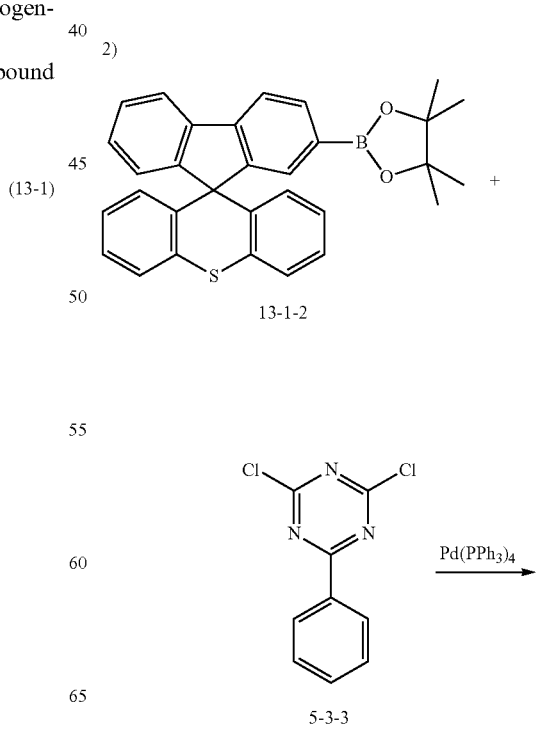

5-3-3

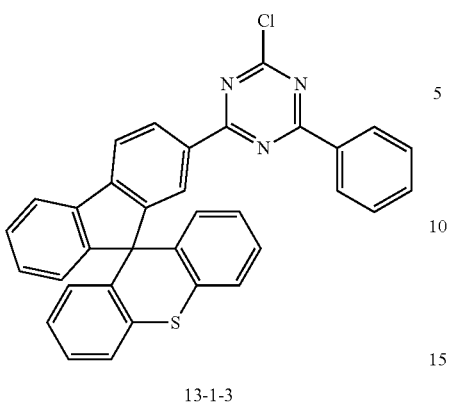

13-1-3

Compound 13-1-2 (14.2 g, 30 mmol), compound 5-3-3 (6.8 g, 30 mmol), sodium carbonate (3.2 g, 30 mmol), tetrakis(triphenylphosphine)palladium (1.8 g, 1.5 mmol), water (10 mL) and 1,4-dioxane (100 mL) were added to a 200 mL three-necked flask and heated at 140° C. for 12 hours under nitrogen atmosphere. The reaction solution was subjected to rotatory evaporation to remove most solvent, dissolved in dichloromethane, and washed for three times with water. The organic solution was collected and purified by silica gel column, with a yield rate of 70%.

3)

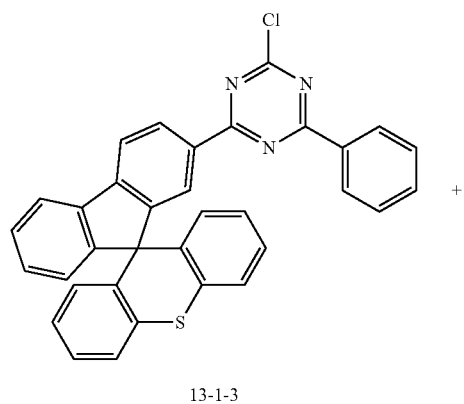

13-1-3

+

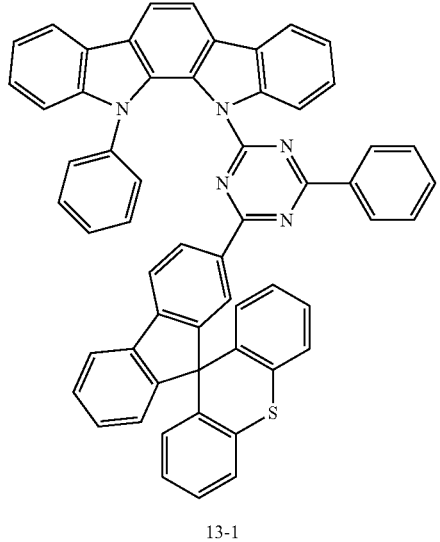

13-1

Compound 5-3-5 (5 g, 15 mmol), sodium hydride (20 mmol) and anhydrous tetrahydrofuran (80 mL) were added to a 200 mL three-necked flask, heated at 60° C. and stirred for 1 hour under nitrogen atmosphere. A solution of compound 13-1-3 (8.1 g, 15 mmol) in tetrahydrofuran was added and the reaction was continued for 12 hours. After the reaction, 500 mL of water was added to the reaction solution which was then extracted with dichloromethane, and washed for three times with water. The organic solution was collected and purified by silica gel column, with a yield rate of 65%.

Example 10

This example is a preparation process of the nitrogen-containing fused heterocyclic compound 14-3:

The nitrogen-containing fused heterocyclic compound 14-3 has a structural formula as follow:

(14-3)

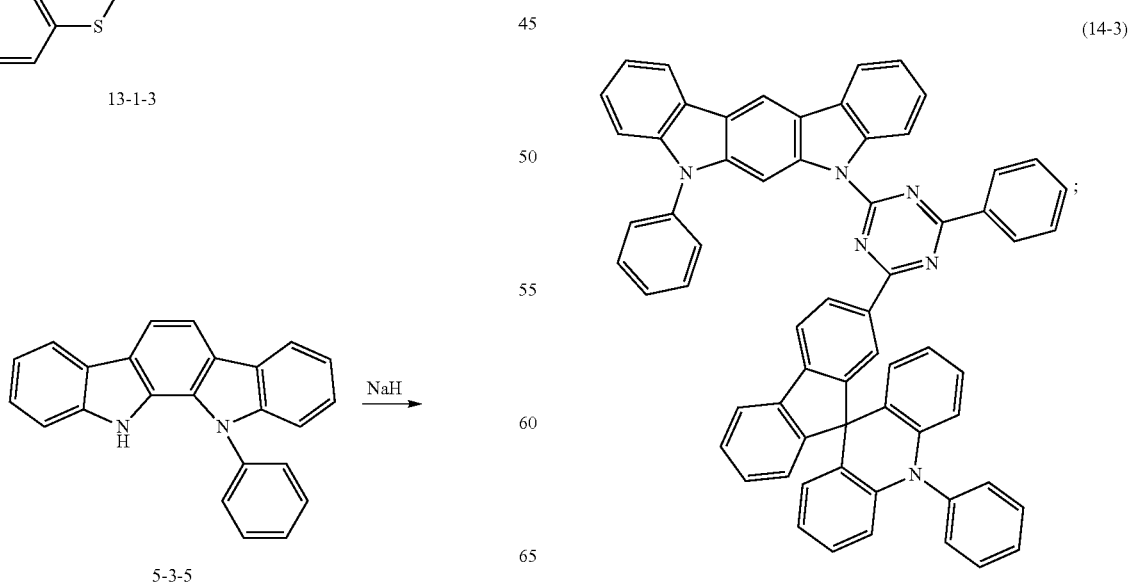

5-3-5

1)

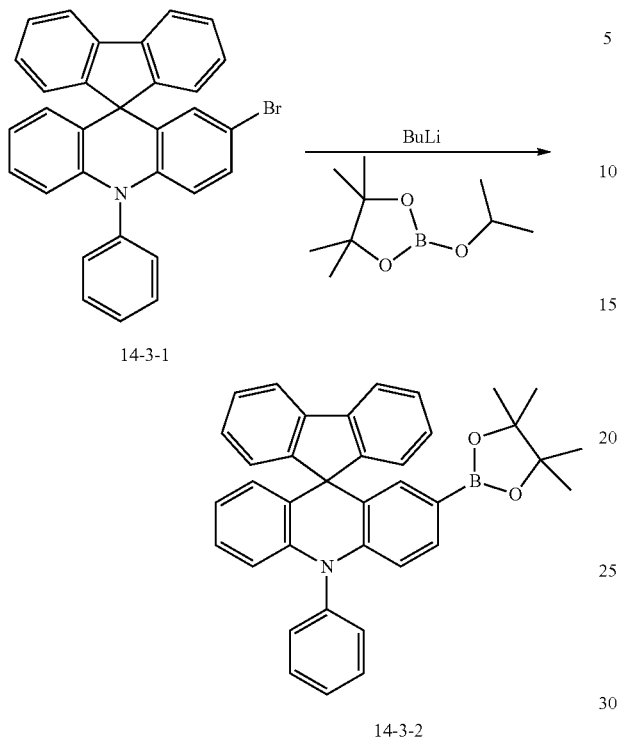

Compound 14-3-1 (24.3 g, 50 mmol) and anhydrous tetrahydrofuran (300 mL) were added to a 500 mL three-necked flask under nitrogen atmosphere. When the temperature was lowered to −78° C., 60 mmol of n-butyllithium was slowly added dropwise. After 2-hour reaction, 65 mmol of isopropanol pinacol borate was added once. After the reaction temperature rose to room temperature naturally and the reaction was continued for 12 hours, pure water was added to quench the reaction. Most of the solvent was rotary evaporated off, and the reaction solution was extracted with dichloromethane and washed for three times with water. The organic phase was collected, spin dried and recrystallized, with a yield rate of 80%.

2)

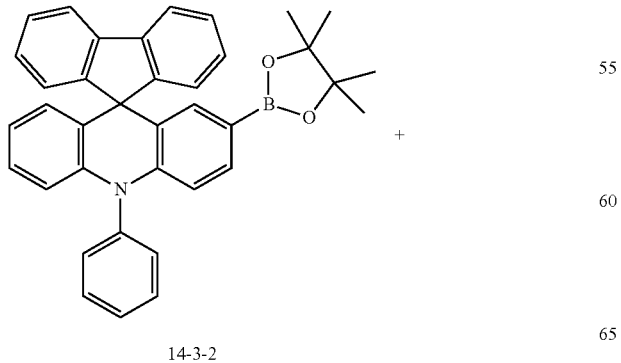

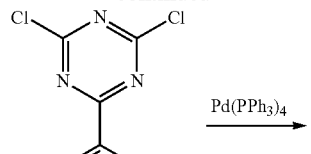

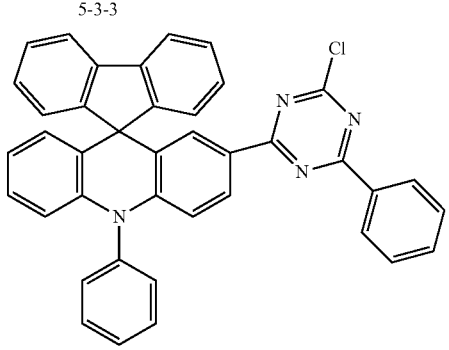

Compound 14-3-2 (16.0 g, 30 mmol), compound 5-3-3 (6.8 g, 30 mmol), sodium carbonate (3.2 g, 30 mmol), tetrakis(triphenylphosphine)palladium (1.8 g, 1.5 mmol), water (10 mL) and 1,4-dioxane (100 mL) were added to a 200 mL three-necked flask and heated at 140° C. for 12 hours under nitrogen atmosphere. The reaction solution was subjected to rotatory evaporation to remove most solvent, dissolved in dichloromethane, and washed for three times with water. The organic solution was collected and purified by silica gel column, with a yield rate of 65%.

3)

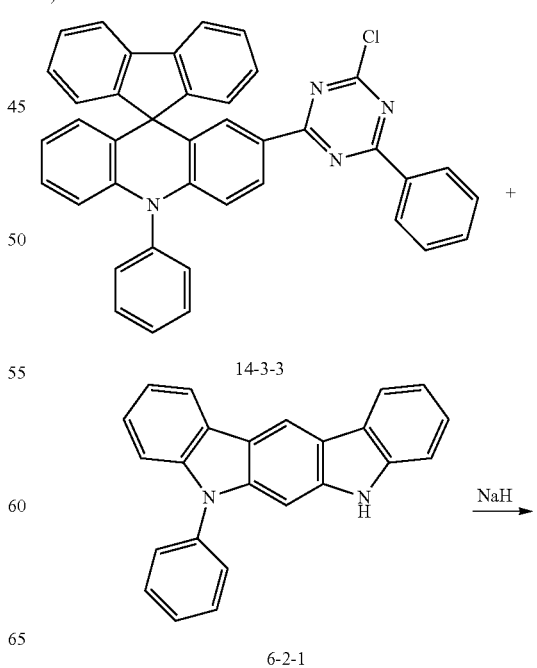

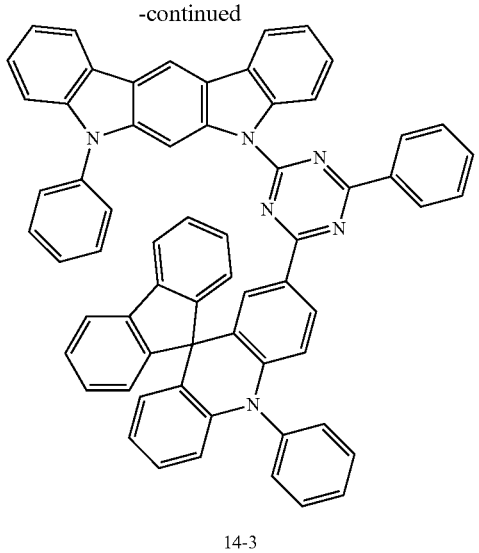

14-3

Compound 6-2-1 (5 g, 15 mmol), sodium hydride (20 mmol) and anhydrous tetrahydrofuran (80 mL) were added to a 200 mL three-necked flask, heated at 60° C. and stirred for 1 hour under nitrogen atmosphere. A solution of compound 14-3-3 (9.0 g, 15 mmol) in tetrahydrofuran was added and the reaction was continued for 12 hours. After the reaction, 500 mL of water was added to the reaction solution which was then extracted with dichloromethane, and washed for three times with water. The organic solution was collected and purified by silica gel column, with a yield rate of 60%.

Example 11

This example is a preparation process of the nitrogen-containing fused heterocyclic compound 15-2:

The nitrogen-containing fused heterocyclic compound 15-2 has a structural formula as follow:

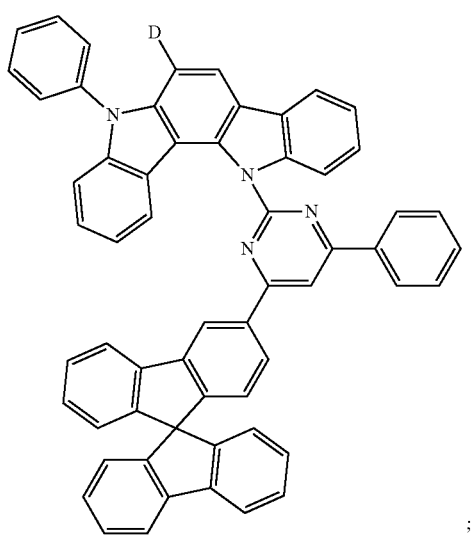

(15-2)

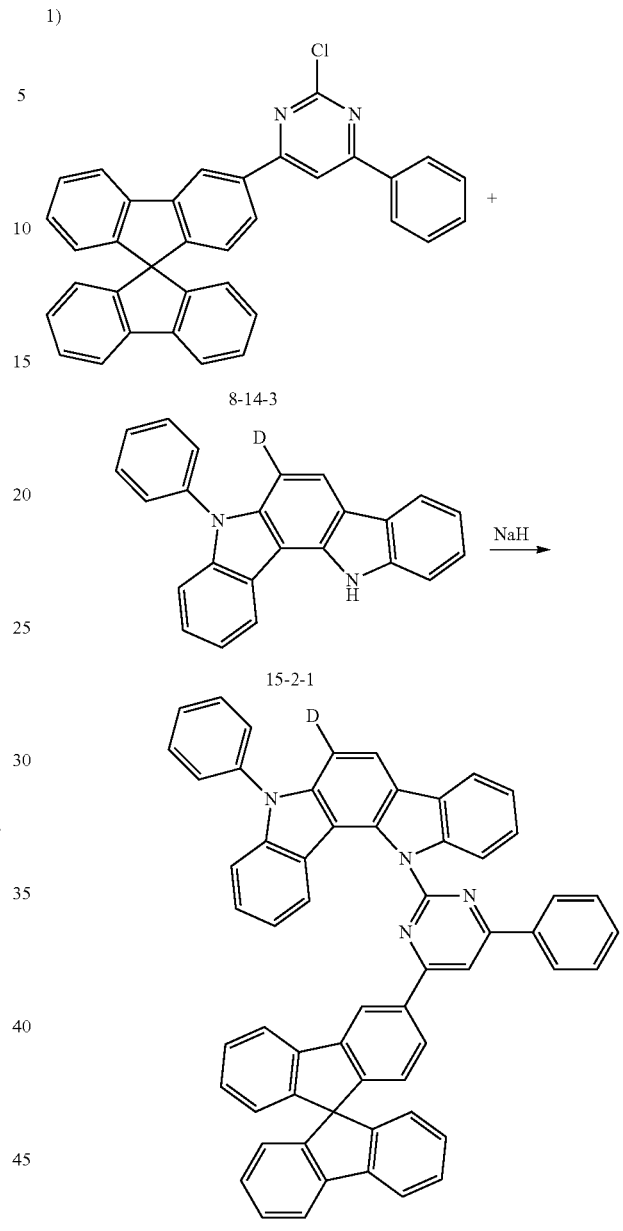

Compound 15-2-1 (5.0 g, 15 mmol), sodium hydride (20 mmol) and anhydrous tetrahydrofuran (80 mL) were added to a 200 mL three-necked flask, heated at 60° C. and stirred for 1 hour under nitrogen atmosphere. A solution of compound 5-3-4 (7.6 g, 15 mmol) in tetrahydrofuran was added and the reaction was continued for 12 hours. After the reaction, 500 mL of water was added to the reaction solution which was then extracted with dichloromethane, and washed for three times with water. The organic solution was collected and purified by silica gel column, with a yield rate of 65%.

Test:

1. A solubility (mg/mL) of compounds of Examples 1 to 11 and CBP, i.e., 4,4'-bis(9H-carbazol-9-yl)biphenyl, in toluene, xylene and chloroform was measured. The test temperature was 25° C. The results are shown in Table 1.

Table 1 shows the solubility of compounds of Examples 1 to 11 and CBP in toluene, xylene and chloroform.

TABLE 1

|  | Toluene (mg/mL) | Xylene (mg/mL) | Chloroform (mg/mL) |
|---|---|---|---|
| Example 1 | 250 | 320 | 410 |
| Example 2 | 205 | 256 | 294 |
| Example 3 | 200 | 243 | 285 |
| Example 4 | 305 | 362 | 430 |
| Example 5 | 330 | 376 | 445 |
| Example 6 | 350 | 392 | 460 |
| Example 7 | 362 | 405 | 473 |
| Example 8 | 400 | 452 | 510 |
| Example 9 | 285 | 354 | 434 |
| Example 10 | 220 | 284 | 344 |
| Example 11 | 268 | 313 | 374 |
| CBP | 130 | 153 | 185 |

It can be seen from Table 1 that the solubility of the compounds of Examples 1 to 11 in toluene is greater than 200 mg/L, which is better than that of CBP in toluene; the solubility of the compounds of Examples 1 to 11 in xylene is greater than 240 mg/L, which is better than that of CBP in xylene; the solubility of the compounds of Examples 1-11 in chloroform is greater than 300 mg/L, which is better than that of CBP in chloroform. The compounds of Examples 1 to 11 were found to have a good solubility in toluene, xylene and chloroform.

2. The HOMO, LUMO, $T_1$, and $S_1$ of the compounds of Examples 1 to 11, HATCH (2,3,6,7,10,11-hexacyano-1,4,5,8,9,12-hexazabenzophenanthrene), NPB (N,N'-bis(1-naphthyl)-N,N'-diphenyl-1,1'-biphenyl-4-4'-diamine), TCTA (4,4',4"-Tri(9-carbazoyl)triphenylamine), B3PYMPM (4,6-bis(3,5-di(3-pyridyl)phenyl)-2-methylpyrimidine) and Ir(piq)2acac (Bis(1-phenylisoquinoline)(acetylacetonate) iridium (III)) were measured, which are shown in table 2.

The energy level of the compounds can be calculated by using TD-DFT (time-dependent density functional theory) by Gaussian03W (Gaussian Inc.), the specific simulation methods of which can be found in WO2011141110. Specifically, the geometry of the compounds is optimized by density functional method "Ground State/DFT/Default Spin/B3LYP" and basis set "6-31G (d)" (Charge 0/Spin Singlet), and the energy structure of the compounds is calculated by TD-DFT (time-density functional theory) to obtain "TD-SCF/DFT/Default Spin/B3PW91" and the basis set "6-31G (d)" (Charge 0/Spin Singlet). The HOMO and the LUMO levels are calculated using the following calibration formulas (1) and (2), with S1 and T1 being used directly.

$$HOMO(eV)=((HOMO(G)\times 27.212)-0.9899)/1.1206 \quad \text{calibration formula (1),}$$

wherein HOMO(G) is the direct calculation result of Gaussian 03W, in units of Hartree.

$$LUMO(eV)=((LUMO(G)\times 27.212)-2.0041)/1.385 \quad \text{calibration formula (2),}$$

wherein LUMO(G) is the direct calculation result of Gaussian 03W, in units of Hartree.

Table 2 shows the HOMO, LUMO, $T_1$, and $S_1$ of the compounds of Examples 1 to 11, HATCH, NPB, TCTA, B3PYMPM, and Ir(piq)2acac.

TABLE 2

|  | HOMO (eV) | LUMO (eV) | $T_1$ (eV) | $S_1$ (eV) |
|---|---|---|---|---|
| Example 1 | −5.67 | −2.91 | 2.68 | 2.80 |
| Example 2 | −5.64 | −2.83 | 2.78 | 2.97 |
| Example 3 | −5.57 | −2.88 | 2.70 | 2.83 |
| Example 4 | −5.43 | −2.66 | 2.73 | 2.89 |
| Example 5 | −5.36 | −2.95 | 2.33 | 2.35 |
| Example 6 | −5.93 | −2.71 | 2.82 | 3.19 |
| Example 7 | −4.81 | −2.88 | 1.89 | 1.91 |
| Example 8 | −5.73 | −3.02 | 2.69 | 2.80 |
| Example 9 | −5.64 | −2.91 | 2.63 | 2.79 |
| Example 10 | −5.43 | −2.75 | 2.60 | 2.84 |
| Example 11 | −5.41 | −2.81 | 2.70 | 2.72 |
| HATCH | −9.04 | −5.08 | 2.32 | 3.17 |
| NPB | −6.72 | −2.85 | 2.97 | 3.46 |
| TCTA | −5.34 | −2.20 | 2.73 | 3.42 |
| B3PYMPM | −5.33 | −2.20 | 2.72 | 3.28 |
| Ir(piq)2acac | −5.21 | −2.71 | 2.18 | 2.38 |

As can be seen from Table 2, the compounds of Examples 1 to 11 have a small difference in energy level between HOMO and LUMO, indicating that the compounds of Examples 1 to 11 have a good stability, while the compounds of Examples 1 to 11 have a small EST, indicating that materials including the compounds of Examples 1 to 11 have a high luminous efficiency.

3. The effects of each of the nitrogen-containing fused heterocyclic compounds of Examples 1, 2, 3, 4, 6, 8, 11, and CBP as a host material of the organic electroluminescent device (OLED) on the luminous efficiency and lifetime values of the OLEDs were measured. The current-voltage (J-V) characteristics of the OLED devices are characterized by a characterization equipment, while the lifetime values of the OLED devices were recorded, and the lifetime is represented by T90@1000 nits which is relative to the value of RefOLED1. The results are shown in Table 3. The specific process is as follows:

The OLED has a structure as ITO layer/HATCN layer (5 nm)/NPB layer (40 nm)/TCTA layer (10 nm)/light-emitting layer (15 nm)/B3PYMPM layer (40 nm)/LiF layer (1 nm)/Al layer (100 nm) ("/" in the foregoing structure represents lamination). The compounds of Examples 1, 2, 3, 4, 6, 8, 11 and CBP were used as the host materials, with Ir(piq)2acac being as the light-emitting material, and light-emitting layer was made by mixing the host material and Ir(piq)2acac in a mass ratio of 90:10; HATCN layer was made of HATCN with HATCN being as a hole injection material; NPB layer and TCTA layer each were made of NPB and TCTA with NPB and TCTA being as hole transporting materials; B3PYMPM layer was made of B3PYMPM with B3PYMPM being as an electron transporting material.

Among them, the structures of HATCH, NPB, TCTA, B3PYMPM, Ir(piq)2acac and CBP were as follows:

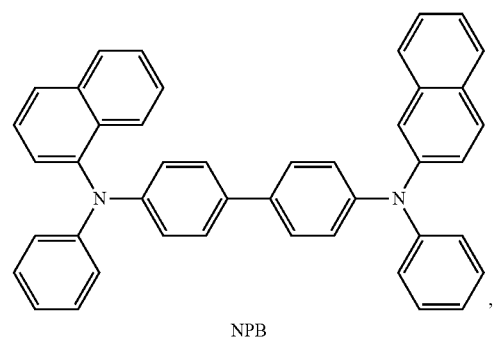

NPB

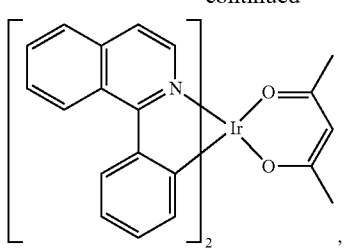

Ir(piq)₂acac

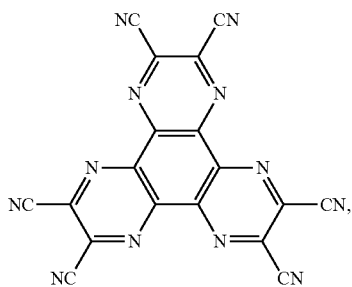

HATCH

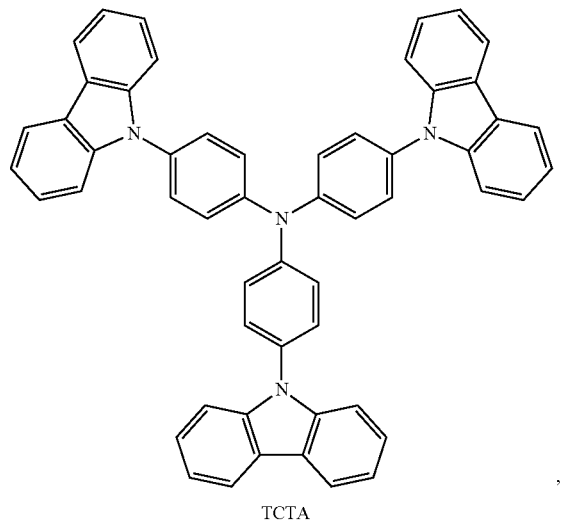

TCTA

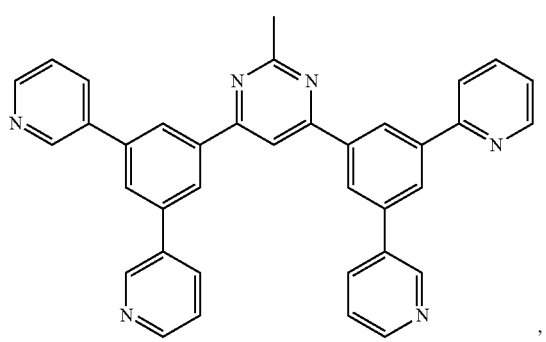

B3PYMPM

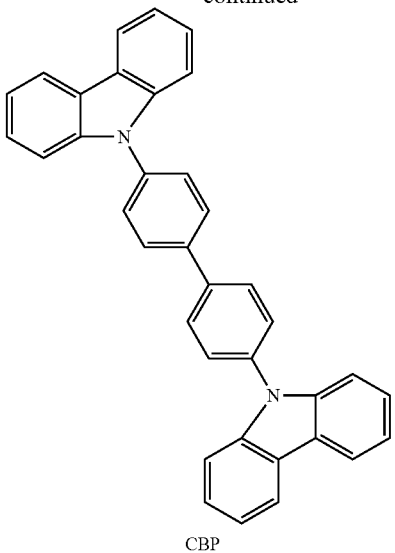

CBP

HATCH, NPB, TCTA, B3PYMPM, Ir(piq)2acac and CBP are all commercially available, such as from Jilin OLED Material Tech Co., Ltd, (www.jl-oled.com), or synthesized by existing synthesis methods which will not be described herein.

The preparation steps of the foregoing OLEDs are as follows:

(1) ITO (indium tin oxide) conductive glass substrates were cleaned using a solvent and treated by UV ozone; wherein the solvent is a mixture of chloroform, acetone and isopropanol in a mass ratio of 5:3:2;

(2) The ITO layer, HATCH layer, NPB layer, TCTA layer, light-emitting layer, B3PYMPM layer, LiF layer, and an Al layer were sequentially formed on the ITO conductive glass substrates by thermal evaporation at $1 \times 10^{-6}$ mbar, and the device was encapsulated with UV-curable resin in a nitrogen glove box to obtain the OLEDs.

Table 3 shows the effects of the compounds of Examples 1, 2, 3, 4, 6, 8 and 11, and the compound CBP as the host materials of the OLEDs on the lifetime of the OLEDs, respectively.

TABLE 3

|  | Lifetime (T90@1000 nits) |
| --- | --- |
| Example 1 | 11.4 |
| Example 2 | 10.2 |
| Example 3 | 8.6 |
| Example 4 | 3.2 |
| Example 6 | 5.3 |
| Example 8 | 6.7 |
| Example 11 | 9.8 |
| CBP | 1 |

It can be seen from Table 3 that the OLEDs with the nitrogen-containing fused heterocyclic compounds of Examples 1, 2, 3, 4, 6, 8, and 11 being as the host materials have a lifetime more than three times longer than the OLED with the CPB being as the host material; wherein the OLED with the nitrogen-containing fused heterocyclic compound of Example 1 being as the host material has a longest lifetime which is ten times longer than the OLED with CPB being as the host material, while the OLEDs with the nitrogen-containing fused heterocyclic compounds of Examples 1, 2, 3, 4, 6, 8, and 11 being as the host materials have a higher luminous efficiency than the OLED with CPB being as the host material. In summary, the OLEDs prepared using nitrogen-containing fused heterocyclic compounds have a higher luminous efficiency and a longer lifetime.

The technical features of the above embodiments may be combined arbitrarily. To make the description succinct, all the possible combinations of the technical features in the above embodiments are not described. However, as long as there is no contradiction in the combination of these technical features, they should be considered as described in this specification.

The above embodiments merely represent several embodiments of the present invention, and the description thereof is more specific and detailed, but they should not be construed as limiting the scope of the invention. It should be noted that for those skilled in the art, several variations and improvements may be made without departing from the concept of the present invention, and these are all within the protection scope of the present invention. Therefore, the scope of protection of the present invention shall be subject to the appended claims.

What is claimed is:

1. A nitrogen-containing fused heterocyclic compound having the following formula:

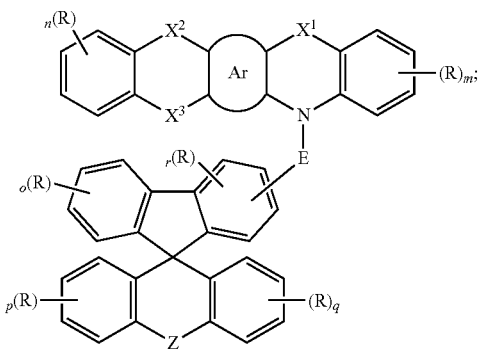

wherein

is an aromatic ring group containing 5 to 30 ring atoms or a heteroaromatic ring group containing 5 to 30 ring atoms;

—$X^1$— and —$X^3$— are each independently selected from the group consisting of a single bond, —N($M^1$)-, —C($M^1$)$_2$-, —Si($M^1$)$_2$-, —O—, —C=N($M^1$)-, —C=C($M^1$)$_2$-, —P($M^1$)-, —P(=O)$M^1$-, —S—, —S=O—, and —SO$_2$—, and —$X^2$—, —$X^3$— are not single bonds simultaneously, wherein $M^1$ is selected from the group consisting of H, D, F, CN, alkenyl, alkynyl, cyano, amino, nitro, acyl, alkoxy, carbonyl, sulfonyl, an alkyl group containing 1 to 30 carbon atoms, a cycloalkyl group containing 3 to 30 carbon atoms, an aromatic ring group containing 5 to 60 ring atoms, and a heteroaromatic ring group containing 5 to 60 ring atoms;

—$X^2$— is independently selected from the group consisting of a single bond, —N($M^1$)-, —Si($M^1$)$_2$-, —O—, —C=N($M^1$)-, —C=C($M^1$)$_2$-, —P($M^1$)-, —P(=O)$M^1$-, —S—, —S=O—, and —SO$_2$—, and —$X^2$—, —$X^3$— are not single bonds simultaneously, wherein $M^1$ is selected from the group consisting of H, D, F, CN, alkenyl, alkynyl, cyano, amino, nitro, acyl, alkoxy, carbonyl, sulfonyl, an alkyl group containing 1 to 30 carbon atoms, a cycloalkyl group containing 3 to 30 carbon atoms, an aromatic ring group containing 5 to 60 ring atoms, and a heteroaromatic ring group containing 5 to 60 ring atoms;

—Z— is one selected from the group consisting of a single bond, —N($M^2$)-, —B($M^2$)-, —C($M^2$)$_2$-, —Si($M^2$)$_2$-, —O—, —S—, —C=N($M^2$)-, —C=C($M^2$)$_2$-, —P($M^2$)-, —P(=O)$M^2$-, —S=O, and —SO$_2$—, wherein $M^2$ is selected from the group consisting of H, D, F, CN, alkenyl, alkynyl, cyano, amino, nitro, acyl, alkoxy, carbonyl, sulfonyl, an alkyl containing 1 to 30 carbon atoms, a cycloalkyl group containing 3 to 30 carbon atoms, an aromatic ring group containing 5 to 60 ring atoms, and a heteroaromatic ring group containing 5 to 60 ring atoms;

R is one selected from the group consisting of is H, D, F, CN, alkenyl, alkynyl, cyano, amino, nitro, acyl, alkoxy, carbonyl, sulfonyl, an alkyl containing 1 to 30 carbon atoms, a cycloalkyl group containing 3 to 30 carbon atoms, an aromatic ring group containing 5 to 60 ring atoms, and a heteroaromatic ring group containing 5 to 60 ring atoms;

m, n, o, p, and q are each independently selected from an integer from 0 to 4, and r is selected from an integer from 0 to 3; and E is a heteroatom-containing electron-accepting group selected from the group consisting of

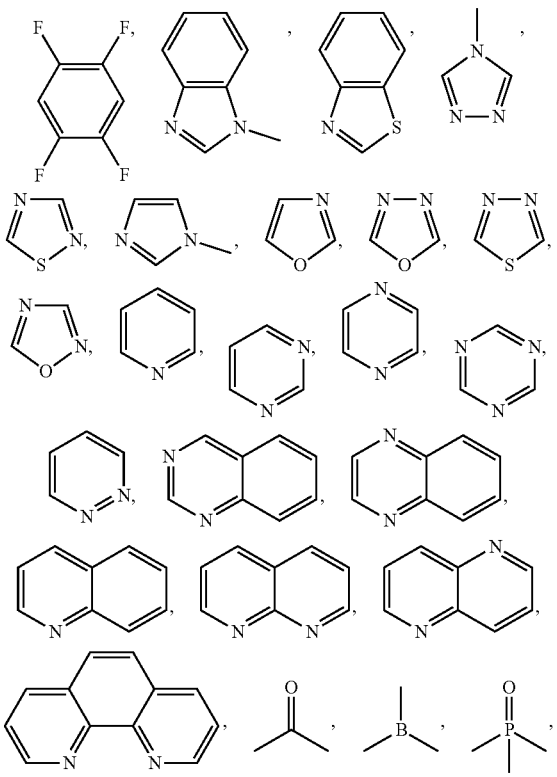

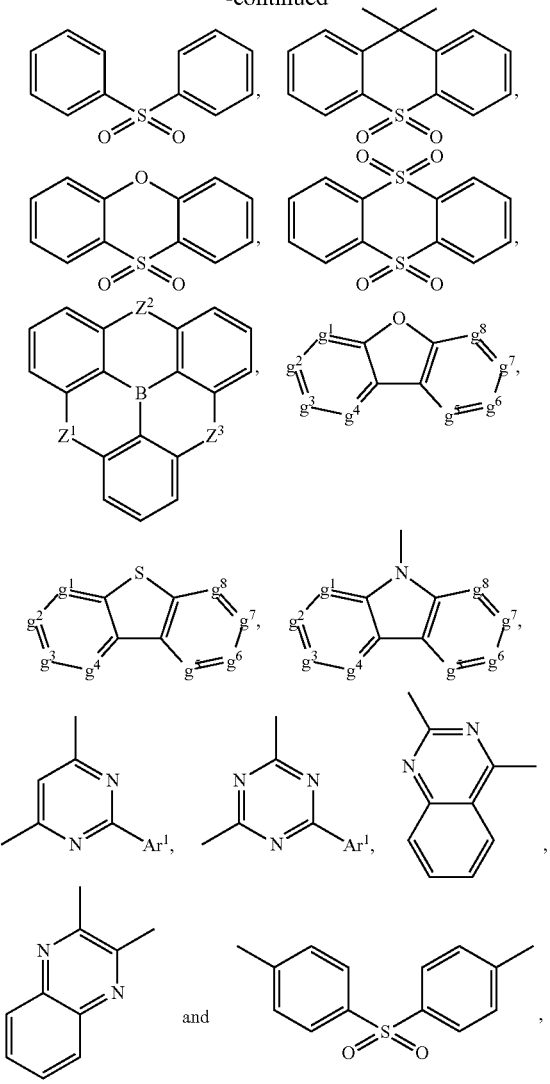

wherein —Z¹—, —Z²—, —Z³— are each independently selected from the group consisting of —N(M³)-, —C(M³)₂-, —Si(M³)₂-, —O—, —C=N(M³)-, —C=C(M³)₂-, —P(M³)-, —P(=O)M³-, —S—, —S=O—, and —SO₂—, or —Z¹—, —Z²—, —Z³— are not present, and M³ is selected from the group consisting of H, D, F, CN, alkenyl, alkynyl, cyano, amino, nitro, acyl, alkoxy, carbonyl, sulfonyl, an alkyl group containing 1 to 30 carbon atoms, a cycloalkyl group containing 3 to 30 carbon atoms, an aromatic ring group containing 5 to 60 ring atoms, and a heteroaromatic ring group containing 5 to 60 ring atoms: g¹, g², g³, g⁴, g⁵, g⁶, q⁷ and g⁸ are each independently selected from CR⁶ and N, and at least one of g¹, g², g³, g⁴, g⁵, g⁶, q⁷ and g⁸ is N, and R⁶ is one selected from the group consisting of H, D, a linear alkyl group containing 1 to 20 carbon atoms, an alkoxy group containing 1 to 20 carbon atoms, a linear thioalkoxy group containing 1 to 20 carbon atoms, a branched alkyl group containing 3 to 20 carbon atoms, a cyclic alkyl group containing 3 to 20 carbon atoms, a branched alkoxy containing 3 to 20 carbon atoms, a cyclic alkoxy containing 3 to 20 carbon atoms, a branched thioalkoxy group containing 3 to 20 carbon atoms, a cyclic thioalkoxy group containing 3 to 20 carbon atoms, a branched silyl group containing 3 to 20 carbon atoms, a cyclic silyl group containing 3 to 20 carbon atoms, a substituted keto group containing 1 to 20 carbon atoms, an alkoxycarbonyl group containing 2 to 20 carbon atoms, an aryloxycarbonyl group containing 7 to 20 carbon atoms, a cyano group, C(=O)NH₂, a haloformyl group, C(=O)—H, an isocyano group, an isocyanate group, a thiocyanate group, an isothiocyanate group, a hydroxyl group, a nitryl group, a CF₃ group, CI, Br, F, a crosslinkable group, a non-substituted aromatic ring system containing 5 to 40 ring atoms, a substituted aromatic ring system containing 5 to 40 ring atoms, a non-substituted heteroaromatic ring system containing 5 to 40 ring atoms, a substituted heteroaromatic ring system containing 5 to 40 ring atoms, an aryloxy group containing 5 to 40 ring atoms, a heteroaryloxy group containing 5 to 40 ring atoms, and one of the combination groups formed by the foregoing groups linked to each other, wherein R⁶ can form a monocyclic aliphatic ring group, a polycyclic aliphatic ring group, a monocyclic aromatic ring group or a polycyclic aromatic ring group by itself; and Ar¹ is one selected from the group consisting of an alkyl group containing 1 to 30 carbon atoms, a cycloalkyl group containing 3 to 30 carbon atoms, an aromatic ring group containing 5 to 60 ring atoms, and a heteroaromatic ring group containing 5 to 60 ring atoms.

2. The compound according to claim 1, wherein

is an aromatic ring group containing 5 to 20 ring atoms or a heteroaromatic ring group containing 5 to 20 ring atoms.

3. The compound according to claim 1, wherein

is one independently selected from the following formulas or one of the combination groups formed by the following formulas linked to each other:

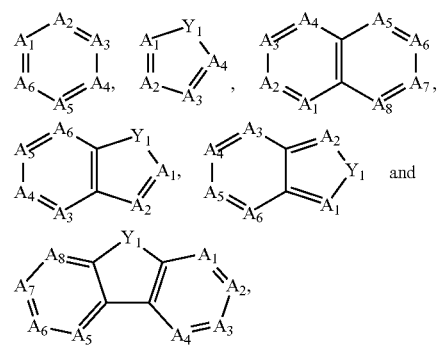

wherein A¹, A², A³, A⁴, A⁵, A⁶, A⁷, and A⁸ are each independently selected from CR³ and N;

Y¹ is one selected from the group consisting of $CR^4R^5$, $SiR^4R^5$, $NR^3$, $C(=O)$, S, and O;

$R^3$, $R^4$, and $R^5$ are each independently selected from the group consisting of H, D, a linear alkyl group containing 1 to 20 carbon atoms, an alkoxy group containing 1 to 20 carbon atoms, a linear thioalkoxy group containing 1 to 20 carbon atoms, a branched alkyl group containing 3 to 20 carbon atoms, a cyclic alkyl group containing 3 to 20 carbon atoms, a branched alkoxy containing 3 to 20 carbon atoms, a cyclic alkoxy containing 3 to 20 carbon atoms, a branched thioalkoxy group containing 3 to 20 carbon atoms, a cyclic thioalkoxy group containing 3 to 20 carbon atoms, a branched silyl group containing 3 to 20 carbon atoms, a cyclic silyl group containing 3 to 20 carbon atoms, a substituted keto group containing 1 to 20 carbon atoms, an alkoxycarbonyl group containing 2 to 20 carbon atoms, an aryloxycarbonyl group containing 7 to 20 carbon atoms, a cyano group, $C(=O)NH_2$, a haloformyl group, $C(=O)$—H, an isocyano group, an isocyanate group, a thiocyanate group, an isothiocyanate group, a hydroxyl group, a nitryl group, a $CF_3$ group, Cl, Br, F, a crosslinkable group, a substituted aromatic ring group containing 5 to 40 ring atoms, a non-substituted aromatic ring group containing 5 to 40 ring atoms, a substituted heteroaromatic ring group containing 5 to 40 ring atoms, a non-substituted heteroaromatic ring group containing 5 to 40 ring atoms, an aryloxy group containing 5 to 40 ring atoms, a heteroaryloxy group containing 5 to 40 ring atoms, and one of the combination groups formed by the foregoing groups linked to each other.

4. The compound according to claim 1, wherein

is one selected from the group consisting of

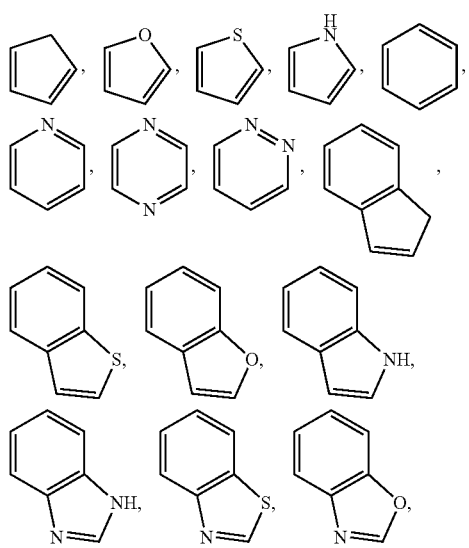

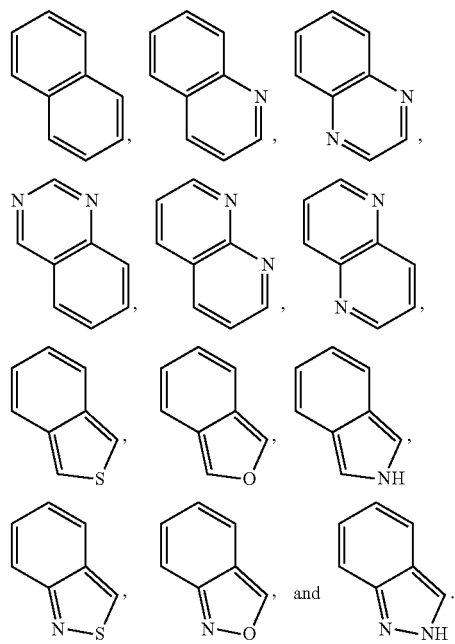

5. The compound according to claim 1, wherein the compound has a formula selected from the group consisting of

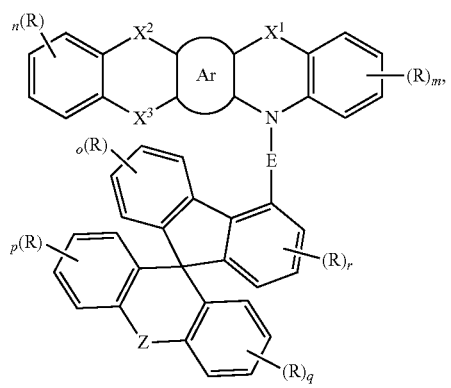

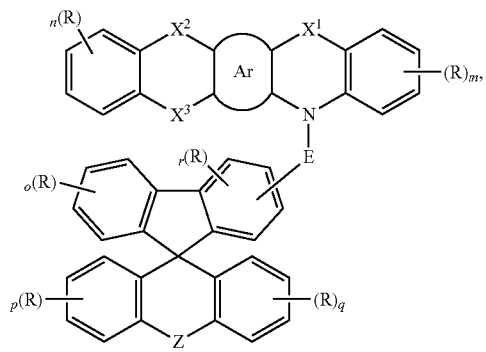

-continued
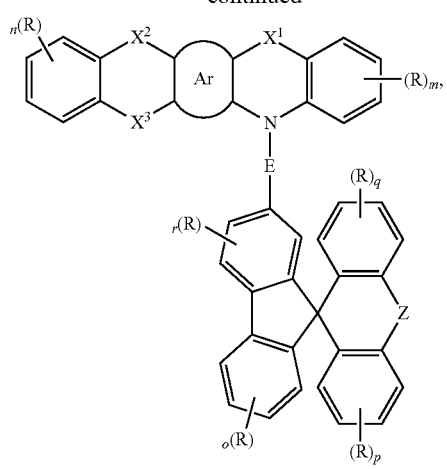
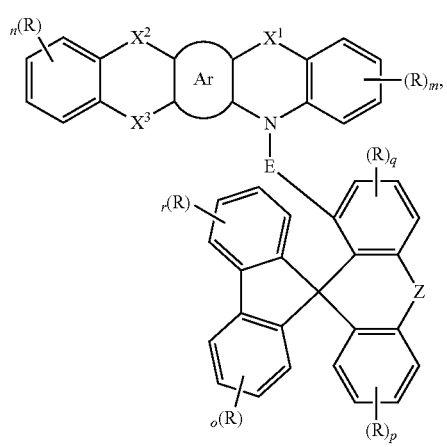
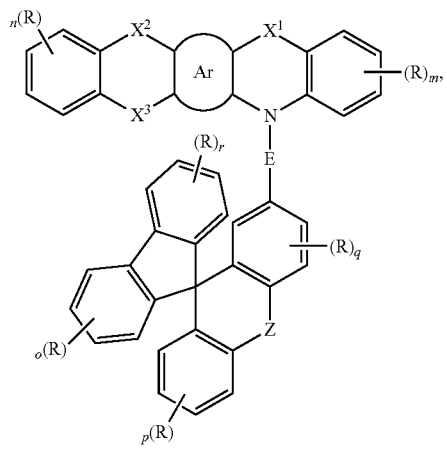
-continued
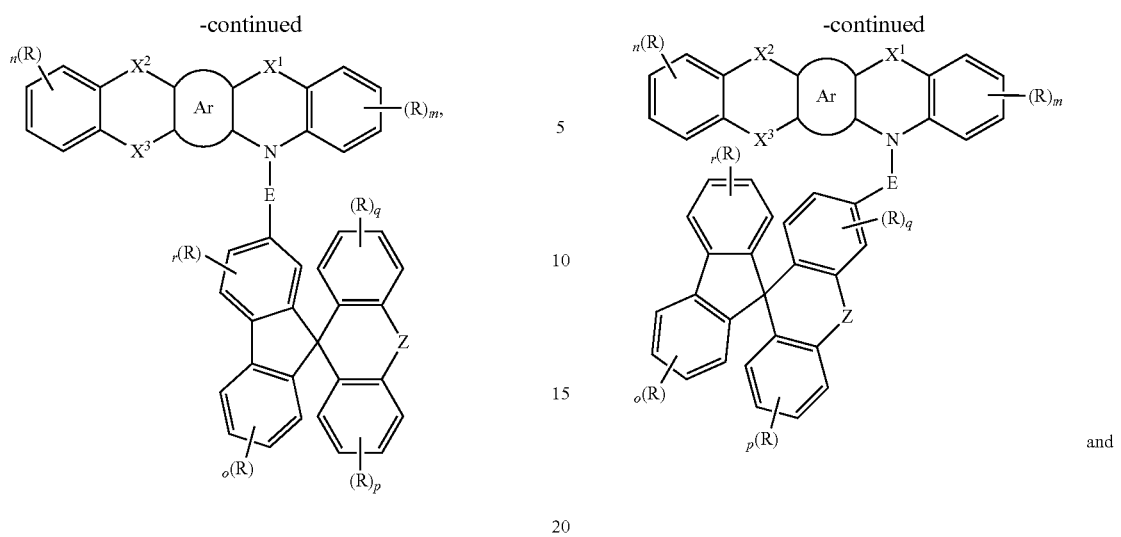
6. The compound according to claim 1, wherein the compound has a formula selected from the group consisting of
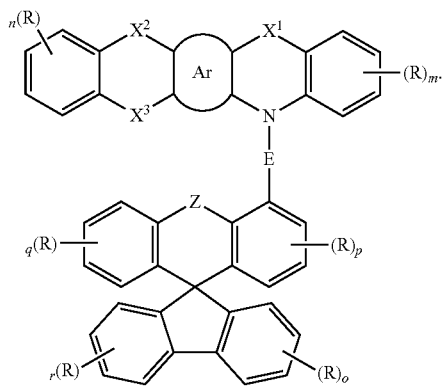
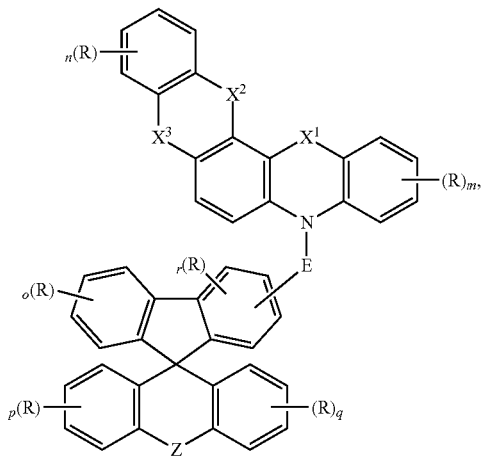

-continued
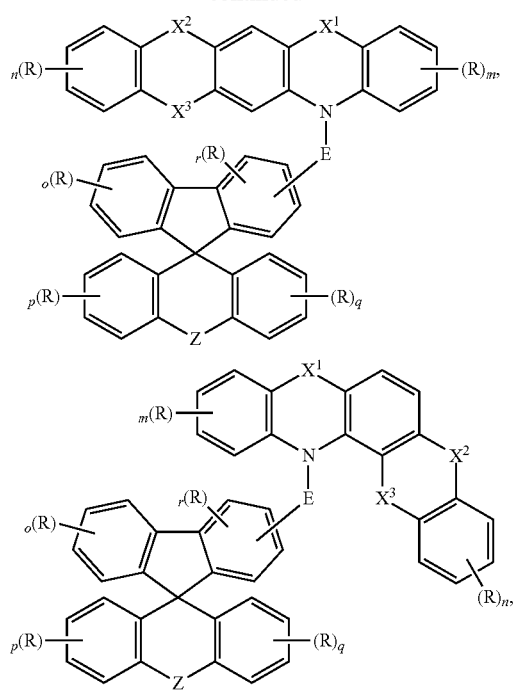
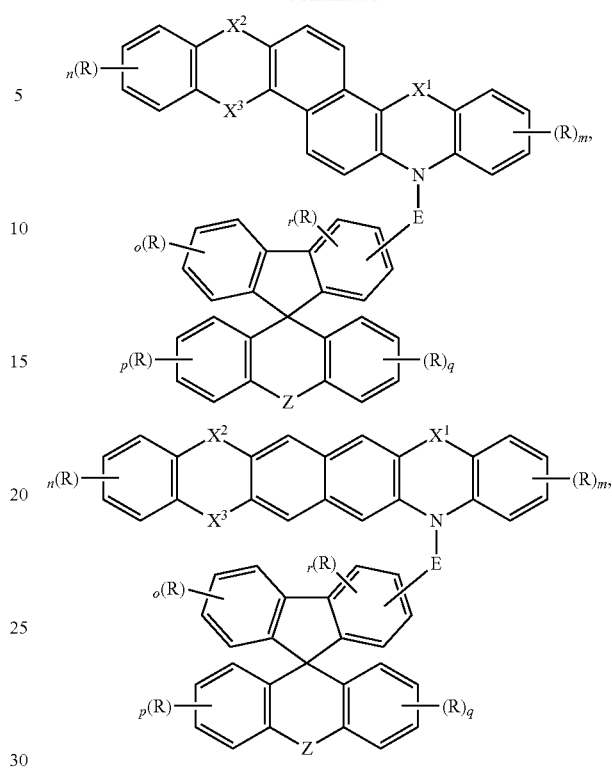
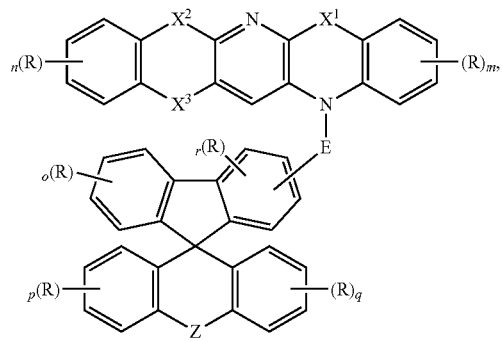
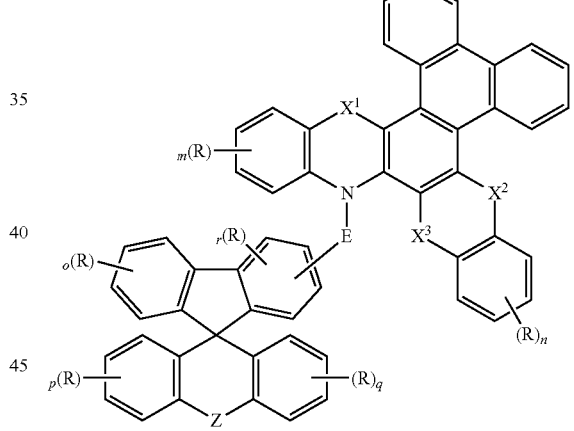
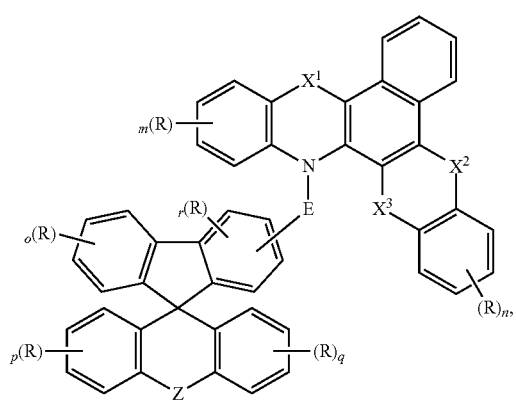
and
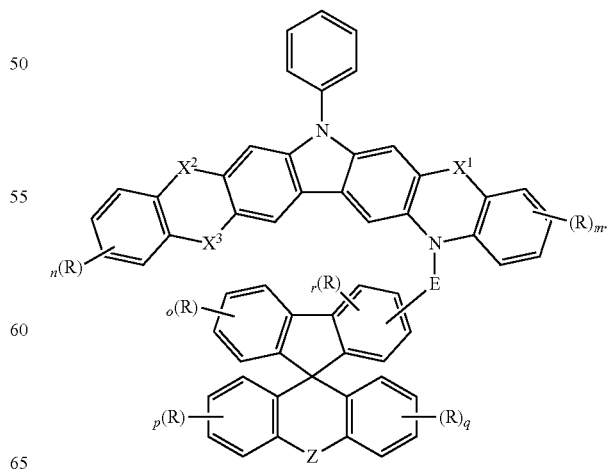

7. The compound according to claim 1, wherein the compound has a formula selected from the group consisting of
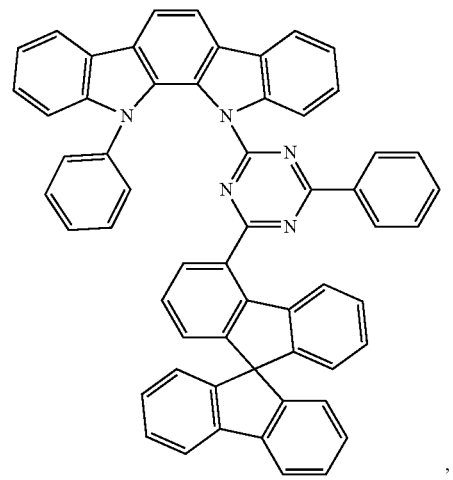
,
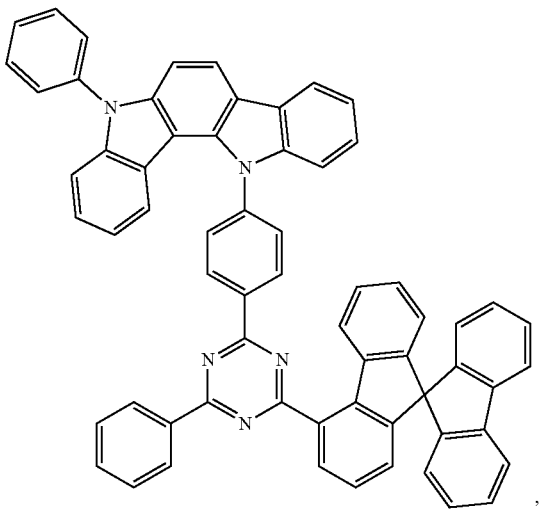
,
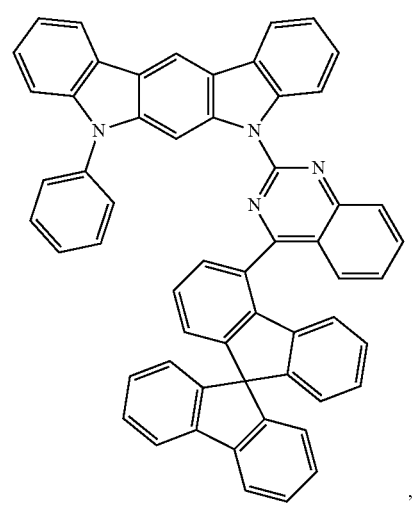
,
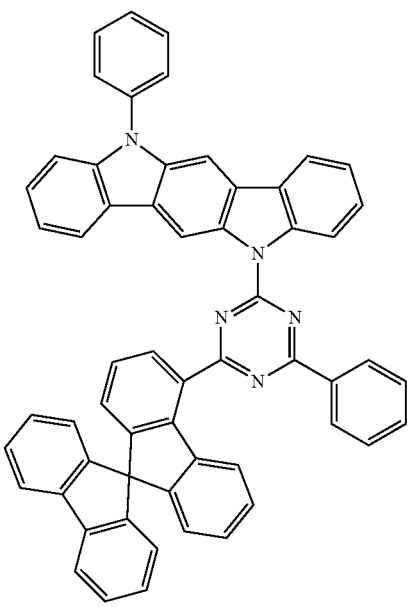
,
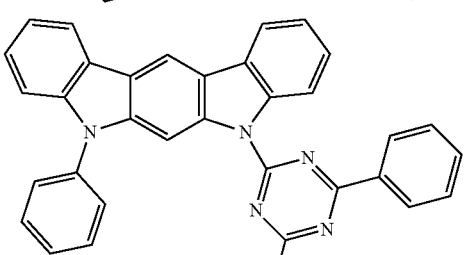
,
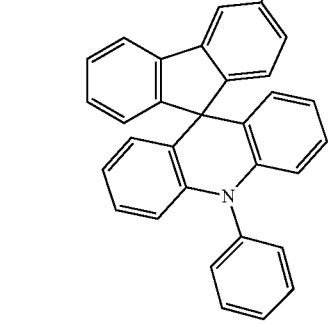
,
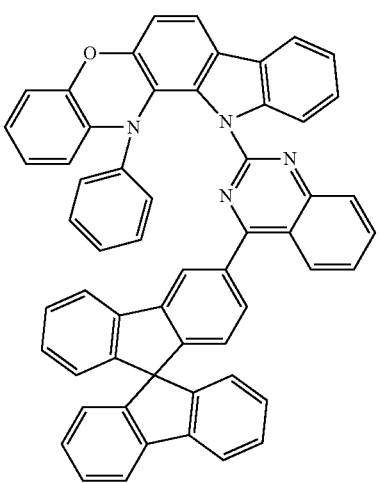
, -continued

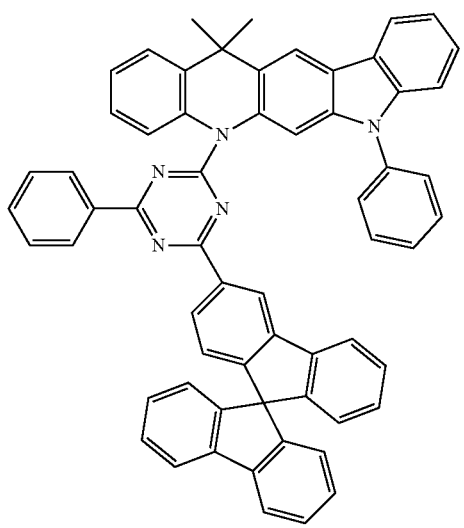
and

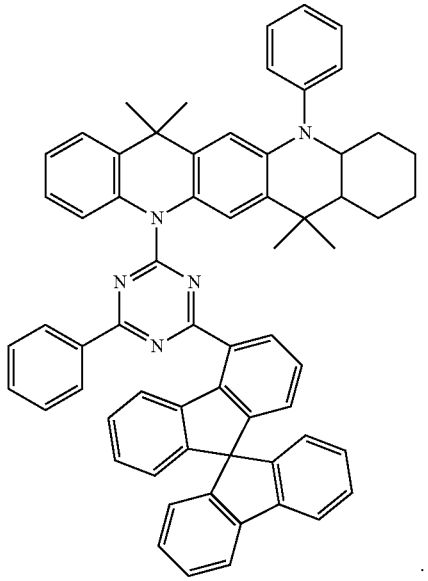

8. The compound according to claim 1, wherein the compound has a $T_1$ greater than or equal to 2.0 eV, wherein $T_1$ presents the triplet excited state energy level.

9. The compound according to claim 1, wherein the compound has a $\Delta E_{ST}$ less than or equal to 0.30 eV, wherein $\Delta E_{ST}$ presents the difference between the triplet excited state energy level and the singlet excited state energy level.

10. The compound according to claim 1, wherein the compound has the following formula:

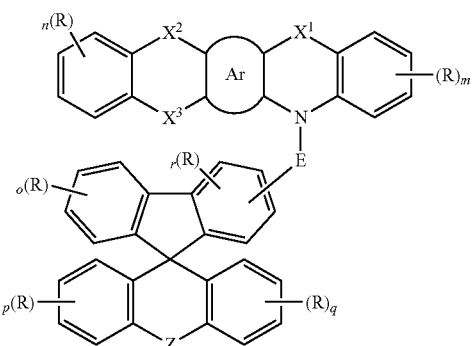

wherein at least one of $-X^2-$ and $-X^3-$ is $-N(M^1)-$.

11. The compound according to claim 1, wherein the compound has a formula selected from the group consisting of:

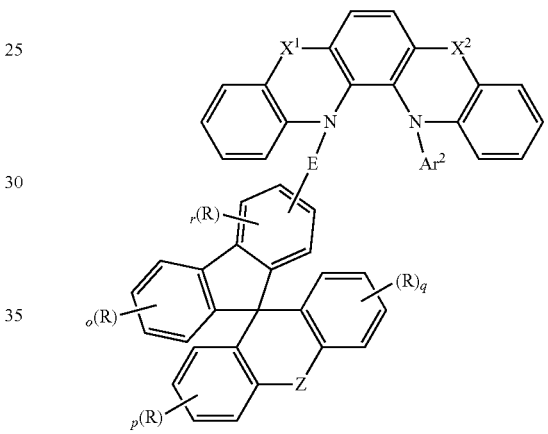

,

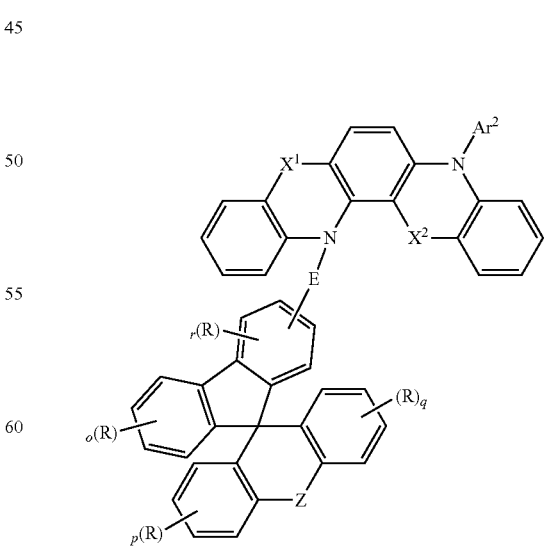

,

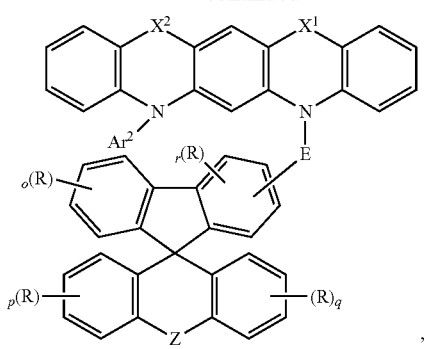

,

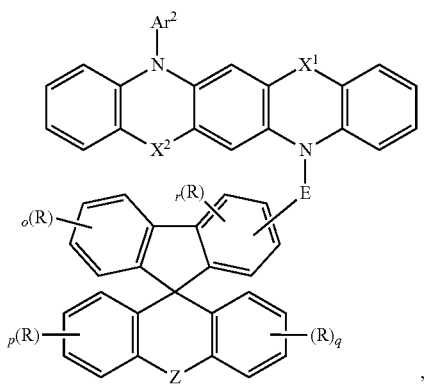

,

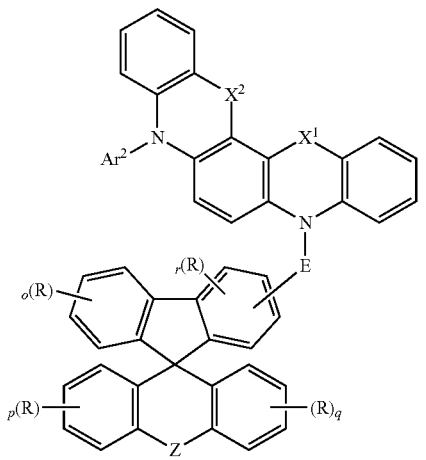

and

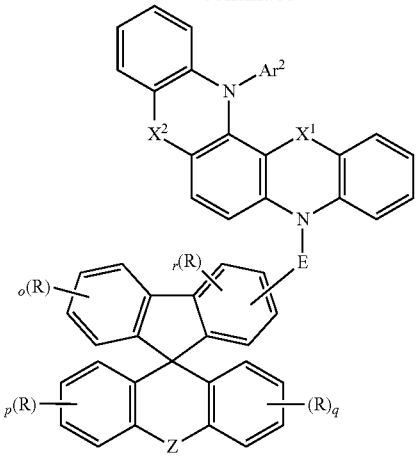

wherein Ar2 is selected from the group consisting of an alkyl group containing 1 to 20 carbon atoms, a cycloalkyl group containing 3 to 20 carbon atoms, an aromatic ring group containing 6 to 30 ring atoms, and a heteroaromatic ring group containing 6 to 30 ring atoms.

12. The compound according to claim 1, wherein —Z— is one selected from the group consisting of a single bond, —N($M^2$)-, C($M^2$)$_2$-, —O—, and —S—.

13. An organic electroluminescent material comprising a compound according to claim 1.

14. The organic electroluminescent material according to claim 13, further comprising an organic functional material having a mass percentage of 0.01 wt % to 50 wt % of the organic electroluminescent material, wherein the compound according to claim 1 has a mass percentage of 50 wt % to 99.9 wt % of the organic electroluminescent material; wherein the organic functional material is at least one selected from the group consisting of a hole injection material, a hole transporting material, an electron injection material, an electron transporting material, a hole blocking material, an electron blocking material, a light-emitting material, a host material, and an organic dye.

15. The organic electroluminescent material according to claim 13, further comprising an organic solvent having a mass percentage of 70 wt % to 99.7 wt % of the organic electroluminescent material, and wherein the compound according to claim 1 has a mass percentage of 0.3 wt % to 30 wt % of the organic electroluminescent material; wherein the organic solvent is at least one selected from an aromatic solvent, a heteroaromatic solvent, an aromatic ketone solvent, an aromatic ether solvent, an ester solvent, an aliphatic ketone solvent, and an aliphatic ether solvent.

16. An electronic device comprising a compound according to claim 1.

17. The electronic device according to claim 16, wherein the electronic device is an organic electroluminescent device comprising a light-emitting layer comprising the compound according to claim 1.

* * * * *